(12) United States Patent
Fiorina et al.

(10) Patent No.: US 10,071,167 B2
(45) Date of Patent: Sep. 11, 2018

(54) METHOD OF PREVENTING AND TREATING TYPE 1 DIABETES, ALLOGRAFT REJECTION AND LUNG FIBROSIS (BY TARGETING THE ATP/P2X7R AXIS)

(71) Applicant: CHILDREN'S MEDICAL CENTER CORPORATION, Boston, MA (US)

(72) Inventors: Paolo Fiorina, Boston, MA (US); Andrea Vergani, Brookline, MA (US)

(73) Assignee: CHILDREN'S MEDICAL CENTER CORPORATION, Boston, MA (US)

(*) Notice: Subject to any disclaimer, the term of this patent is extended or adjusted under 35 U.S.C. 154(b) by 111 days.

(21) Appl. No.: 14/786,424

(22) PCT Filed: May 5, 2014

(86) PCT No.: PCT/US2014/036755
§ 371 (c)(1),
(2) Date: Oct. 22, 2015

(87) PCT Pub. No.: WO2014/182601
PCT Pub. Date: Nov. 13, 2014

(65) Prior Publication Data
US 2016/0067348 A1    Mar. 10, 2016

Related U.S. Application Data

(60) Provisional application No. 61/820,763, filed on May 8, 2013.

(51) Int. Cl.
| A61K 47/48 | (2006.01) |
| A61K 31/436 | (2006.01) |
| A61K 31/7076 | (2006.01) |
| A61K 45/06 | (2006.01) |
| A61K 31/166 | (2006.01) |
| A61K 31/402 | (2006.01) |
| A61K 31/53 | (2006.01) |
| A61K 47/68 | (2017.01) |

(52) U.S. Cl.
CPC ...... *A61K 47/48369* (2013.01); *A61K 31/166* (2013.01); *A61K 31/402* (2013.01); *A61K 31/436* (2013.01); *A61K 31/53* (2013.01); *A61K 31/7076* (2013.01); *A61K 45/06* (2013.01); *A61K 47/68* (2017.08)

(58) Field of Classification Search
None
See application file for complete search history.

(56) References Cited

U.S. PATENT DOCUMENTS

| 7,317,018 B2 | 1/2008 | Ferrero |
| 2009/0220516 A1 | 9/2009 | Laties et al. |
| 2010/0144727 A1 | 6/2010 | Beswick et al. |
| 2012/0035350 A1 | 2/2012 | Franco |

FOREIGN PATENT DOCUMENTS

| EP | 1741722 A2 | 1/2007 |
| WO | 2004/092384 A2 | 10/2004 |
| WO | 2009/033234 A1 | 3/2009 |
| WO | 2009/118175 A1 | 10/2009 |
| WO | 2010/118921 A1 | 10/2010 |
| WO | 2011/072012 A2 | 6/2011 |
| WO | 2013/178783 A1 | 12/2013 |

OTHER PUBLICATIONS

Lang, P.A., et al. Eur. J. Immunol. 2010;40:2401-2408.*
Vonend et al. "P2X7 receptor expression in diabetic nephropathy", Journal of the American Society of Nephrology, 12:849A-850A (2001).
Arulkumaran et al., "A potential therapeutic role for P2X7 receptor (P2X7R) antagonists in the treatment of inflammatory diseases", Expert Opin Investig Drugs, 20(7):897-915 (2011).
Vergani et al., "Effect of the Purinergic Inhibitor Oxidized-ATP in a Model of Islet Allograft Rejection", Diabetes 62 (5):1665-1675 (2013).
Vergani et al., "Long-Term Heart Transplant Survival by Targeting the Ionotropic Purinergic Receptor P2X7", Circulation, 127(4):463-475 (2013).
Vonend et al., "Glomerular expression of the ATP-sensitive P2X7 receptor in diabetic and hypertensive rat models", Kindney Int., 66(1):157-166 (2004).

* cited by examiner

*Primary Examiner* — Gerald R Ewoldt
(74) *Attorney, Agent, or Firm* — Nixon Peabody LLP; David S. Resnick; Nicole D. Kling

(57) ABSTRACT

The present invention relates to the role of purinergic receptors and ATP in T cell activation and autocrine system signaling. In one embodiment, the present invention provides a method of preventing or treating diabetes by administering a therapeutically effective inhibitor of ATP to a subject. In another embodiment, the present invention provides a method of preventing or treating fibrosis by administering a P2X7R soluble fusion protein. In another embodiment, the present invention provides a method of preventing or treating graft rejection by administering an inhibitor of P2X receptor signaling.

2 Claims, 28 Drawing Sheets
Specification includes a Sequence Listing.

FIG. 4B　　FIG. 4C　　FIG. 4D

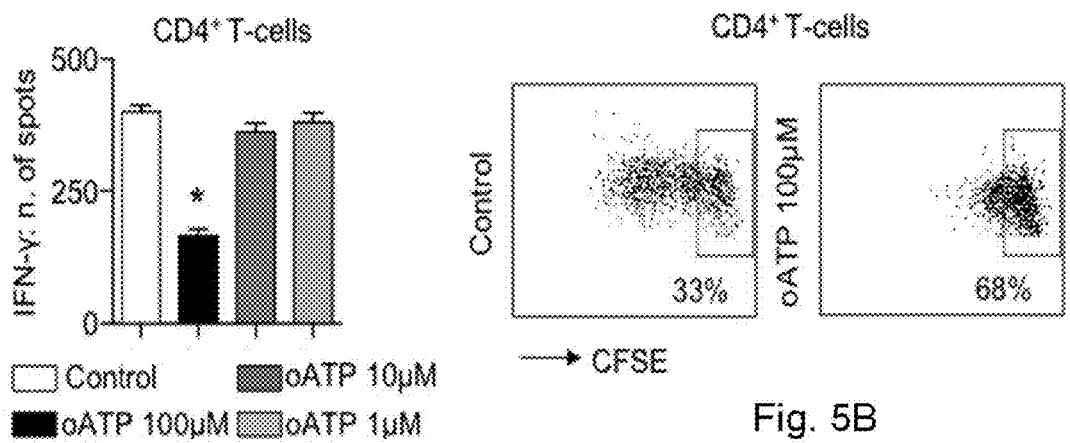
Fig. 5A
Fig. 5B
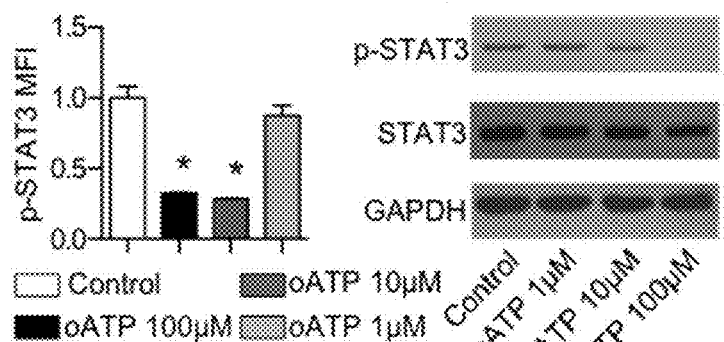
Fig. 5C
Fig. 5D
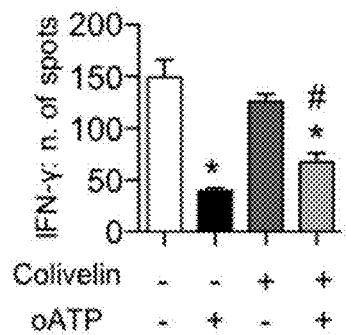
Fig. 5E

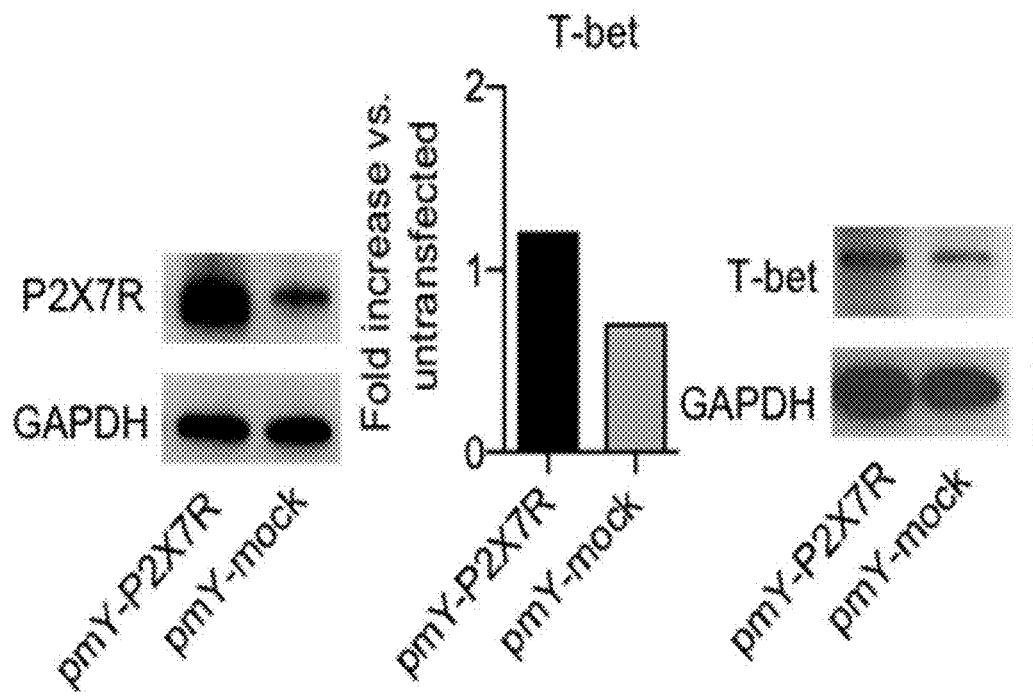
Fig. 6E
Fig. 6F
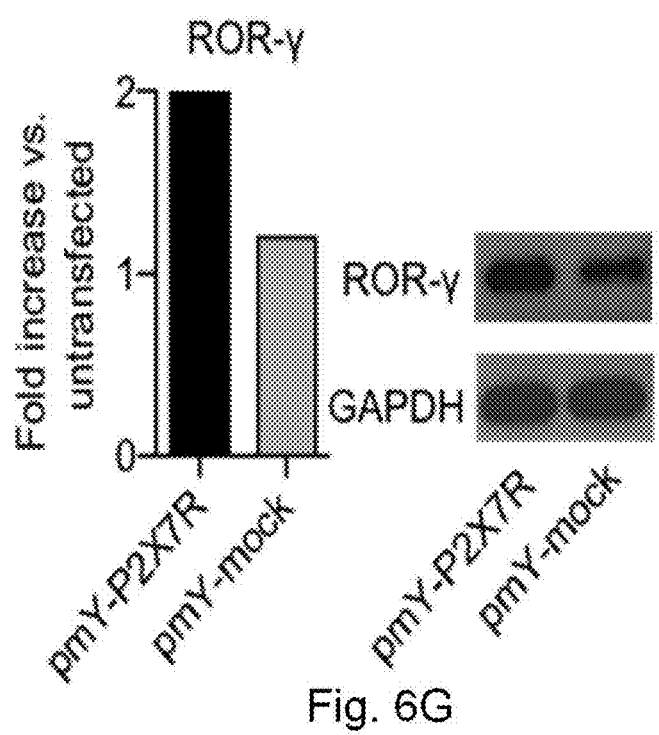
Fig. 6G

MPACCSCSCDVFQYETNKVTRIQSMNYGTIKWFFHVIIFSYVCF
ALVSDKLYQRKEPVISSVHTKVKGIAEVKEEIVENGVKKLVHSV
FDTADYTFPLQGNSFFVMTNFLKTEGQEQRLCPEYPTRRTLC
SSDRGCKKGWMDPQSKGIQTGRCVVYEGNQKTCEVSAWCP
IEAVEE<u>APRPALL</u>NSAENFTVLIKNNIDFPGHNYTTRNILPGLNI
TCTFHKTQNPQCPIFRLGDIFRETGDNFSDVAIQGGIMGIEIYW
DCNLDRWFHHCRPKYSFRRLDDKTTNVSLYPGYNFRYAKYY
KENNVEKRTLIKVFGIRFDILVFGTGGKFDIIQLVVY*IGSTLSYFG
LAAVFIDFLID***TYSSNCCRSHIYPWCKCCQPCVVNEYYYRKKC
ESIVEPKPTLKYVSFVDESHIRMVNQQLLGRSLQDVKGQEVP
RPAMDFTDLSRLPLALHDTPPIPGQPEEIQLLRKEATPRSRDS
PVWCQCGSCLPSQLPESHRCLE<u>E</u>LCCRKKPGACITTSELFRK
LVLSRHVLQFLLLYQEPLLALDVDSTNSRLRHCAYRCYATWRF
GSQDMADFAILPSCCRWRIRKEFPKSEGQYSGFKSPY**

Fig. 10B

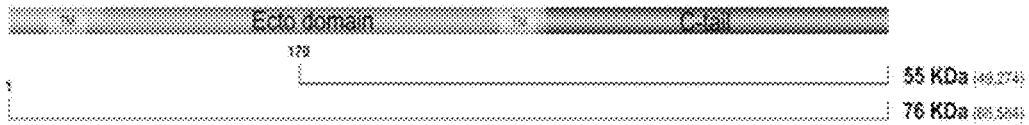

Fig. 10C

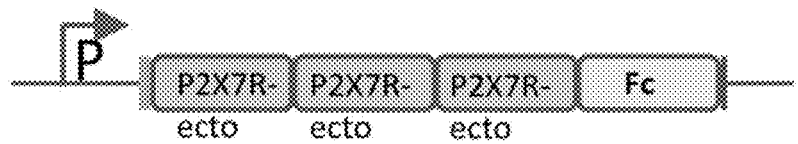

Fig. 10D

SEQUENCE LISTING

<160> NUMBER OF SEQ ID NOS: 4

<210> SEQ ID NO 1
<211> LENGTH: 595
<212> TYPE: PRT
<213> ORGANISM: Homo sapiens

<400> SEQUENCE: 1

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
                35                  40                  45

Lys Leu Tyr Gln Arg Lys Glu Pro Val Ile Ser Ser Val His Thr Lys
    50                  55                  60

Val Lys Gly Ile Ala Glu Val Lys Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
            115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
            195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
            355                 360                 365

Pro Trp Cys Lys Cys Cys Gln Pro Cys Val Val Asn Glu Tyr Tyr Tyr
            370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
```

```
                    405                 410                 415
Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
            485                 490                 495

Leu Cys Cys Arg Lys Lys Pro Gly Ala Cys Ile Thr Thr Ser Glu Leu
        500                 505                 510

Phe Arg Lys Leu Val Leu Ser Arg His Val Leu Gln Phe Leu Leu Leu
    515                 520                 525

Tyr Gln Glu Pro Leu Leu Ala Leu Asp Val Asp Ser Thr Asn Ser Arg
530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
            565                 570                 575

Ile Arg Lys Glu Phe Pro Lys Ser Glu Gly Gln Tyr Ser Gly Phe Lys
        580                 585                 590

Ser Pro Tyr
    595

<210> SEQ ID NO 2
<211> LENGTH: 290
<212> TYPE: PRT
<213> ORGANISM: Homo sapiens

<400> SEQUENCE: 2

Ser Asp Lys Leu Tyr Gln Arg Lys Glu Pro Val Ile Ser Ser Val His
1               5                   10                  15

Thr Lys Val Lys Gly Ile Ala Glu Val Lys Glu Ile Val Glu Asn
            20                  25                  30

Gly Val Lys Lys Leu Val His Ser Val Phe Asp Thr Ala Asp Tyr Thr
        35                  40                  45

Phe Pro Leu Gln Gly Asn Ser Phe Phe Val Met Thr Asn Phe Leu Lys
    50                  55                  60

Thr Glu Gly Gln Glu Gln Arg Leu Cys Pro Glu Tyr Pro Thr Arg Arg
65                  70                  75                  80

Thr Leu Cys Ser Ser Asp Arg Gly Cys Lys Lys Gly Trp Met Asp Pro
            85                  90                  95

Gln Ser Lys Gly Ile Gln Thr Gly Arg Cys Val Val Tyr Glu Gly Asn
        100                 105                 110

Gln Lys Thr Cys Glu Val Ser Ala Trp Cys Pro Ile Glu Ala Val Glu
    115                 120                 125

Glu Ala Pro Arg Pro Ala Leu Leu Asn Ser Ala Glu Asn Phe Thr Val
130                 135                 140

Leu Ile Lys Asn Asn Ile Asp Phe Pro Gly His Asn Tyr Thr Thr Arg
145                 150                 155                 160

Asn Ile Leu Pro Gly Leu Asn Ile Thr Cys Thr Phe His Lys Thr Gln
            165                 170                 175
```

```
Asn Pro Gln Cys Pro Ile Phe Arg Leu Gly Asp Ile Phe Arg Glu Thr
                180                 185                 190

Gly Asp Asn Phe Ser Asp Val Ala Ile Gln Gly Gly Ile Met Gly Ile
            195                 200                 205

Glu Ile Tyr Trp Asp Cys Asn Leu Asp Arg Trp Phe His His Cys Arg
    210                 215                 220

Pro Lys Tyr Ser Phe Arg Arg Leu Asp Asp Lys Thr Thr Asn Val Ser
225                 230                 235                 240

Leu Tyr Pro Gly Tyr Asn Phe Arg Tyr Ala Lys Tyr Tyr Lys Glu Asn
                245                 250                 255

Asn Val Glu Lys Arg Thr Leu Ile Lys Val Phe Gly Ile Arg Phe Asp
            260                 265                 270

Ile Leu Val Phe Gly Thr Gly Gly Lys Phe Asp Ile Ile Gln Leu Val
    275                 280                 285

Val Tyr
    290

<210> SEQ ID NO 3
<211> LENGTH: 3680
<212> TYPE: DNA
<213> ORGANISM: Homo sapiens

<400> SEQUENCE: 3
gtcattggag gagcttgaag ttaaagactc ctgctaaaaa ccagtacgtt tcattttgca        60
gttactggga gggggcttgc tgtggccctg tcaggaagag tagagctctg gtccagctcc       120
gcgcagggag ggaggctgtc accatgccgg cctgctgcag ctgcagtgat gttttccagt       180
atgagacgaa caaagtcact cggatccaga gcatgaatta tggcaccatt aagtggttct       240
tccacgtgat catctttttcc tacgtttgct ttgctctggt gagtgacaag ctgtaccagc       300
ggaaagagcc tgtcatcagt tctgtgcaca ccaaggtgaa ggggatagca gaggtgaaag       360
aggagatcgt ggagaatgga gtgaagaagt tggtgcacag tgtctttgac accgcagact       420
acaccttccc tttgcagggg aactcttttct tcgtgatgac aaactttctc aaaacagaag       480
gccaagagca gcggttgtgt cccgagtatc cacccgcag acgctctgt tcctctgacc         540 gaggttgtaa aagggatgg atggacccgc agagcaaagg aattcagacc ggaaggtgtg        600
tagtgtatga agggaaccag aagacctgtg aagtctctgc ctggtgcccc atcgaggcag       660
tggaagaggc ccccggcct gctctcttga acagtgccga aaacttcact gtgctcatca        720
agaacaatat cgacttcccc ggccacaact acaccgag aaacatcctg ccaggtttaa         780
acatcacttg taccttccac aagactcaga atccacagtg tccattttttc cgactaggag       840 acatcttccg agaaacaggc gataatttttt cagatgtggc aattcagggc ggaataatgg       900
gcattgagat ctactgggac tgcaacctag accgttggtt ccatcactgc cgtcccaaat       960
acagtttccg tcgccttgac gacaagacca ccaacgtgtc cttgtaccct ggctacaact      1020
tcagatacgc caagtactac aaggaaaaca atgttgagaa acggactctg ataaaagtct      1080
tcgggatccg tttttgacatc ctggttttttg gcaccggagg aaaatttgac attatccagc      1140
tggttgtgta catcggctca accctctcct acttcggtct ggccgctgtg ttcatcgact      1200
tcctcatcga cacttactcc agtaactgct gtcgctccca tatttatccc tggtgcaagt      1260
gctgtcagcc ctgtgtggtc aacgaatact actacaggaa gaagtgcgag tccattgtgg      1320
agccaaagcc gacattaaag tatgtgtcct ttgtggatga atcccacatt aggatggtga      1380
accagcagct actagggaga agtctgcaag atgtcaaggg ccaagaagtc ccaagacctg      1440
```

```
cgatggactt cacagatttg tccaggctgc ccctggccct ccatgacaca ccccgattc    1500 ctggacaacc agaggagata cagctgctta gaaaggaggc gactcctaga tccagggata   1560
gccccgtctg gtgccagtgt ggaagctgcc tcccatctca actccctgag agccacaggt   1620
gcctggagga gctgtgctgc cggaaaaagc cgggggcctg catcaccacc tcagagctgt   1680
tcaggaagct ggtcctgtcc agacacgtcc tgcagttcct cctgctctac caggagccct   1740
tgctggcgct ggatgtggat tccaccaaca gccggctgcg gcactgtgcc tacaggtgct   1800
acgccacctg gcgcttcggc tcccaggaca tggctgactt tgccatcctg cccagctgct   1860
gccgctggag gatccggaaa gagtttccga agagtgaagg gcagtacagt ggcttcaaga   1920
gtccttactg aagccaggca ccgtggctca cgtctgtaat cccagcgctt gggaggccg    1980 aggcaggcag atcacctgag gtcgggagtt ggagacccgc ctggctaaca aggcgaaatc   2040
ctgtctgtac taaaaataca aaaatcagcc agacatggtg gcatgcacct gcaatcccag   2100
ctactcggga ggctgaggca caagaatcac ttgaacccgg gaggcagagg ttgtagtgag   2160
cccagattgt gccactgctc tccagcctgg gaggcacagc aaactgtccc ccaaaaaaaa   2220
aaaagagtcc ttaccaatag caggggctgc agtagccatg ttaacatgac atttaccagc   2280
aacttgaact tcacctgcaa agctctgtgg ccacattttc agccaaaggg aaatatgctt   2340
tcatcttctg ttgctctctg tgtctgagag caaagtgacc tggttaaaca aaccagaatc   2400
cctctacatg gactcagaga aaagagattg agatgtaagt ctcaactctg tccccaggaa   2460
gttgtgtgac cctaggcctc tcacctctgt gcctctgtct ccttgttgcc caactactat   2520
ctcagagata ttgtgaggac aaattgagac agtgcacatg aactgtcttt taatgtgtaa   2580
agatctacat gaatgcaaaa catttcatta tgaggtcaga ctaggataat gtccaactaa   2640
aaacaaaccc ttttcatcct ggctggagaa tgtggagaac taaggtggc cacaaattct    2700 ttgacactca gtcccccaa gacctaaggg ttttatctcc tccccttgaa tatgggtggc    2760
tctgattgct ttatccaaaa gtggaagtga cattgtgtca gtttcagatc ctgatcttaa   2820
gaggctgaca gcttctactt gctgtccctt ggaactcttg ctatcgggga agccagacgc   2880
catttaaaag tctgcctatc ctggccaggt gtggtggctc acacctgtaa tcccagcact   2940
ttgggagacc aaggcgggcg gatcacttaa agtcaggagt ccaagaccag actcgccaac   3000
atggtgaaac cgtatctcta ataaaaatac aaaaattagc tgggcatggt gcgggcacct   3060
gtagtcctag ctatcaagag gctgagacag gagaaacact tgaacctggg aggtggaggt   3120
tgcattgagc tgagatcgtg ccactgcact ccaggctggg tgacagagcg agactccatc   3180
tcaaaaaaaa aaaaagaaa aaaaaatgt ctgcctatcc tgagactgcc ctgctgtgag     3240
gaagcccaag cagtcacgtg gacagtgcct gaccagcccc agctttcaag ccatccaagc   3300
ccagtcacca acatgagag agaagaagcc ttcaggtgat tctggactcc actaacatat    3360
gactgatacc gcatgataca tcccaagtga aactgcccc ataaatccag aaaccacat     3420 tgctatctta agtccctaag tttggggctt atttgttcca cagcaacagg taactggaac   3480
agagggcaag cctgatgaat gggcacacag actcagccca taccttccct ggttctaatg   3540
ttctcaggga gcccggacca accctgggag cctcaggaac ttaggtttcc actgacagt    3600 tctagaaggg ctatagacca aatcaggtaa ctcaccagac cagccttgga atctatcaaa   3660
tctaactgct gagctaccca                                               3680
```

<210> SEQ ID NO 4

```
<211> LENGTH: 595
<212> TYPE: PRT
<213> ORGANISM: Homo sapiens

<400> SEQUENCE: 4

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
```

```
385                 390                 395                 400

Val Ser Phe Val Asp Glu Ser His Ile Arg Met Val Asn Gln Gln Leu
            405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
            485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
            565                 570                 575

Ile Arg Lys Glu Phe Pro Lys Ser Glu Gly Gln Tyr Ser Gly Phe Lys
            580                 585                 590

Ser Pro Tyr
    595
```

METHOD OF PREVENTING AND TREATING TYPE 1 DIABETES, ALLOGRAFT REJECTION AND LUNG FIBROSIS (BY TARGETING THE ATP/P2X7R AXIS)

CROSS-REFERENCE TO RELATED APPLICATIONS

This application is a 35 U.S.C. § 371 National Phase Entry Application of International Application No. PCT/US2014/036755 filed May 5, 2014, which designates the U.S., and which claims benefit under 35 U.S.C. § 119(e) of U.S. Provisional Application No. 61/820,763 filed May 8, 2013, the contents of which are incorporated herein by reference in their entirety.

SEQUENCE LISTING

The instant application contains a Sequence Listing which has been filed electronically in ASCII format and is hereby incorporated by reference in its entirety. Said ASCII copy, created on Feb. 26, 2018, is named 701039-077062-US_S-L.txt and is 18,121 bytes in size.

FIELD OF INVENTION

This invention relates to the treatment of diabetes, autoimmunity diseases, inflammatory diseases and transplantation procedures.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The current mainstay of treatment for type 1 diabetes (T1D) is insulin therapy, which has proven to be a lifesaving breakthrough. However, insulin treatment cannot fully prevent the severe complications related to the disease, including kidney failure and coronary heart disease. Successful islet transplantation can cure T1D, improve glycometabolic control, reduce hypoglycemic episodes, and halt diabetes complications. Unfortunately, the rate of functioning islet allografts at 5 years is well below 20%, primarily, although not exclusively, due to alloreactive and autoreactive immune responses. T cells recognize antigens through their T cell receptors (TCRs), which localize to the immune synapse and physically interact with peptides that are presented on MHC molecules by antigen-presenting cells (APCs). The anti-islet immune response involves a complex interplay between pathogenic and inflammatory immune pathways, which promote rejection, and regulatory or anti-inflammatory immune pathways, which facilitate tolerance toward transplants; one such pathway is the purinergic system. The purine ATP is a small molecule present at high concentrations within cells and released after cell damage or death and immune cell activation; it acts as a danger signal and potent chemotactic mediator. ATP is abundant at inflammation sites and is sensed by ionotropic purinergic P2X receptors (seven receptors named P2X1-P2X7, or P2XRs). P2X receptors can function as calcium channels, and autocrine activation of these receptors can facilitate calcium influx and downstream signaling. In leukocytes, P2XRs can regulate cytokine production, activation, and apoptosis, thus constituting an "autocrine alerting system". In particular, P2X7R can serve as a signal amplification mechanism for antigen recognition. Thus, there is a need in the art for greater understanding of P2X receptors, as well as novel treatments for autoimmune related disorders, and development of more effective transplantation procedures.

BRIEF DESCRIPTION OF THE FIGURES

Exemplary embodiments are illustrated in referenced figures. It is intended that the embodiments and figures disclosed herein are to be considered illustrative rather than restrictive.

FIG. 2A). Recipient splenocytes re-challenged with donor splenocytes displayed fewer IFN-γ-producing cells (n=5, *$p<0.001$ vs. Untreated day 7; FIG. 2B) and IL-17$^+$CD4$^+$ T cells (n=5, *$p<0.05$ vs. Untreated day 7; FIG. 2D) was observed at days 7 and 100 in oATP-treated mice.

FIGS. 4A-4E demonstrate that, in accordance with an embodiment herein, oATP prolongs graft survival in a model of allogeneic islet transplantation (FIG. 4A). At day 14 after transplantation, reduced numbers of IFN-γ-producing cells (FIG. 4B) and Th17 cells (FIG. 4C) were observed in oATP-treated mice. RT-PCR revealed reduced T-bet transcripts (FIG. 4D). Rapamycin and oATP synergize and promote long-term graft survival in allogeneic islet transplantation (FIG. 4E). *$p<0.05$ vs. Untreated.

FIGS. 5A-5E demonstrate that, in accordance with an embodiment herein, in CD4$^+$ T-cells, 100 μM oATP suppressed anti-CD3-Ig and anti-CD28-Ig-mediated IFN-γ production (FIG. 5A) and proliferation (FIG. 5B). oATP prevented phosphorylation of STAT3 as assessed by Luminex (FIG. 5C) or WB (FIG. 5D). *$p<0.05$ vs. Control. Colivelin partially reverted the suppression of activation-induced IFN-γ production caused by oATP (FIG. 5E). *$p<0.05$ vs. Colivelin(−)/oATP(−); #$p<0.05$ vs. Colivelin(−)/oATP(+).

FIGS. 6A-6G demonstrate that, in accordance with an embodiment herein, 100 μM oATP inhibited the conversion of naïve Th0 cells into Th1 (FIGS. 6A, 6B) and Th17 cells (FIGS. 6C, 6D). Over-expression of P2X7R on Th0 cells was evident after P2X7R retroviral transduction (FIG. 6E). P2X7R-transduced Th0 cells displayed increased differentiation capacity into Th1 (FIG. 6F) or Th17 cells (FIG. 6G) compared to mock-transduced cells.*$p<0.05$ vs. Control.

FIGS. 10A-10E depict, in accordance with an embodiment herein, the putative 3D structure (FIG. 10A) and the sequence (FIG. 10B) (SEQ ID NO: 1) of the human P2X7R receptor. The non-bolded, non-italicized section represents the ectodomain (55 kDs) (FIG. 10C) (SEQ ID NO: 2) that was used to construct a trimeric fusion protein (FIG. 10D). The fusion protein has 2 trimers inserted on the Fc portion (FIG. 10E).

FIG. 11A depicts representative images of lung allografts (arrow) and histology (HE stain ×100) of untreated (Vehicle) and oATP treated recipients 15, 30, and 60 days after transplant. Untreated lung allografts show increasing disease severity resulting is fibrosis while oATP treated allografts have limited disease. FIG. 11B depicts graphs illustrating PawP and ACR grade of vehicle and oATP treated lung allografts 15, 30, and >60 days after transplant. Treated allografts were significantly improved as compared to vehicle treated for each time point (P<0.05, N=≥6 for each). The >60 day ACR grade for vehicle treated allografts were graded as A4 although all grafts showed severe fibrosis. FIG. 11C depicts representative microCT thoracic images showing the lung allografts (arrow) 15, 30, and 60 days following transplantation. Vehicle treated grafts demonstrated consolidation and volume loss (60 days) while treated allografts showed less disease. FIG. 11D depicts a graph illustrating ATP levels from BAL of untreated transplanted lungs (vehicle control) and oATP treated lung 15 days post transplant, P<0.05 for untreated compared to oATP treated N=4/group).

FIG. 13A depicts a graph illustrating the relative amount of inflammation (score 0-4) for both vehicle and oATP treated allografts for 15, 30, and >60 days. (P<0.5 for oATP treated as compared to untreated, N=≥6 per group, the ≥60 day oATP was compared to 30 day untreated since allografts at this time point demonstrate severe fibrosis with varying degrees of inflammation. FIG. 13B depicts graphs illustrating the number of leucocytes, lymphocytes, CD4+ and CD8+ cells from isolated lung allografts (day 15) with and without oATP based on flow cytometry. Treated allografts had significantly fewer inflammatory cells has compared to untreated allografts. FIG. 13C depicts a representative example of flow cytometry analysis for CD4 and CD8 cells from both vehicle and oATP treated lung allografts. FIG. 13D depicts graphs showing the number of Th17 (IL-17+) and Treg (CD4+CD25+Foxp3+) from lung allografts 15 days after transplant with oATP treated samples having fewer Th17 and Treg as compared to untreated allografts, # P<0.05 treated to untreated. Graphs illustrating the percentage of Treg from untransplanted lungs (baseline), oATP treated and untreated recipient lungs and spleens for the three time points after transplant, P<0.05 for allografts as compared to baseline (*), N≥6 per group.

FIG. 15A depicts graphs illustrating the number of positive cells (ELISPOT) isolated from untransplanted lungs, lung allografts and recipient spleens for IFN-γ and IL-4 at the indicated time points (15, 30 and ≥60 days). N=5 for IFN-γ and N=3 or 4 for IL-4. P<0.05 for vehicle treated as compared to oATP treated samples (*). The ≥60 day lung allograft had severe fibrosis and cells could not be isolated for this experimental condition so oATP treated was compared to the earlier time points with P<0.05 (#). FIG. 15B depicts representative flow cytometry analysis of isolated lung CD8+ T cells for CD62L and CD44 expression from both treated and untreated allografts. Graphs illustrating the percentage of effector memory cells (Tem), $CD44^{hi}CD62L^{lo}$ from untransplanted mouse lung and spleens, and both vehicle and oATP treated allografts and recipient spleens showing a significant reduction of lung CD8 Tem at 15 and ≥60 days and for CD4 Tem after 15 days. (N=≥4 per experimental group * P<0.05 for treated versus untreated samples). FIG. 15C depicts a graph illustrating the percentage of isolated cells that are CD8+CD44+CD62L+CCR7+ representative of CD8 Tem which are significantly (*P<0.05) increased in oATP treated samples as compared to untreated, N=5 per group.

FIG. 16A depicts a graph of CD8 activation levels. To better assess the response of CD8 T cells, splenocytes isolated from OT1 mice were stimulated with OVA peptide with and without (positive control) oATP (100 μM) and T cell proliferation determined. Treated samples showed a significant reduction in activation as compared to untreated samples (N=3 P<0.05). FIG. 16B depicts a representative of four experiments showing flow cytometry analysis of isolated mouse CD8 T cells stimulated with anti-CD3 (10 μg/ml 2C-11 antibody) using coated plates and evaluated for Th1 cytokines, TNF-α and IFN-γ, and the cytolytic protein granzyme B expression with impaired activation of CD8 cells with oATP treatment. FIG. 16C depicts photomicroscopy images and a graph of cell growth and survival. Freshly isolated human peripheral blood mononuclear cells (PBMCs, 4×10$^5$/ml) were applied onto pre-seeded A549 cells (at ~20% confluency). Cells were cultured in RPMI medium supplemented with interferon gamma (IFNγ) with or without oATP for 7 days. Shown are representative images of A549 cells, and A549 cells co-cultured with PBMCs in the presence and absence of 200 μM oATP. Images were taken on day 7 of the co-culture. Graph illustrating the effects of various concentrations of oATP on PBMC dependent A549 cell growth and survival. The A549 cell counts under each condition were normalized to that of the A549 cells cultured in the absence of PBMC (n=4, mean±S.E.M.).

Figure 17:
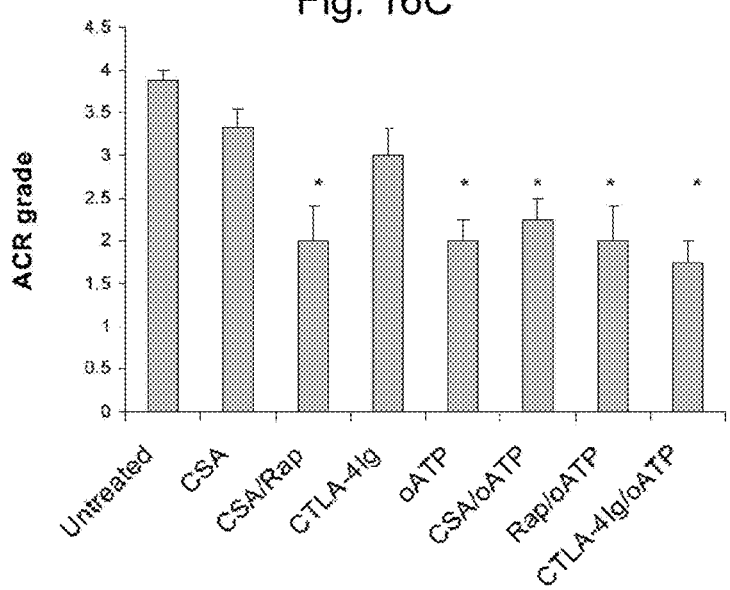

FIG. 17 depicts cyclosporine, rapamycin, and oATP treated lung allografts outcomes. Graph illustrating the ACR grade of mouse lung allografts (30 days) from untreated recipients and recipients receiving CSA (10 mg/kg/day), CTLA-4Ig (250 μg on days 0, 1, 2, 4 and 6), oATP 250 μg/day, and/or Rap (0.1 mg/kg/day) from day 0 to 30. This represents ≥5 transplants per group with P<0.05* as compared to untreated allografts.

Figures 18A, 18B, 18C:
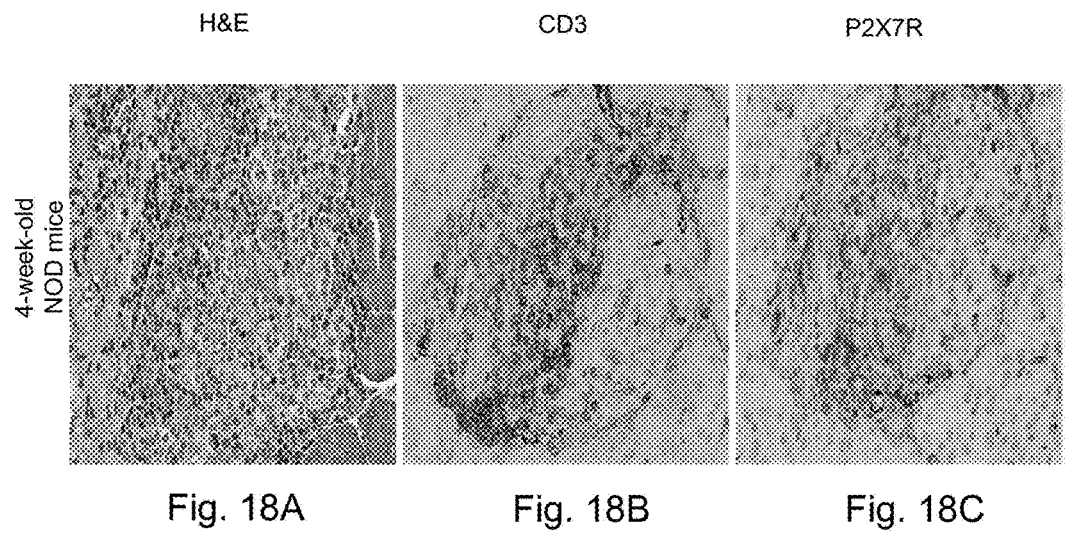
Figure 18D:
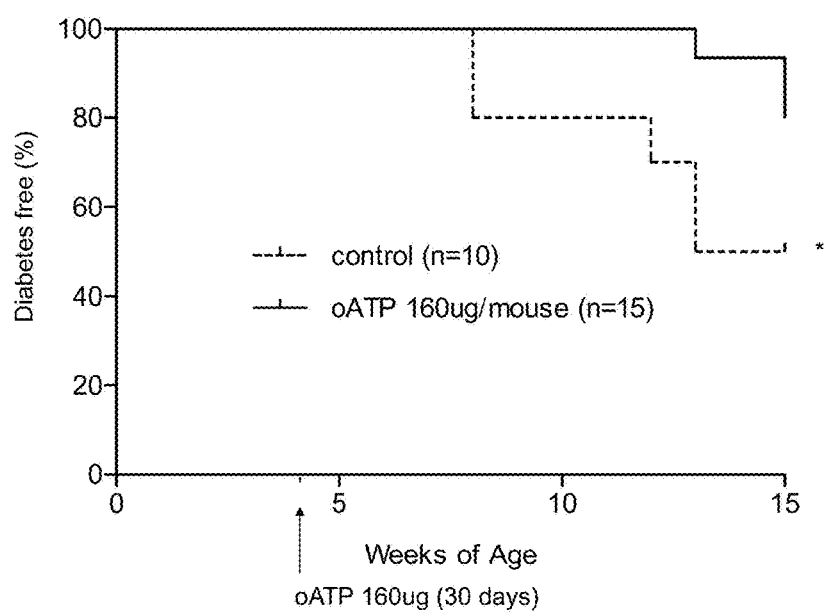
Figure 18E:
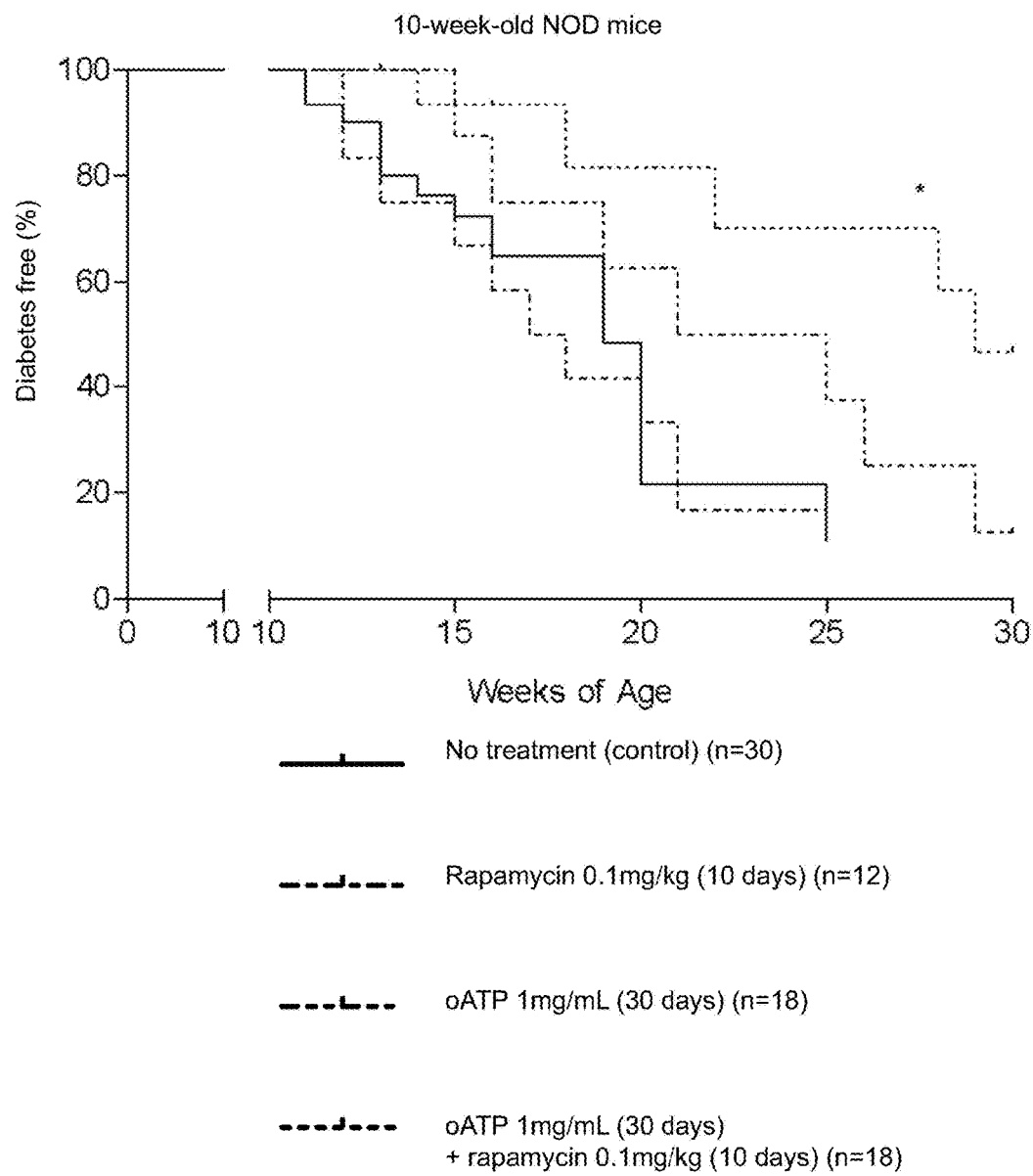

FIGS. 18A-18E demonstrate the progression of diabetes. Islets from 4-week-old NOD mice showed moderate infiltrate (FIG. 18A), mainly consisting of CD3+ cells (FIG. 18B), which appeared to be P2X7R+(FIG. 18C). Graphs demonstrate that ATP/P2X7R targeting with oATP (administered daily i.p. for 30 days) delays diabetes onset in 4-week-old NOD mice alone (early prevention study, FIG. 18D) and in 10-week-old NOD mice when associated with Rapamycin (late prevention study, FIG. 18E).

Figure 19A:
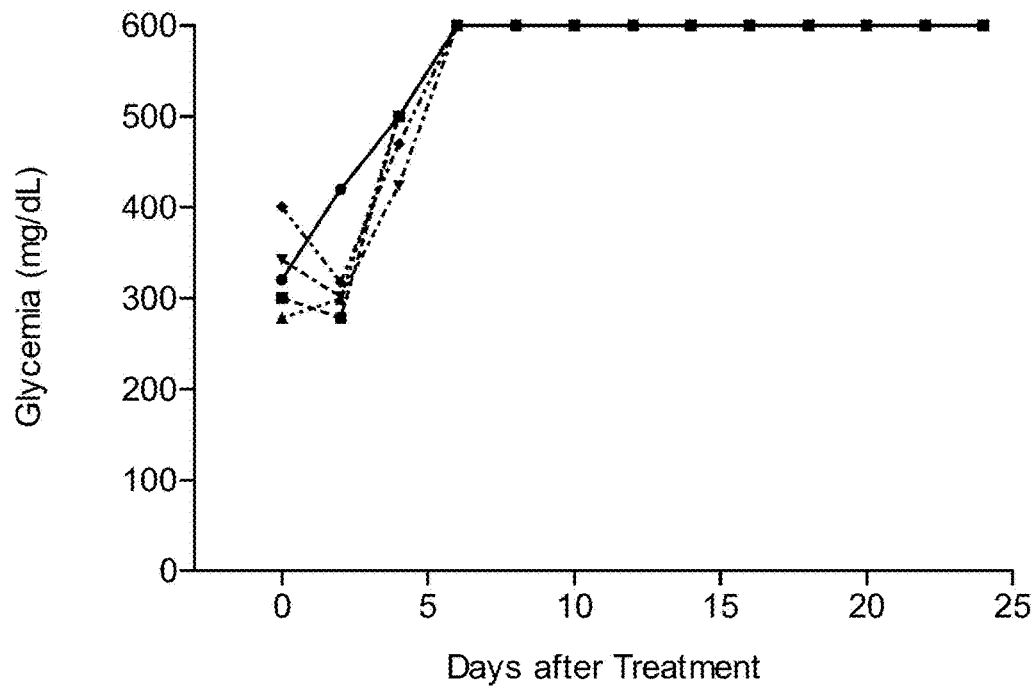
Figure 19B:
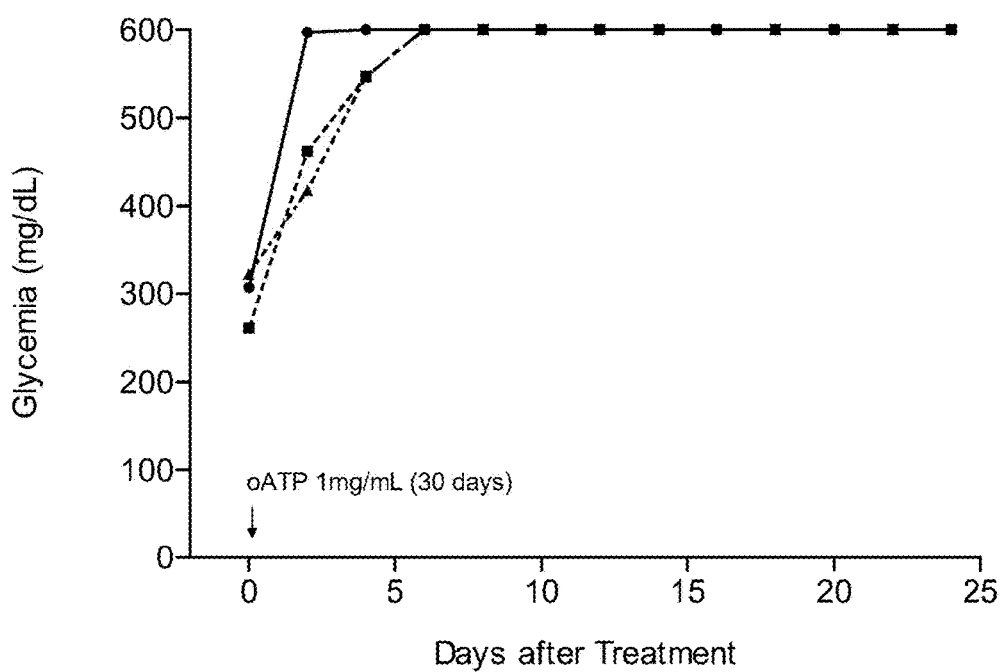
Figure 19C:
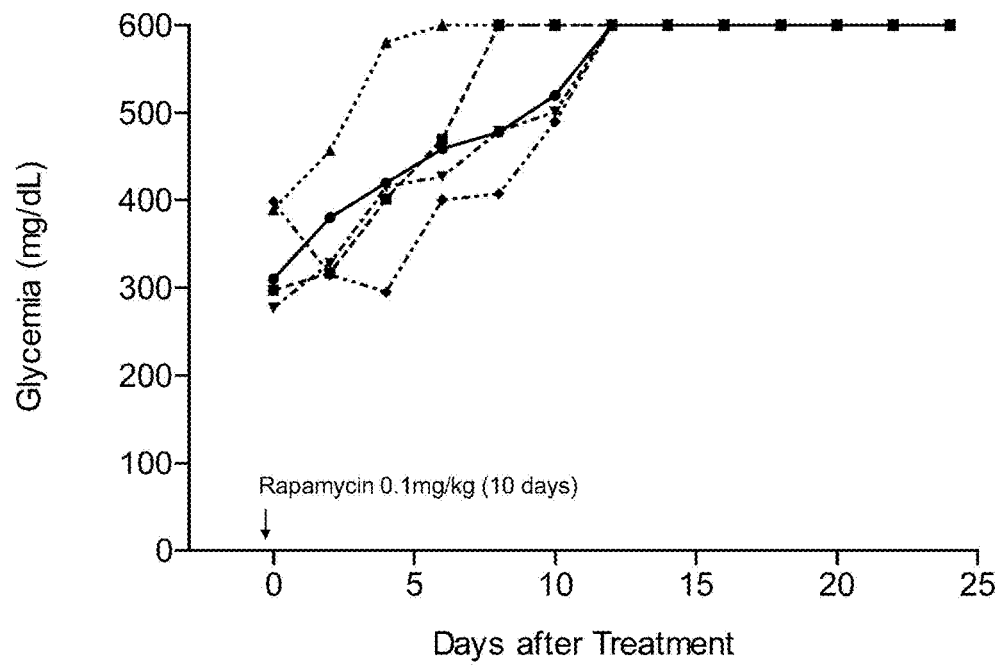
Figure 19D:
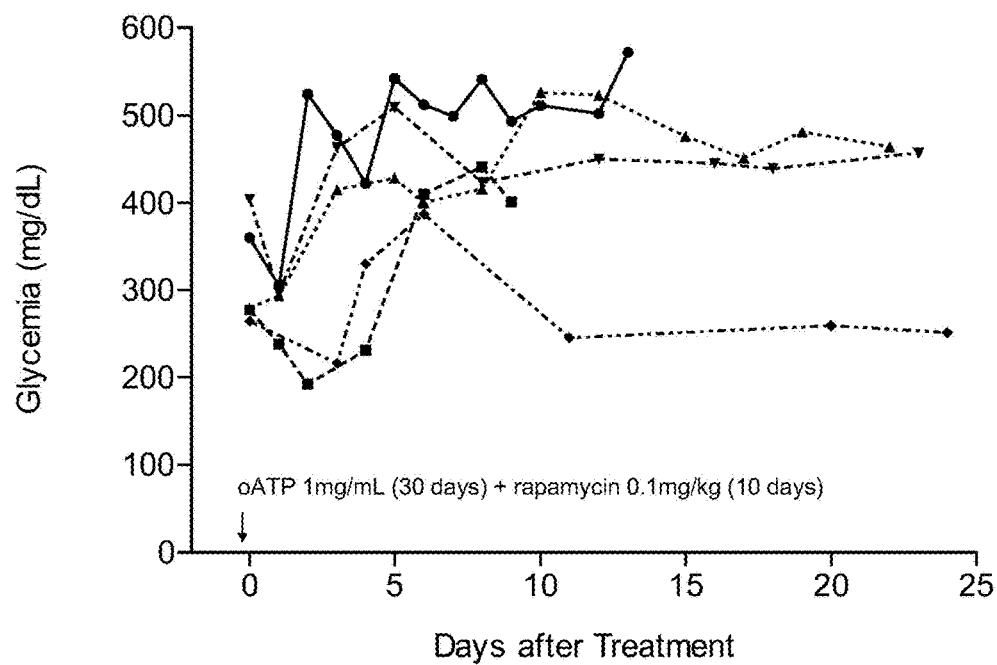
Figure 19E:
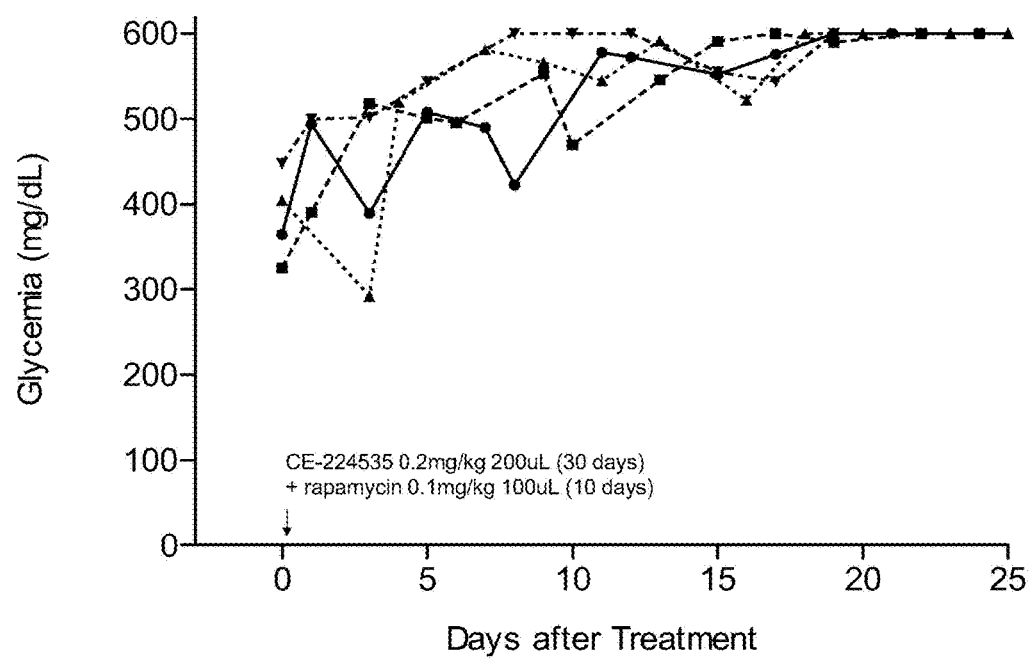

FIGS. 19A-19E depict graphs demonstrating reversal of experimental diabetes and hyperglycemia in NOD mice untreated (FIG. 19A), treated with oATP (FIG. 19B), Rapamycin (FIG. 19C), Rapamycin plus oATP (FIG. 19D) and Rapamycin plus CE-224535 (FIG. 19E).

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, "treatment" or "treating" should be understood to include any indicia of success in the treatment, alleviation or amelioration of an injury, pathology or condition. This may include parameters such as abatement, remission, diminishing of symptoms, slowing in the rate of degeneration or decline, making the final point of degeneration less debilitating; improving a patient's physical or mental well-being; or, preventing the onset of disease.

As used herein, the term "diabetes" refers a syndrome of disordered metabolism, usually due to a combination of hereditary and environmental causes, resulting in abnormally high blood sugar levels (hyperglycemia). The two most common forms of diabetes are due to either a diminished production of insulin (in type 1), or diminished response by the body to insulin (in type 2 and gestational). As used throughout, "diabetes" includes Type 1, Type 2, Type 3, and Type 4 diabetes unless otherwise specified herein. Both type 1 and type 2 diabetes lead to hyperglycemia, which largely causes the acute signs of diabetes: excessive urine production, resulting compensatory thirst and increased fluid intake, blurred vision, unexplained weight loss, lethargy, and changes in energy metabolism. Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation. In some embodiments, the diabetes can be type 1 diabetes. In some embodiments, a subject can be pre-diabetic, or susceptible to developing diabetes which can be characterized, for example, as having elevated fasting blood sugar, elevated post-prandial blood sugar, a family history of diabetes, impaired glucose tolerance, and/or impaired fasting glycaemia.

As disclosed herein, during the onset of type 1 diabetes (T1D), T cells are fully activated at the immune synapse (IS) between pancreatic islets and T cells when autoantigens are presented by the TCR-MHC complex in the presence of an IL-2 signal and costimulation; however, other signals (e.g. inflammation) play a role in this process. The purine adenosine 5'-triphosphate (ATP), released during cell damage/inflammation, is sensed by the ionotropic purinergic P2X7 receptor (P2X7R), which is expressed primarily, though not exclusively, on lymphocytes, thus regulating T cell activation and constituting an "autocrine alerting system". In accordance with various embodiments herein, the inventors demonstrated in vivo that P2X7R targeting promoted islet graft survival, delayed diabetes onset, and induced donor-specific hyporesponsiveness. Additionally, in accordance with various embodiments herein, the inventors demonstrated in humans that P2X7R expression is increased in those with diabetes, and that P2X7R targeting with the human P2X7R antagonist CE-224535 inhibits allo- and autoimmune responses. As further disclosed herein, their results include in vitro data demonstrating that ATP promotes P2X7R expression on naïve T cells, P2X7R is upregulated in vitro during Th1 and Th17 differentiation, P2X7R genetic upregulation promotes Th1 and Th17 differentiation by activating ROR-γ and T-bet. In vivo results include P2X7R upregulated in the islet graft, P2X7R targeting promotes islet graft survival, P2X7R targeting delays diabetes onset in NOD mice, P2X7R targeting induces donor-specific hyporesponsiveness, and P2X7R targeting reduces intra-graft T-bet expression. In human subjects, the inventors found P2X7R expression increased in T cells obtained from individuals with T1D, as well as P2X7R targeting with the human P2X7R antagonist CE-224535 resulted in inhibition of allo- and autoimmune responses ex vivo.

In one embodiment, the present invention provides a method of treating type 1 diabetes in a subject, comprising providing an inhibitor of ATP signaling, and administering a therapeutically effective dosage of the inhibitor to the subject. In another embodiment, the inhibitor is a P2X7R signaling inhibitor. In another embodiment, the inhibitor is a P2X7R-Ig fusion protein. In another embodiment, the inhibitor is a P2X7R soluble protein. In another embodiment, the inhibitor is a P2XR soluble protein. In another embodiment, the inhibitor is a purinergic receptor inhibitor. In another embodiment, the inhibitor is CE-224535, AZD9056, GSK1482160, or oATP. In another embodiment, the inhibitor is an exogenous inhibitor of ATP in beta cells.

In another embodiment, the inhibitor is an ATPase on a cell surface. In another embodiment, the cell is a T cell, nerve, dendritic or cardiomyocyte cell. In another embodiment, the subject is human. In another embodiment, the subject is a mouse or rat. In another embodiment, the inhibitor degrades ATP.

In another embodiment, the present invention provides a method of slowing progression of diabetes, comprising providing a composition comprising an inhibitor of ATP, and administering the composition to a subject diagnosed with diabetes. In another embodiment, the inhibitor is a P2X7R signaling inhibitor. In another embodiment, the inhibitor is a P2X7R-Ig fusion protein. In another embodiment, the inhibitor is CE-224535, AZD9056, GSK1482160, or oATP. In another embodiment, the inhibitor is an exogenous inhibitor of ATP in beta cells. In another embodiment, the inhibitor is an ATPase on a cell surface. In another embodiment, the cell is a T cell, nerve, dendritic or cardiomyocyte cell. In another embodiment, the subject is human.

In another embodiment, the present invention provides a method of treating diabetes in a subject, comprising providing an inhibitor of ATP, and administering a therapeutically effective dosage of the inhibitor to the subject. In another embodiment, the inhibitor of ATP is oATP.

In another embodiment, the present invention provides a method of preventing diabetes in a subject, comprising providing an inhibitor of ATP signaling, and administering a therapeutically effective dosage of the inhibitor to the subject. In another embodiment, the subject is diagnosed as susceptible to diabetes.

Described herein are methods for suppressing graft rejection in a subject. Suppressing a graft rejection can refer to preventing one or more symptoms of rejection, decreasing one or more symptoms of rejection, reducing the need for other immune system inhibitors to be administered to the subject, and/or increasing the extent and/or time of graft success. The graft can be a tissue graft and/or an organ transplantation.

In one embodiment, the present invention provides a method of delaying rejection of a transplanted organ in an individual, comprising providing an inhibitor of ATP signaling, and administer an effective dosage of the inhibitor to the individual, where the individual has previously received a transplant organ. In another embodiment, the inhibitor is a P2X7R-Ig fusion protein. In another embodiment, the inhibitor is CE-224535, AZD9056, GSK1482160, or oATP. In another embodiment, the inhibitor is a purinergic receptor signaling inhibitor.

In another embodiment the present invention provides a method of delaying rejection of a transplanted organ in an individual, comprising providing an inhibitor of ATP signaling, and administering an effective dosage of the inhibitor to an individual before receiving a transplant organ. In another embodiment, the inhibitor is a P2X7R-Ig fusion protein. In another embodiment, the inhibitor is CE-224535, AZD9056, GSK1482160, or oATP. In another embodiment, the inhibitor is a P2X7R signaling inhibitor.

In another embodiment, the present invention provides a method of preventing and/or decreasing the extent of rejection and/or treating rejection of a graft in a subject, comprising providing an inhibitor of ATP signaling, and administering a therapeutically effective dosage of the inhibitor to the subject. In another embodiment, the inhibitor of ATP signaling is a P2X7R fusion protein.

As further disclosed herein, the inventors addressed the effect of oATP treatment in a model of allogeneic orthotropic left lung transplantation. At the end of the treatment radiological and histological analysis demonstrated reversal of graft rejection and no signs of fibrosis. In one embodiment, the present invention provides a method of preventing and/or treating lung fibrosis in a subject, comprising providing an inhibitor of ATP signaling, and administering a therapeutically effective dosage of the inhibitor to the subject. In another embodiment, the inhibitor of ATP signaling is an inhibitor of ATP. In another embodiment, the inhibitor of ATP signaling is a soluble P2XR fusion protein.

As used herein, the term "inhibitor" refers to an agent which can decrease the expression and/or activity of the target (e.g. ATP signaling), e.g. by at least 10% or more, e.g. by 10% or more, 50% or more, 70% or more, 80% or more, 90% or more, 95% or more, or 98% or more. The efficacy of an inhibitor of, for example, ATP signaling, e.g. its ability to decrease the level and/or activity of ATP signaling, can be determined, e.g. by measuring the level of phosphorylated STAT3, Th1 or Th17 differentiation, and/or CD4+ proliferation as described in the Examples herein. Methods for measuring the level of, e.g. ATP signaling, a specific molecule (e.g. ATP), and/or a given mRNA and/or polypeptide are known to one of skill in the art, e.g. RTPCR can be used to determine the level of RNA and Western blotting with an antibody can be used to determine the level of a polypeptide.

In some embodiments, the inhibitor can be an inhibitory nucleic acid; an aptamer; an antibody reagent; an antibody; or a small molecule. In some embodiments, the inhibitor of a target can be an inhibitor specific for that target. An inhibitor specific for a given target can be an inhibitor which binds specifically to the target molecule.

In some embodiments, an inhibitor of a gene expression product of a gene described herein can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of the targeted mRNA transcript. The use of these iRNAs permits the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of, a targeted mRNA. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.), 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

In some embodiments, an inhibitory nucleic acid can comprise a modified backbone. Representative U.S. patents that teach the preparation of modified phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference. Representative U.S. patents that teach the preparation of additional backbone modifications include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In some embodiments, an inhibitory nucleic acid can be a PNA. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

In some embodiments, inhibitory nucleic acids can comprise one or more substituted sugar moieties. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference. In some embodiments, inhibitory nucleic acids can comprise one or more substituted nucleobases, e.g. as described in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. I., ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. Representative U.S. patents that teach the preparation of certain modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750, 692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA as described herein involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to e.g., P2X7R.

In some embodiments, an inhibitor will directly bind to the targeted factor, e.g. to ATP or a given target mRNA. In some embodiments, an inhibitor will directly result in the cleavage of the targeted factor's mRNA, e.g., via RNA interference. In some embodiments, an inhibitor can act in a competitive manner to inhibit activity of the targeted factor. In some embodiments, an inhibitor can comprise a portion of the target factor and act as a competitive or dominant negative factor for interactions normally involving the targeted factor.

As used herein, "ATP signaling" refers to the specific binding of cell surface receptors to extracellular ATP and the downstream events triggered by that recognition. In some embodiments, ATP signaling refers to the process of a P2X7R receptor binding to ATP and the downstream events of, e.g., phosphorylation of STAT3, Th1 and Th17 differentiation, and CD4+ proliferation and IFN-γ production.

In some embodiments, an inhibitor of ATP signaling, e.g., an inhibitor of ATP can be an inhibitor that is exogenous to beta cells. In some embodiments, an inhibitor of ATP signaling, e.g., an inhibitor of ATP can be an inhibitor that is ectopic to beta cells. The term "exogenous" refers to a substance present in a cell other than its native source. A substance will be considered exogenous if it is introduced into a cell or an ancestor of the cell from which the cell has inherited the substance. In contrast, the term "endogenous" refers to a substance that is native to the biological system or cell (e.g. the microbial cell and/or target cell). As used herein, "ectopic" refers to a substance that is found in an unusual location and/or amount. An ectopic substance can be one that is normally found in a given cell, but at a much lower amount and/or at a different time.

In some embodiments, an inhibitor of ATP signaling (e.g. an inhibitor of ATP) can be an ATPase. A variety of ATPases are known in the art. By way of non-limiting example, ATPases include V-ATPases, P-ATPases, and E-ATPases. In some embodiments, the ATPase can be an E-ATPase. In some embodiments, the E-ATPase can be a plasma membrane protein. In some embodiments, the E-ATPase can be a soluble E-ATPase. In some embodiments, the ATPase can be located on a cell surface, e.g. it can be a transmembrane protein capable of hydrolysis of extracellular ATP or it can be an extracellular protein bound to the cell surface.

In some embodiments, an inhibitor of ATP signaling can be a purinergic receptor inhibitor. Purinergic receptors are plasma membrane molecules that detect the presence of ATP, adenosine, and related molecules in the extracellular environment (e.g. ADP, UTP, and UDP) and transmit a signal to the cytoplasm. P1 and P2Y purinergic receptors are G protein-coupler receptors, while P2X purinergic receptors are ligand-gated ion channels. In some embodiments, the purinergic receptor inhibitor can be a P2X receptor inhibitor. In some embodiments, the purinergic receptor inhibitor can be a P2X7 receptor inhibitor. Non-limiting examples of P2X7 purinergic receptor inhibitors include GSK1482160; CE-224535; AZD9056; GSK1482160; and oATP.

"P2X7R signaling" refers to the process of activation of P2X7R and the downstream signaling events as described herein, e.g., the phosphorylation of STAT3, Th1 and Th17 differentiation, and CD4+ proliferation and IFN-γ production. As used herein "P2X7R" refers to polypeptide that forms a homomeric trimeric P2X7 receptor, which is a ligand-gated cation channel that opens in response to ATP binding and causes depolarization of the cell. P2X7R is also referred to as P2RX7 and P2X7. The sequences of P2X7R for a number of species are known in the art, e.g., human P2X7R (NCBI Gene ID No: 5027; mRNA (NCBI Ref Seq: NM 002562, SEQ ID NO: 3); polypeptide (NCBI Ref Seq: NP_002553, SEQ ID NO: 4).

Figure 10A:
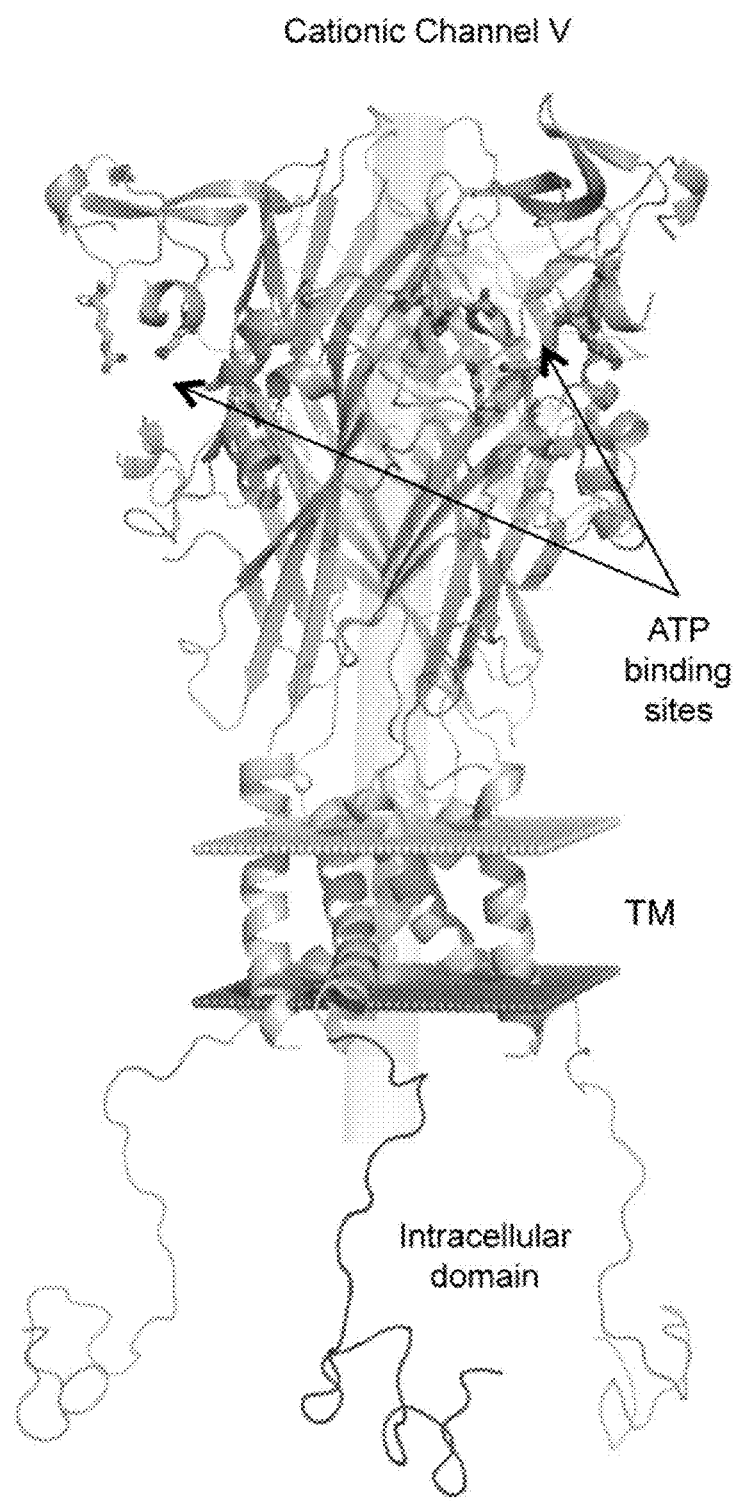
Figure 10E:
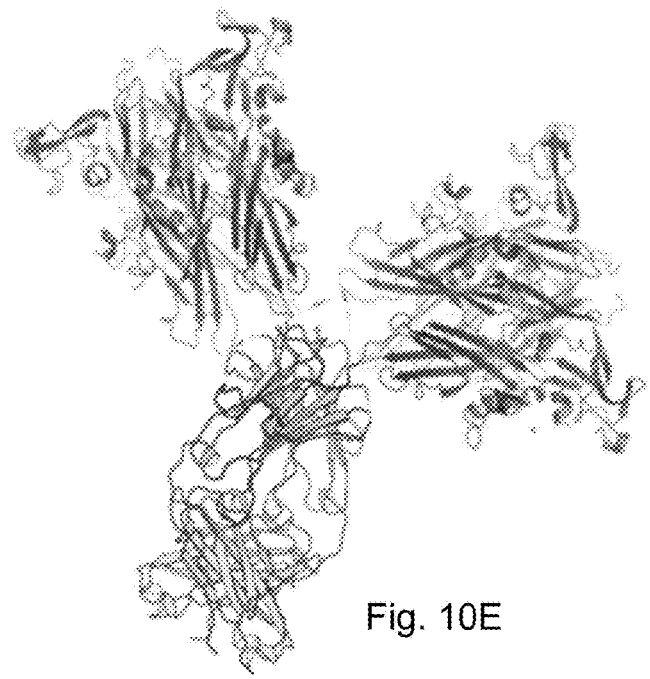

As used herein "soluble P2X7R polypeptide" refers to a P2X7R polypeptide comprising at least one extracellular portion of P2X7R and not comprising a transmembrane domain. In some embodiments, a soluble P2X7R polypeptide can comprise a polypeptide having the sequence of SEQ ID NO: 2. In some embodiments, a soluble P2X7R polypeptide can comprise repeats of an extracellular portion of P2X7R, e.g. two copies of an extracellular portion of P2X7R, three copies of an extracellular portion of P2X7R, or more copies of an extracellular portion of P2X7R, e.g. as depicted in FIG. 10D. In some embodiments, a soluble P2X7R polypeptide can be a fusion polypeptide.

As further described in FIGS. 10A-10E herein, the inventors prepared a soluble P2X7R-Ig fusion protein. In one embodiment, a soluble P2X7R-Ig fusion protein may be used to quench circulating ATP. In another embodiment, the soluble P2X7R-Ig fusion protein may be used as a therapeutic for diabetes, autoimmunity diseases, and/or inflammatory diseases. In another embodiment, the soluble P2X7R-Ig fusion protein may be used in conjunction with transplantation procedures. In another embodiment, the soluble P2X7R-Ig fusion protein may be used for preventing and/or treating lung fibrosis. In one embodiment, the present invention is a composition comprising a P2X7R-Ig fusion protein, and an acceptable carrier. In another embodiment, the P2X7R-Ig fusion protein is a soluble protein with the ectodomain of a P2X7R receptor is bound to the Fc portion of an IgG molecule.

As used herein, the term "fusion protein" or "fusion polypeptide" refers to a protein created by joining two genes or two proteins/peptides together. In the laboratory, this can be achieved through the creation of a fusion gene which is done through the removal of the stop codon from a DNA sequence of the first protein and then attaching the DNA sequence of the second protein in frame. The resulting DNA sequence can then be expressed by a cell as a single protein. In a fusion protein, the two proteins can be joined together with a linker or spacer peptide added between the two proteins.

In another embodiment, the present invention is a composition comprising a P2XR soluble protein, and an acceptable carrier. In another embodiment, the P2XR soluble protein is monomeric. In another embodiment, the P2XR soluble protein is dimeric. In another embodiment, the P2XR soluble protein is trimeric. In another embodiment, the present invention is a fusion protein having the sequence of the P2X7R-Ig fusion protein described in FIG. 10B herein.

An example of a P2XR peptide sequence that may be incorporated in the various pharmaceutical compositions of the present invention are described herein in FIG. 10B. In one embodiment, the P2XR peptide sequence has at least 70% identity with respect to the amino acid sequences set forth in FIG. 10B. In another embodiment, the P2XR peptide sequence has at least 80%, 90%, 95%, 96%, 97%, 98% or 99% identity, with respect to the amino acid sequence set forth in FIG. 10B.

In various embodiments, the present invention provides compositions including a acceptable excipient along with a therapeutically effective amount of an P2X receptor inhibitor or ATP inhibitor. "Acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The compositions according to the invention can also contain any pharmaceutically acceptable carrier. "Acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective an P2X receptor inhibitor or ATP inhibitor can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., diabetes. A subject can be male or female.

A subject can be one who has been previously diagnosed with or identified as suffering from or having a condition in need of treatment (e.g. diabetes) or one or more complications related to such a condition, and optionally, have already undergone treatment for diabetes or the one or more complications related to diabetes. Alternatively, a subject can also be one who has not been previously diagnosed as having diabetes or one or more complications related to diabetes. For example, a subject can be one who exhibits one or more risk factors for diabetes or one or more complications related to diabetes or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, a given "polypeptide", e.g. a P2X7R polypeptide, can include the human polypeptide as well as homologs from other species, including but not limited to bovine, dog, cat chicken, murine, rat, porcine, ovine, turkey, horse, fish, baboon and other primates. The terms also refer to fragments or variants of the wild-type polypeptide that maintain at least 50% of the activity or effect, of the full length wild-type polypeptide. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of allograft rejection as described herein.

In some embodiments, a polypeptide, e.g., a PX27R polypeptide, can be a variant of a sequence described herein. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of the wildtype polypeptide, e.g. 110%, 125%, 150%, 175%, 200%, 500%, 1000% or more.

One method of identifying amino acid residues which can be substituted is to align, for example, human polypeptide to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking Conversely, cysteine bond(s) can be added to the polypeptide to improve its stability or facilitate oligomerization.

In some embodiments, a polypeptide can comprise one or more amino acid substitutions or modifications. In some embodiments, the substitutions and/or modifications can prevent or reduce proteolytic degradation and/or prolong half-life of the polypeptide in the subject or cell. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

In some embodiments, a polypeptide can be a functional fragment of one of the amino acid sequences described herein. As used herein, a "functional fragment" is a fragment or segment of a polypeptide which retains at least 50%, at least 60%, at least 70%, at least 80%, at least 90% or more of the activity of the wildtype polypeptide, e.g., in any of the assays described herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. diabetes. The term "treating" includes reducing or alleviating at least one adverse effect or symptom of a condition, disease or disorder associated with, e.g., diabetes. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

Some embodiments of the technology described herein can be defined according to any of the following numbered paragraphs:

1) A method of treating diabetes in a subject, comprising:
providing an inhibitor of ATP signaling; and
administering a therapeutically effective dosage of the inhibitor to the subject.

2) A method of treating diabetes in a subject, comprising:
administering a therapeutically effective dosage of an ATP signaling inhibitor to the subject.

3) A method of slowing progression of diabetes, comprising:
providing a composition comprising an inhibitor of ATP signaling; and
administering the composition to a subject diagnosed with diabetes.

4) A method of slowing progression of diabetes, comprising:
administering an inhibitor of ATP signaling to a subject diagnosed with diabetes.

5) A method of preventing diabetes in a subject, comprising:
providing an inhibitor of ATP signaling; and
administering a therapeutically effective dosage of the inhibitor to the subject.

6) A method of preventing diabetes in a subject, the method comprising administering a therapeutically effective dosage of an inhibitor of ATP signaling to the subject.

7) The method of any of paragraphs 5-6, wherein the subject is diagnosed as susceptible to diabetes.

8) The method of any of paragraphs 1-7, wherein the diabetes is type 1 diabetes.

9) A method of delaying rejection of a transplanted organ in an individual, comprising:
providing an inhibitor of ATP signaling;
administering an effective dosage of the inhibitor to the individual,
wherein the individual has previously received a transplant organ.

10) A method of suppressing rejection of a transplanted organ in an individual who has received a transplanted organ, the method comprising:
administering a therapeutically effective dose of an inhibitor of ATP signaling to the individual.

11) A method of delaying rejection of a transplanted organ in an individual, comprising:
providing an inhibitor of ATP signaling;
administering an effective dosage of the inhibitor to an individual before receiving a transplant organ.

12) A method of suppressing rejection of a transplanted organ in an individual, the method comprising administering a therapeutically effective dosage of an inhibitor of ATP signaling before or during the transplantation of the organ to the individual.

13) A method of preventing and/or treating lung fibrosis in a subject, comprising:
providing an inhibitor of ATP signaling; and
administering a therapeutically effective dosage of the inhibitor to the subject.

14) A method of treating lung fibrosis in a subject, the method comprising administering a therapeutically effective dosage of an inhibitor of ATP signaling to the subject.

15) A method of preventing and/or decreasing the extent of rejection and/or revert rejection of a graft in a subject, comprising:
providing an inhibitor of ATP signaling; and
administering a therapeutically effective dosage of the inhibitor to the subject.

16) A method of suppressing graft rejection in a subject, the method comprising administering a therapeutically effective dosage of an inhibitor of ATP signaling to the subject.

17) The method of any of paragraphs 1-16, wherein the inhibitor is a P2X7R signaling inhibitor.

18) The method of any of paragraphs 1-17, wherein the inhibitor is a P2X7R-Ig fusion protein.

19) The method of any of paragraphs 1-18, wherein the inhibitor is a P2X7R soluble protein.

20) The method of any of paragraphs 1-19, wherein the inhibitor is a P2XR soluble protein.

21) The method of any of paragraphs 1-20, wherein the inhibitor is a purinergic receptor inhibitor.

22) The method of any of paragraphs 1-21, wherein the inhibitor of ATP signaling is an inhibitor of ATP.

23) The method of any of paragraphs 1-22, wherein the inhibitor is CE-224535, AZD9056, GSK1482160, or oATP.

24) The method of any of paragraphs 1-23, wherein the inhibitor is an inhibitor of ATP exogenous to beta cells.

25) The method of any of paragraphs 1-24, wherein the inhibitor is an ATPase on a cell surface.

26) The method of paragraph 25, wherein the cell is a T cell, nerve, dendritic or cardiomyocyte cell.

27) The method of any of paragraphs 1-26, wherein the subject is human.

28) The method of any of paragraphs 1-27, wherein the subject is a mouse or rat.

29) The method of any of paragraphs 1-28, wherein the inhibitor degrades ATP.

30) A composition, comprising:
a P2X7R-Ig fusion protein; and
a pharmaceutically acceptable carrier.

31) The composition of paragraph 30, wherein the P2X7R-Ig fusion protein is a soluble protein with the ectodomain of a P2X7R receptor bound to the Fc portion of an IgG molecule.

32) A composition, comprising:
a P2XR soluble protein; and
an acceptable carrier.

33) The composition of paragraph 32, wherein the P2XR soluble protein is monomeric.

34) The composition of paragraph 32, wherein the P2XR soluble protein is dimeric.

35) The composition of paragraph 32, wherein the P2XR soluble protein is trimeric.

36) A fusion protein having the sequence of SEQ. ID. NO.: 1 (wherein SEQ. ID. NO.: 1 is the sequence of P2X7R-Ig fusion protein).

37) The use of an inhibitor of ATP signaling to treat diabetes in a subject, the use comprising administering a therapeutically effective dosage of an ATP signaling inhibitor to the subject.

38) The use of an inhibitor of ATP signaling to slow the progression of diabetes in a subject, the use comprising administering a therapeutically effective dosage of an ATP signaling inhibitor to the subject.

39) The use of an inhibitor of ATP signaling to prevent diabetes in a subject, the use comprising administering a therapeutically effective dosage of an ATP signaling inhibitor to the subject.

40) The use of paragraph 39, wherein the subject is diagnosed as susceptible to diabetes.

41) The use of any of paragraphs 37-40, wherein the diabetes is type 1 diabetes.

42) The use of an inhibitor of ATP signaling to suppress rejection of a transplanted organ in a subject, the use comprising administering a therapeutically effective dosage of an ATP signaling inhibitor to the subject.

43) The use of paragraph 42, wherein the inhibitor is administered after a transplantation has occurred.

44) The use of paragraph 42, wherein the inhibitor is administered before or during the transplantation.

45) The use of an inhibitor of ATP signaling to suppress rejection of a graft in a subject, the use comprising administering a therapeutically effective dosage of an ATP signaling inhibitor to the subject.

46) The use of an inhibitor of ATP signaling to prevent or treating lung fibrosis in a subject, the use comprising administering a therapeutically effective dosage of an ATP signaling inhibitor to the subject.

47) The use of any of paragraphs 37-46, wherein the inhibitor is a P2X7R signaling inhibitor.

48) The use of any of paragraphs 37-47, wherein the inhibitor is a P2X7R-Ig fusion protein.

49) The use of any of paragraphs 37-48, wherein the inhibitor is a P2X7R soluble protein.

50) The use of any of paragraphs 37-49, wherein the inhibitor is a P2XR soluble protein.

51) The use of any of paragraphs 37-50, wherein the inhibitor is a purinergic receptor inhibitor.

52) The use of any of paragraphs 37-51, wherein the inhibitor of ATP signaling is an inhibitor of ATP.

53) The use of any of paragraphs 37-52, wherein the inhibitor is CE-224535, AZD9056, GSK1482160, or oATP.

54) The use of any of paragraphs 37-53, wherein the inhibitor is an inhibitor of ATP exogenous to beta cells.

55) The use of any of paragraphs 37-54, wherein the inhibitor is an ATPase on a cell surface.

56) The use of paragraph 25, wherein the cell is a T cell, nerve, dendritic or cardiomyocyte cell.

57) The use of any of paragraphs 37-55, wherein the subject is human.

58) The use of any of paragraphs 37-56, wherein the subject is a mouse or rat.

59) The use of any of paragraphs 37-57, wherein the inhibitor degrades ATP.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Figure 1A:
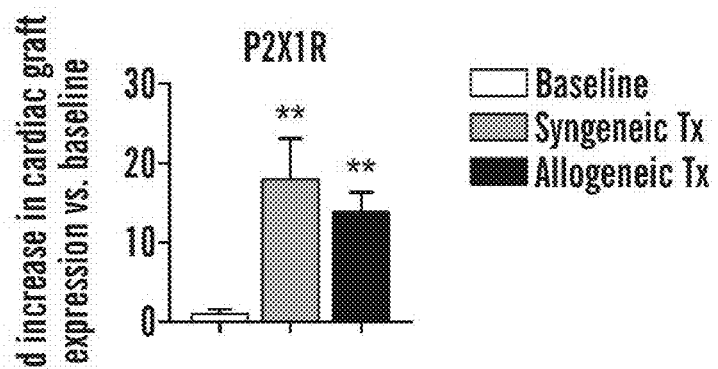
FIGS. 1A-1C demonstrate that in accordance with an embodiment herein, P2X1R was upregulated in syngeneic and allogeneic heart grafts in a murine model (FIG. 1A) while upregulation of P2X7R was more upregulated in the allogeneic compared to syngeneic grafts (FIG. 1B). ATP level in the serum was higher during graft rejection (FIG. 1C). *$p<0.05$, **$p<0.01$ vs. Baseline; #$p<0.01$ vs. Syngeneic.
Figure 1B:
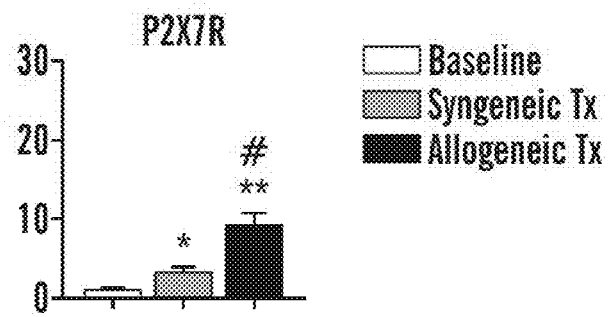

Example 1: P2X7R is Specifically Upregulated in the Graft During Allogeneic Heart Rejection The inventors evaluated the expression of P2XsR in cardiac transplants in vivo. Hearts from BALB/c (H-$2^d$)

mice were heterotopically transplanted into C57BL/6 (H-2$^b$) mice, and cardiac transplants were harvested at day 7 after transplantation (the average time for cardiac transplant rejection). Expression of the P2XsR was compared to baseline values (i.e. untransplanted BALB/c hearts or naïve C57BL/6 splenocytes) by real-time PCR. Upregulation of P2X1R (14-fold increase), and P2X7R (9-fold increase) receptors was observed in the cardiac transplants (FIGS. 1A, 1B). Conversely, no induction of P2XsR was observed in splenocytes of cardiac-transplanted mice. To dissect the specific effect of the alloimmune response from effects of ischemia-reperfusion injury and nonspecific inflammation, P2XsR expression in allografts and syngrafts was compared (C57BL/6 hearts into C57BL/6 recipients). P2X1R, and P2X7R were also upregulated in syngeneic heart transplants compared to baseline (FIGS. 1A and 1B); however only P2X7R was significantly increased in allogeneic compared to syngeneic transplants. P2X7R staining was clear positive staining was evident in the mononuclear immune cell infiltrate of cardiac transplants harvested at day 7 (data not shown). Complete overlap was confirmed between CD3$^+$ T cells and P2X7R expression via immunofluorescence and confocal microscopy. When the graft infiltrate was analyzed in patients suffering from acute heart rejection, clear expression of P2X7R was observed (data not shown), and confocal imaging confirmed that P2X7R staining overlapped with CD3 staining (data not shown).

Example 2: P2X7R Targeting Promotes Heart Graft Survival

Figure 2A:
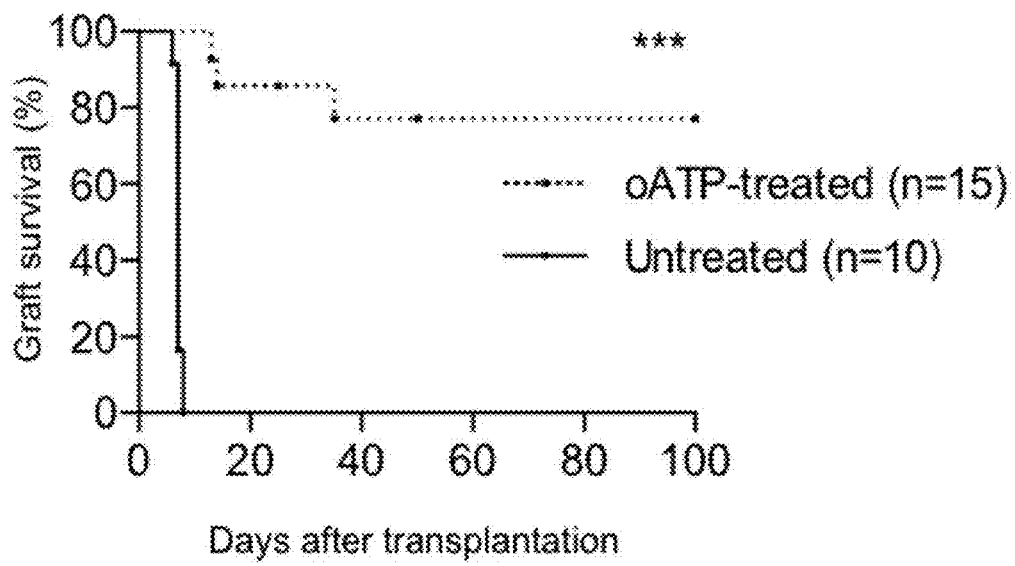
FIGS. 2A-2C demonstrate that, in accordance with an embodiment herein, oATP prevented transplant rejection in 80% of heart transplants in a murine model (n=15, *$p<0.001$ vs. Untreated.

The effect of P2X7R targeting in preventing cardiac transplant rejection was tested using the P2X7R inhibitor oATP. P2X7R targeting using short-term treatment of oATP (250 mg oATP i.p. daily for 14 days) induced long-term cardiac transplant survival (>100 days) in 80% of recipients (FIG. 2A).

Figures 2B, 2C:
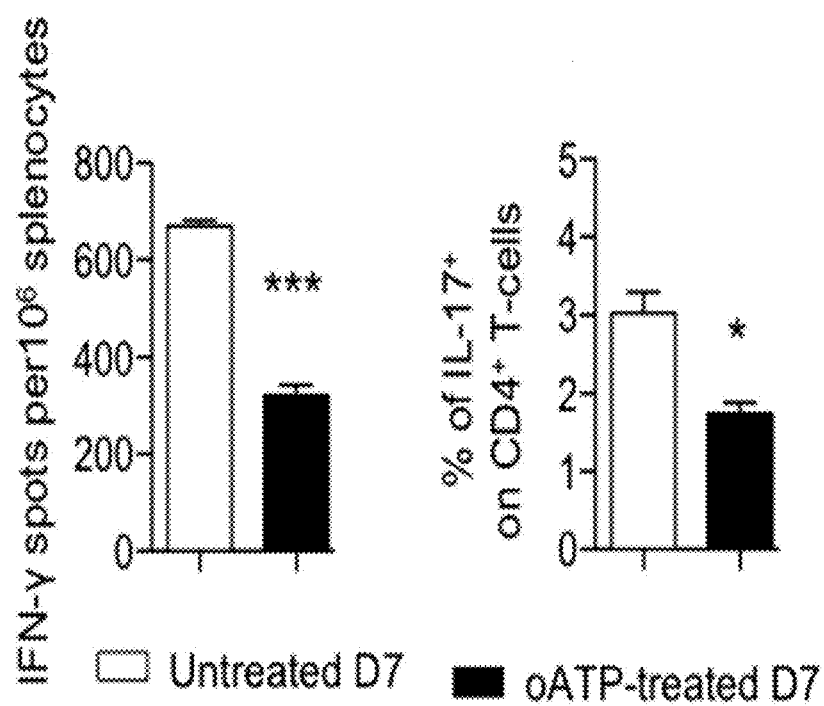

Example 3: P2X7R Targeting Promotes Donor-Specific Hyporesponsiveness and Graft Protection To evaluate the effect of P2X7R targeting on the immune system of cardiac-transplanted mice, splenocytes were harvested at days 7 and 100 post-transplantation and were challenged with BALB/c irradiated splenocytes in an ELISPOT assay. Reduced numbers of IFN-γ-producing cells were observed in oATP-treated compared to untreated mice at day 7 (FIG. 2B). The percentage of Th17 cells was similarly reduced in oATP-treated mice (FIG. 2C). Graft protection and reduced infiltration was observed at day 7 and 100 after transplantation (data not shown)

Figures 3A, 3B:
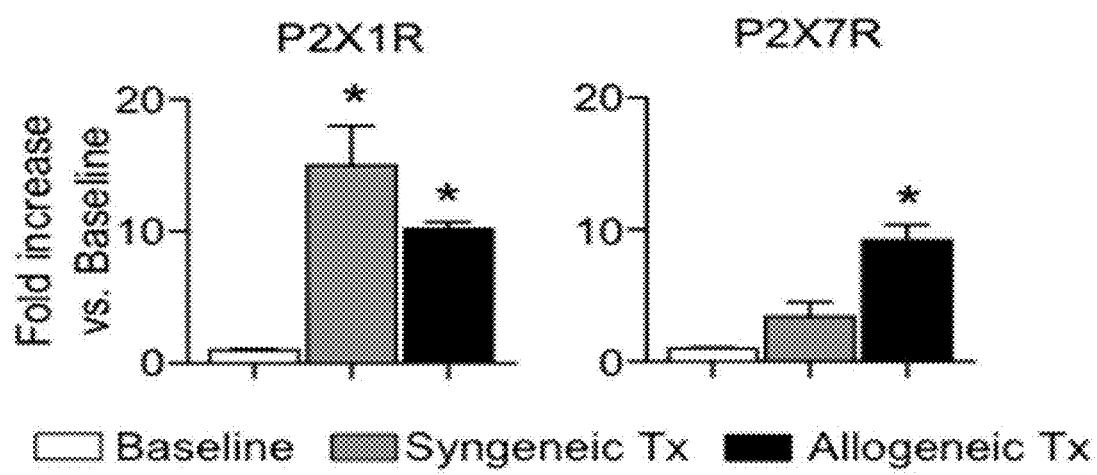
FIGS. 3A-3B demonstrate that, in accordance with an embodiment herein, P2X1R was upregulated in syngeneic and allogeneic islet grafts in a murine model (FIG. 3A) while upregulation of P2X7R was evident only in allogeneic grafts (FIG. 3B). *$p<0.05$ vs. Baseline.

Example 4: P2X7R is Specifically Upregulated in the Graft During Allogeneic Islet Rejection BALB/c or C57BL/6 islets were transplanted under the kidney capsule of C57BL/6 mice rendered diabetic through streptozotocin treatment, and islet grafts were harvested at day 14 after transplantation. RT-PCR was performed on tissues extracted, and P2XsR expression was compared to baseline (i.e. to untransplanted BALB/c or C57BL/6 islets). Specific upregulation of P2X7R was clear in allogeneic islet grafts at day 14 after transplantation, with no significant elevation in syngeneic grafts (FIG. 3A), while a specific P2X1R increase was observed both in allogeneic and syngeneic grafts (FIG. 3B). Upregulation of P2X7R in the islet graft appear thus appear to be a specific signature of islet rejection. Histological analysis confirmed P2X7R staining in graft-infiltrating lymphoid cells (data not shown), and confocal microscopy demonstrated specific P2X7R expression on virtually all CD3$^+$ graft-infiltrating T-cells (data not shown).

Example 5: P2X7R Targeting with oATP Treatment Promotes Islet Graft Survival

Figure 4A:
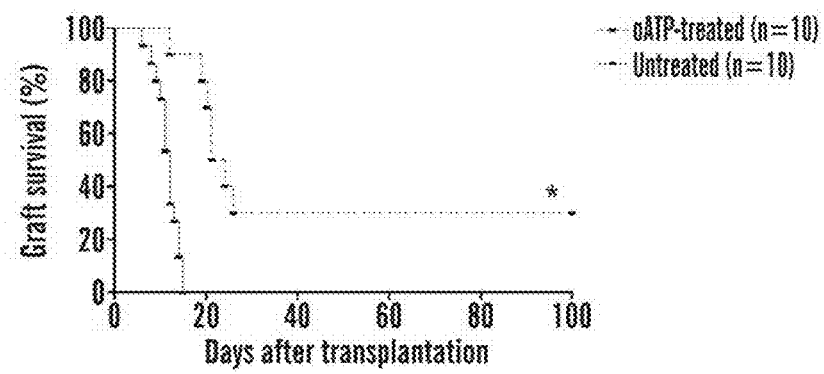

In mice were treated with oATP (oATP 250 μg i.p. daily for 14 days) prolongation of islet allograft survival was observed (MST=22 days, n=10; p<0.0001 vs. Untreated) with indefinite graft survival (>100 days) achieved in 3 out of 10 recipients (FIG. 4A).

Example 6: P2X7R Targeting with oATP Induces Donor-Specific Hyporesponsiveness

The effect of oATP treatment on the immune system of transplanted mice was tested. Splenocytes were collected in untreated or oATP-treated mice at day 14 after transplantation and challenged ex vivo in an ELISPOT assay with BALB/c irradiated splenocytes. Significantly lower levels of IFN-γ-producing cells were observed in oATP-treated compared to untreated mice (FIG. 4B); similarly, reduced numbers of Th17 cells were observed (FIG. 4C) at day 14 in oATP-treated mice.

Example 7: P2X7R Targeting with oATP Reduced T-Cell Infiltration in the Grafts

The inventors next analyzed graft pathology at day 14 after transplantation with preserved insulin staining in oATP-treated mice (data not shown). The presence of Th1 cells was then analyzed in the graft infiltrate by quantification, via RT-PCR, by assessing intra-graft Tbet and Rorc mRNA expression. A reduction in intra-graft Th1 cells was observed in oATP-treated mice (Untreated=1.0±0.3 vs. oATP-treated=0.4±0.1, n=3; p=0.04; FIG. 4D).

Figure 4E:
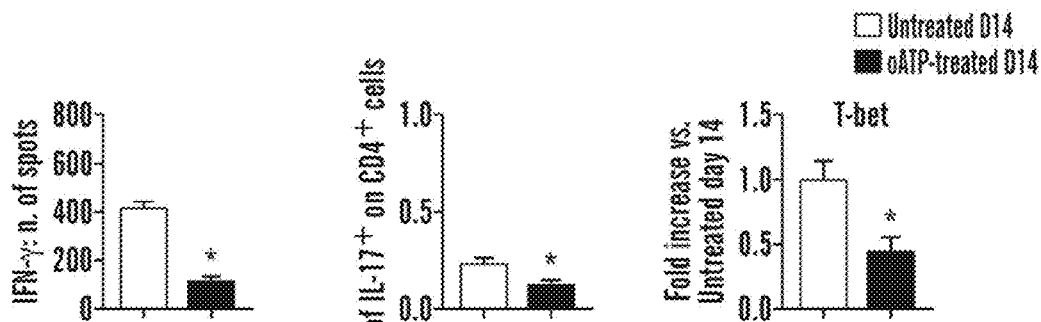
Figure 4E:
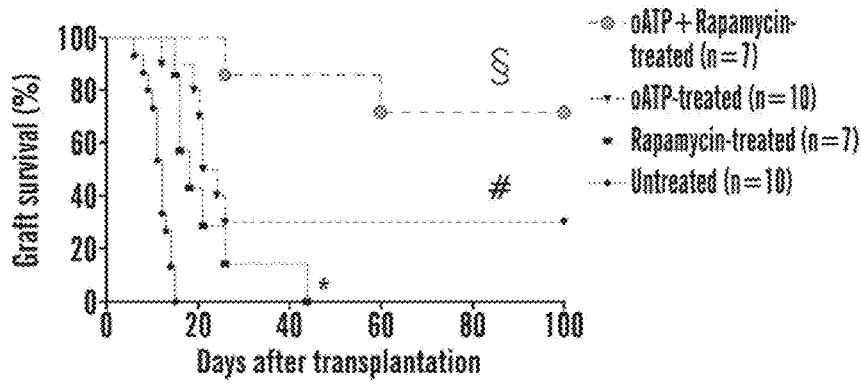

Example 8: Rapamycin and P2X7R Targeting with oATP Synergize in Reducing Allostimulation and in Preventing Allograft Rejection To assess the potential of P2X7R targeting in a clinically relevant combination treatment, the synergism between oATP and Rapamycin was investigated. Rapamycin alone (0.1 mg/kg for 10 days) slightly prolonged islet allograft survival (MST=19 days, n=5; p=0.0006 vs. Untreated; FIG. 4E); notably, when oATP treatment was combined with Rapamycin, a significant synergism was obtained.

Example 9: P2X7R Targeting Inhibits CD4$^+$ T-Cell Activation

The effect of P2X7R targeting was tested by treatment with oATP during T-cell activation. Firstly, in an ELISPOT assay, naïve CD4$^+$ T-cells were stimulated with 0.5 μg/ml anti-CD3-Ig and anti-CD28-Ig for 24 hours; when 100 μM oATP was added to cultures, the number of IFN-γ-producing CD4$^+$ T-cells was significantly reduced compared to controls (FIG. 5A). Similarly, in a T-cell proliferation assay, CFSE-labeled naïve CD4$^+$ T-cells were stimulated for 4 days with 0.5 μg/ml anti-CD3-Ig and anti-CD28-Ig; treatment with 100 µM oATP diminished CD4+ T-cell proliferation (FIG. 5B, right panel) compared to controls (FIG. 5B, left panel).

Figures 6A, 6B:
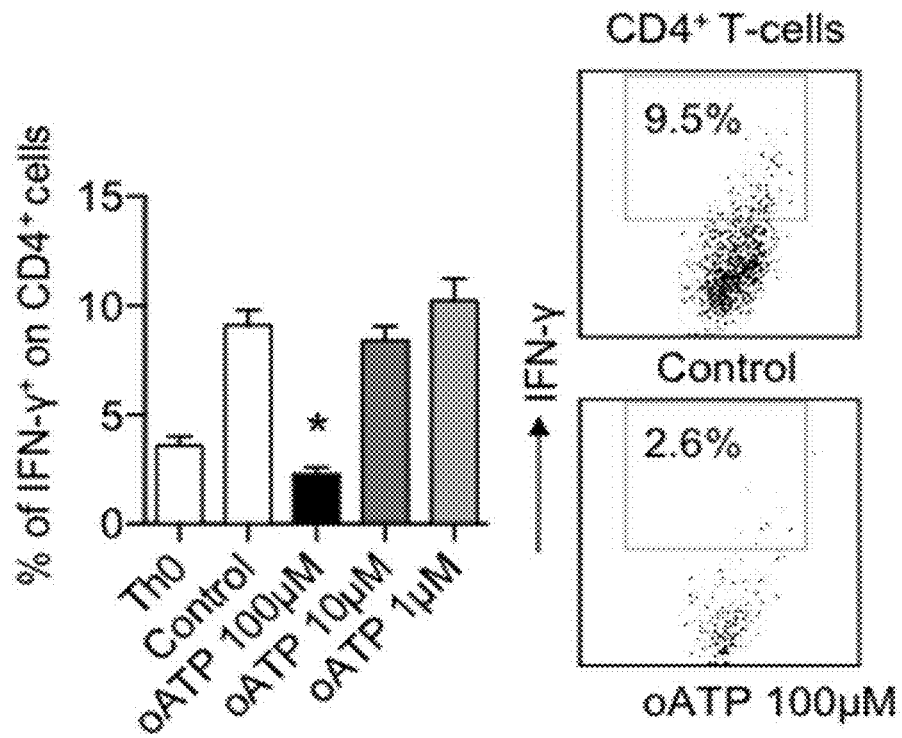
Figures 6C, 6D:
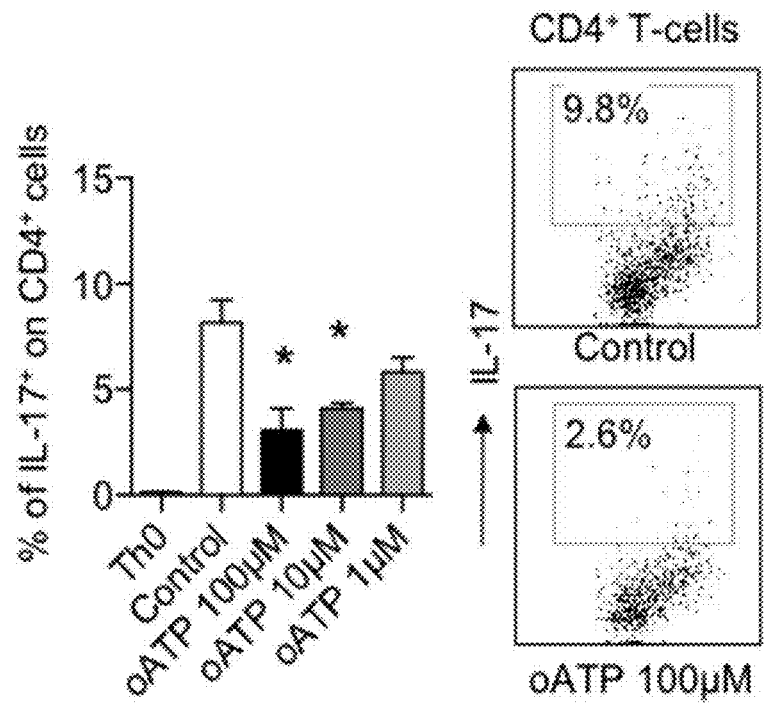

Example 10: P2X7R Targeting In Vitro Inhibits STAT3 Phosphorylation in CD4+ T-Cells During Activation To assess which molecular pathway was preferentially inhibited by P2X7R targeting, the activation/phosphorylation status of several crucial molecules in T-cell signaling was analyzed. 60 minutes after anti-CD3-Ig and anti-CD28-Ig mediated activation, cells were lysed and the phosphorylation status of CREB, Erk, Akt, JNK, p38, p70 S6 Kinase, STAT3, and STAT5A/B was assessed using the Millipore Milliplex Cell Signaling Assay. A reduced level of p-STAT3 was observed in oATP-treated compared to untreated T-cells (FIG. 5C). Data were confirmed by western blot (FIG. 6D). To demonstrate that the effect of oATP is STAT3-phosphorylation-inhibition-dependent, the effect of Colivelin treatment, a peptide that promotes STAT3 phosphorylatin, was tested. Colivelin was shown to significantly revert oATP-mediated suppression of IFN-γ-producing cells (FIG. 5E).

Example 11: P2X7R Targeting In Vitro Inhibits Th1 and Th17 Differentiation

Naïve Th0 cells were differentiated into Th1 or Th17 cells, and IFN-γ+ and IL-17+ cells were quantified by flow cytometry. Addition of 100 µM oATP inhibited the conversion of naïve Th0 cells into Th1 (FIGS. 6A-6B) and Th17 cells (FIGS. 6C-6D).

Example 12: P2X7R Genetic Upregulation In Vitro Promotes Th1 and Th17 Differentiation To confirm the role of P2X7R in Th1/Th17 differentiation, P2X7R cDNA was transduced using a pMY-IRES-GFP retroviral vector into CD4+ T cells, and upregulation of P2X7R expression was confirmed by western blot (FIG. 6E). In a Th1/Th17 generation assay, pmY-P2X7R CD4+ T cells displayed increased differentiation capacity compared to pmY-mock CD4+ T cells, as assessed by T-bet (FIG. 6F) and ROR-γ expression (FIG. 6G).

Example 13: P2X7R Targeting Delays Diabetes Onset in NOD Mice

Figure 7:
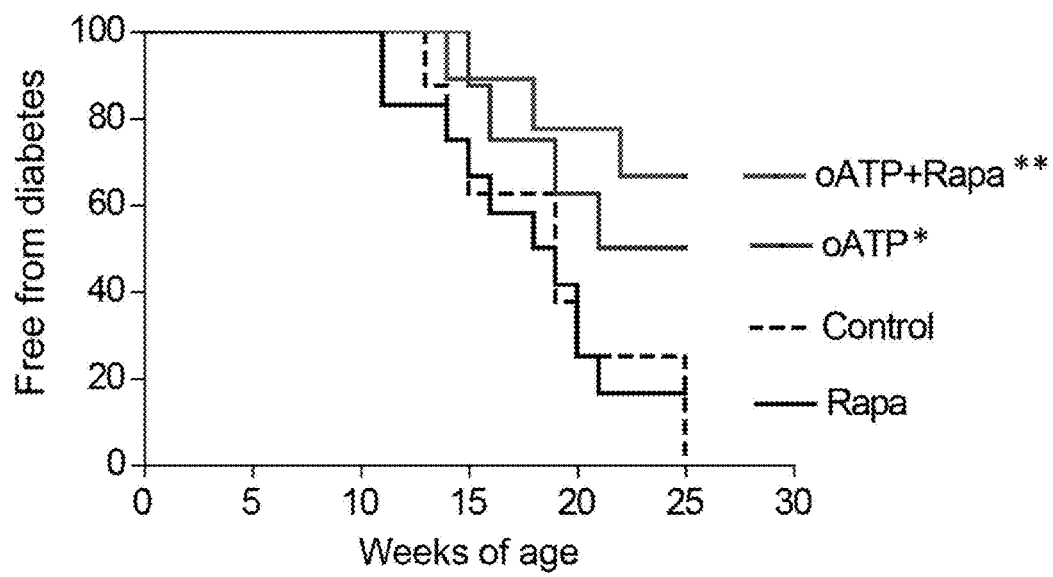
FIG. 7 demonstrates that, in accordance with an embodiment herein, Rapamycin plus oATP (**p<0.01 vs. all excluding oATP alone) (*<0.05 vs. Rapamycin and Control) delayed diabetes onset.

The potential effect of P2X7R targeting on diabetes onset was tested in 10-week-old normoglycemic NOD mice. Untreated NOD mice invariably developed diabetes by 15-20 weeks of age (FIGS. 5A-5E). Conversely, when mice were treated with oATP (250 µg i.p. daily for 14 days) a delay in the onset of diabetes was observed (50% of mice were protected at 25 weeks of age) (FIG. 7). Rapamycin (0.1 mg/kg for 10 days) treatment was again synergistic with oATP treatment, inducing a further delay in the onset of diabetes (FIG. 7) with 70% of mice protected from diabetes at 25 weeks, while rapamycin treatment alone was ineffective in delaying diabetes in NOD mice (FIG. 7). This group of experiments confirmed that the ATP/P2X7R axis is indeed relevant to allo- and autoimmune responses in vivo and that P2X7R targeting can be viewed as a novel strategy to curb both responses. Interestingly, T cell infiltrating pancreatic islets appeared P2X7R+ (data not shown).

Figure 8:
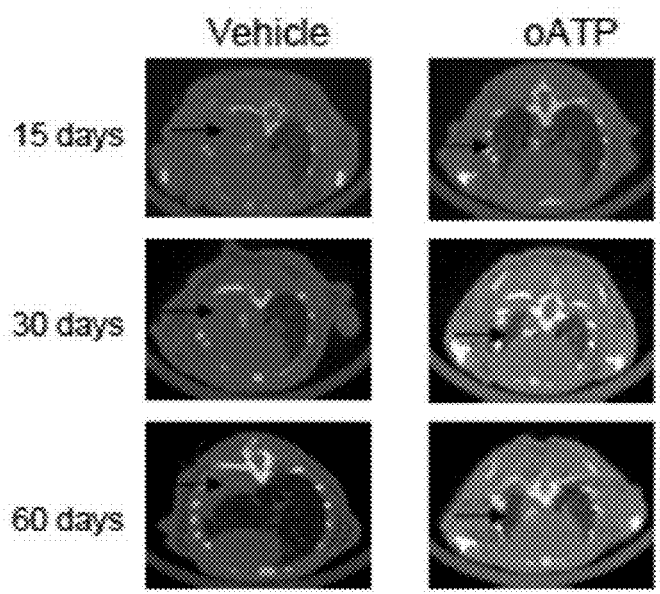
FIG. 8 demonstrates that, in accordance with an embodiment herein, macroscopically, transplanted lung appeared preserved in treated mice, while completely fibrotic in untreated mice Radiological analysis confirmed preservation of the alveolar spaces.
Figure 9A:
FIGS. 9A-9C demonstrate that, in accordance with an embodiment herein, after rescue oATP-treatment, preservation of alveolar space is observed after radiological (FIG. 9A) and histological (FIG. 9B) analysis. Better functional preservation of lung compliance is also observed (FIG. 9C). *p<0.05 vs Vehicle.
Figure 9B:
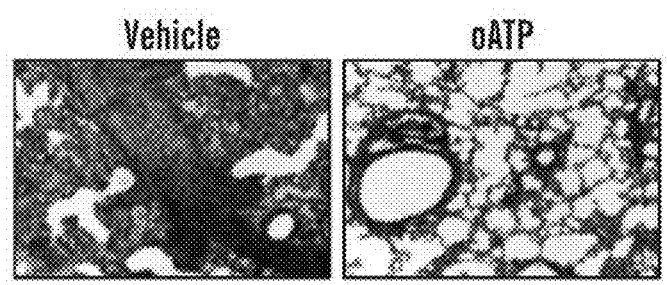
Figure 9C:
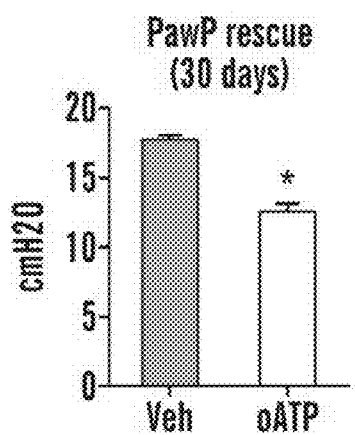

Example 14: oATP-Treatment Prevents Allogeneic Graft Rejection and Lung Fibrosis The effect of oATP treatment in a model of allogeneic orthotropic left lung transplantation (Bm12 into C57BL/6) was assessed. Graft rejection and tissue fibrosis occurs early after transplantation and it is complete by day 30. Macroscopically, oATP treatment prevents graft fibrosis of the graft lung (data not shown). Moreover histological analysis showed highly reduced inflammation and preserved alveolar spaces in the treated mice at different time points (data not shown). CT scan was also performed in untreated or oATP-treated mice. Radiological analysis confirmed the preserved alveolar space and thus the functional integrity of oATP-treated compared to untreated mice (FIG. 8). oATP treatment is a rescue therapy for lung rejection. In a complementary experiment, oATP was tested as a rescue therapy for lung rejection. Bm12 left lung was transplanted into C57BL/6 mice and oATP treatment was started at day 10 after transplantation (when graft infiltration and rejection are evident) and mice follow for 30 days. At the end of the treatment radiological (FIG. 9A) and histological (FIG. 9B) analysis demonstrated reversal of graft rejection and no signs of fibrosis. Similarly, functional data showed a better (PawP) performance in oATP-treated mice (FIG. 9C).

Example 15: Diabetes—Overview

The lymphocytic ionotropic purinergic P2X receptors (P2X1RP2X7R, or P2Xs) sense ATP released during cell damageactivation, thus regulating T-cell activation. The inventors aimed to define the role of P2Xs during islet allograft rejection and to establish a novel anti-P2X strategy to achieve long-term islet allograft function. The data demonstrates that P2X1R and P2X7R are induced in islet allograft-infiltrating cells, that only P2X7R is increasingly expressed during alloimmune response, and that P2X1R is augmented in both allogeneic and syngeneic transplantation. In vivo short-term P2X7R targeting (using periodateoxidized ATP [oATP]) delays islet allograft rejection, reduces the frequency of Th1/Th17 cells, and induces hyporesponsiveness toward donor antigens. oATP-treated mice displayed preserved islet grafts with reduced Th1 transcripts. P2X7R targeting and rapamycin synergized in inducing long-term islet function in 80% of transplanted mice and resulted in reshaping of the recipient immune system. In vitro P2X7R targeting using oATP reduced Tcell activation and diminished Th1/Th17 cytokine production. Peripheral blood mononuclear cells obtained from long-term islet-transplanted patients showed an increased percentage of P2X7R+CD4+ T cells compared with controls. The beneficial effects of oATP treatment revealed a role for the purinergic system in islet allograft rejection, and the targeting of P2X7R is a novel strategy to induce long-term islet allograft function.

Example 16: P2X7R is Specifically Expressed in Islet Allograft Infiltrating Lymphocytes During the Alloimmune Response In Vivo The expression of P2XR mRNA during the alloimmune response in vivo was evaluated in an islet transplantation model. BALB/c (H-2d) islets were transplanted under the kidney capsule of C57BL/6 (H-2b) mice, rendered diabetic through streptozotocin, and islet allografts and spleens were harvested at day 14, according to the kinetics of islet allograft rejection.

P2XR expression levels were compared with baseline values using untransplanted BALB/c islets or naïve C57BL/6 splenocytes. A significantly higher expression of P2X1R (10-fold increase vs. baseline, n=3; P=0.0002) and P2X7R (10-fold increase vs. baseline, n=3; P=0.01) was evident in the graft. No changes were observed in the expression of the remaining P2XRs in the graft or in any P2XR in the spleen.

To explore the possible effects of ischemia/reperfusion injury and peritransplant inflammation on P2XR expression levels, the inventors evaluated P2XR expression in the setting of syngeneic islet transplantation—C57BL/6 islets into hyperglycemic C57BL/6 mice—in which the effects of the alloimmune response are absent. At day 14 after transplantation, P2X1R expression was increased in the syngeneic graft compared with baseline (14-fold increase, n=3; P=0.008), similarly to what was observed in allogeneic grafts (syngeneic day 14 vs. allogeneic day 14, n=3; P=NS); these data suggest that P2X1R expression is related more to ischemia/reperfusion injury and peritransplant inflammation than to the allogeneic response.

Conversely, P2X7R expression did not significantly increase in syngeneic grafts (n=3; P=NS vs. baseline), thus suggesting that P2X7R expression is specifically increased during alloimmunity (syngeneic day 14 vs. allogeneic day 14, n=3; P=0.04. The inventors used immunostaining to assess which cell-type was responsible for the higher expression of P2X7R observed. P2X7R-positive staining was observed in the mononuclear cell infiltrate at day 14 after transplantation, with no P2X7R expression in kidney structures or islet parenchymal cells. ATP levels in the serum were stable over the course of islet transplantation.

Example 17: Targeting P2X7R In Vivo Prolongs Islet Allograft Survival oATP was used to test the effect of P2X7R targeting in the allogeneic islet transplantation model. oATP has been shown to irreversibly antagonize P2X7R through the selective modification of lysine residues in the vicinity of the ATP-binding site and may also exert additional immunomodulatory effects through the modulation of the other purinergic receptors (31,32). Untreated mice invariably rejected islet transplants within 14 days (mean survival time [MST]=12 days, n=10; conversely, mice treated daily with oATP (250 mg i.p.) for 14 days displayed a significant delay in islet rejection (MST=22 days, n=10; p=0.0001 vs. untreated), and 3 of 10 mice showed long-term graft function at 100 days after transplantation.

Example 18: Targeting P2X7R In Vivo Reduces the Severity of the Alloimmune Response Immune profiling of islet-transplanted oATP-treated and untreated mice was performed at day 14 after transplantation. When splenocytes harvested from oATP-treated recipients were challenged with donor-derived splenocytes, a reduction was observed at day 14 in the number of cells producing IFN-γ (oATP-treated=117 6 9 vs. untreated=418 6 26, n=5; P, 0.0001), with no effect on the number of cells producing IL-4. No significant changes in the percentages of peripheral CD4+ T effector cells were observed between groups (CD44highCD62LlowCD4+ T cells). Slight reductions were evident in the percentages of CD8+ T effector cells and of Th17 cells. No differences were observed in the percentages of regulatory T-cells (CD25+FoxP3+CD4+ T-cells, or Tregs. The cytokine profile of sera showed that IL-6, a Th17 cytokine, was reduced in oATP-treated recipients, whereas only minor changes were observed for all other cytokines examined.

Example 19: Targeting P2X7R In Vivo Reduces Infiltration and Th1 Transcripts in Islet Allografts The inventors analyzed the pathology of islet allografts 14 days after transplantation.

Islet structure was substantially compromised, and insulin or glucagon staining were undetectable in untreated mice, with diffuse infiltration primarily constituted by CD3+ T cells and MAC2+ macrophages, with very few FoxP3+ cells. Conversely, islet structure and insulin and glucagon staining were maintained in oATP-treated mice, with infiltrate mainly confined to the islet borders with several FoxP3+ cells. Semiquantitative analysis confirmed preserved insulin staining at day 14 in oATP-treated mice but not in the untreated mice, with no major differences in the overall infiltrate. A reduction in the mRNA expression of Tbet, a marker of the Th1 immune response (threefold decrease, n=3; P=0.02 vs. untreated), but not in RORc, a marker of the Th17 immune response, was observed in the graft infiltrate of oATP-treated mice. Further analysis of the insulin and glucagon content in the transplanted islets confirmed the graft protection conferred by oATP treatment at day 14 (insulin content: untreated=2.3 6 0.4 mg/L vs. oATP-treated=3,698 6 843 mg/L, n=5 and 10; P=0.009; glucagon content: untreated=undetectable vs. oATP-treated=32,999 6 18,657 pmol/L, n=5 and 6; P=0.007.

Example 20: Targeting P2X7R In Vitro Reduces the Severity of the Alloimmune Response To confirm the data obtained in vivo, the effect of targeting P2X7R in vitro was evaluated using alloimmune-relevant assays. Responder splenocytes from C57BL/6 mice were challenged with irradiated stimulator splenocytes from BALB/c mice. The numbers of cells producing IFN-γ and IL-4 were evaluated in an ELISPOT assay in the presence of increasing concentrations of oATP. P2X7R targeting robustly inhibited IFN-γ production (cells producing IFN-γ: oATP 100 mmol/L=30 6 2 vs. control=190 6 4, n=5; P, 0.0001), but a dose-dependent increase in IL-4 production was observed. To confirm in vitro suppression of the Q:2 alloantigen response, the inventors performed a mixed leukocyte reaction experiment in which alloantigen-mediated cell proliferation appeared to be suppressed (number of proliferating cells as measured by 3H-thymidine incorporation: oATP 100 mmol/L=136 6 5 vs. control=6,199 6 498, n=5; P, 0.0001). C57BL/6 splenocytes were also challenged with allogeneic cells in the presence of oATP (100 mmol/L) for 24 h, and apoptosis was assessed by fluorescence-activated cell sorter as the percentage of annexin V+7AAD2 cells; no increase in the percentage of apoptotic cells was detected.

The effect of increasing doses of oATP on Th1/Th17 cytokine levels was next tested. A dose-dependent response was evident, in which oATP reduced the number of cells producing Th1 cytokines (IFN-γ and IL-2) and Th17 cytokines (IL-6 and IL-17). Because it has been reported that oATP may affect other P2XRs, the inventors made use of the availability of the selective P2X1R inhibitor NF 449 and of the selective P2X3R inhibitor NF 110. C57BL/6 splenocytes were stimulated with irradiated BALB/c splenocytes, and IFN-γ production was evaluated in the presence of these inhibitors. P2X1R and P2X3R inhibition failed to modulate alloantigen-mediated IFN-γ production; these data confirmed the marginal role of P2X1R and P2X3R in the alloimmune response, at least in vitro.

Example 21: Genetic Targeting of P2X7R Slightly Prolongs Islet Graft Survival The effect of genetic targeting of P2X7R on islet graft survival was also determined. P2X7R2/2 C57BL6 mice were transplanted with allogeneic BALB/c islets, and partial prolongation of graft survival was observed compared with wild-type recipients (MST: P2X7R2/2=19 days, n=10; P, 0.0001 vs. wild-type. oATP treatment on P2X7R2/2 recipients was able to further prolong graft survival (MST: oATP-treated P2X7R2/2=26 days, n=5; P=0.04 vs. untreated P2X7R2/2. To investigate the purinergic system function in P2X7R2/2 mice, the inventors analyzed the effect of benzoyl-ATP (Bz-ATP), a synthetic agonist of the purinergic receptors, in CD4+ and CD8+ T cells. When 1 mmol/L Bz-ATP was added to the cultured cells, IFN-γγ production increased in CD4+(FIG. 4B) and CD8+ T cells isolated from wildtype mice. Bz-ATP similarly stimulated IFN-γγ production from CD4+ and CD8+ T cells isolated from P2X7R2/2 mice. The inventors hypothesized that compensatory mechanisms may have arisen in P2X7R2/2 mice, and in particular, investigated a possible upregulation of P2X1R, P2X3R, and P2X4R, which also have been associated with the immune response. CD4+ and CD8+ T cells were extracted from wild-type and P2X7R2/2 mice, and the relative expression of P2XRs was assessed by RTPCR. Higher levels of P2X1R and P2X4R were found in P2X7R2/2-derived CD4+ T cells (P2X1R: 2-fold increase vs. wild-type, n=3, P=0.02; P2X4R: 1.7-fold increase vs. wild-type, n=3, P=0.03) and CD8+ T cells (P2X1R: 16-fold increase vs. wild-type, n=3, P=0.003; P2X4R: 1.3-fold increase vs. wild-type, n=3, P=0.04). Promotion of islet graft survival obtained by oATP treatment also in P2X7R2/2 recipients demonstrates that the targeting of other purinergic receptors may contribute to the immunomodulatory effects of oATP; however, some caution should be used when analyzing data obtained from P2X7R2/2 mice because compensatory mechanisms in the purinergic system are present.

Example 22: Rapamycin and P2XR7 Targeting In Vivo Synergize in Reducing the Alloimmune Response To evaluate a potential clinically relevant protocol, oATP combined with a clinical-grade dose of rapamycin was tested (oATP at 250 mg day 0 through day 15+rapamycin at 0.1 mg/kg day 0 through day 10); five of seven islet-transplanted mice treated with oATP+rapamycin showed long-term graft function at 100 days after transplantation (MST: rapamycin=18; oATP+rapamycin=indefinite, n=7; oATP+rapamycin vs. both untreated and rapamycin, P, 0.0001; oATP+rapamycin vs. oATP, P=0.04). Rapamycin was more effective in prolonging islet graft survival in P2X7R2/2 compared with wild-type recipients (n=7; P=0.04 vs. rapamycin in wild-type), confirming the synergistic effect between P2X7R-targeting and rapamycin. Better protection of islet grafts was observed in wild-type recipients treated with oATP+rapamycin than in P2X7R2/2 recipients treated with rapamycin alone, indicating that the oATP may also target other purinergic receptors. Pathology of islet allografts in long-term protected islet-transplanted oATP+rapamycin-treated mice revealed preserved architecture and maintained insulin and glucagon staining Islet infiltrate was evident but appeared confined to the border of islet allografts. At higher magnifications, FoxP3+ cells infiltrate appeared nearly as abundant as the CD3+ T-cell infiltrate, suggesting a high proportion of Tregs. Mice treated with short-course oATP+rapamycin were further protected from the alloimmune response, as demonstrated by a decrease in the responsiveness toward donor alloantigen and measured by the reduction in cells producing IFN-γ during ex vivo challenge with alloantigens (cells producing IFN-γ: oATP+rapamycin-treated at day 100=60 6 8 vs. untreated at day 14, n=3, P, 0.0001; vs. oATP-treated at day 14, n=3, P=0.008). A parallel reduction in the percentage of CD4+ and CD8+ effector cells was observed in oATP+rapamycin-treated mice. The percentages of peripheral CD4+ effector T cells and CD8+ effector T cells were greatly reduced compared with those observed in oATP-treated mice at day 14. Stable levels of Th17 cells and a slight decrease in the number of Tregs were observed in oATP+rapamycin treated mice. A better protection of the islet graft structure was observed in rapamycin-treated P2X7R2/2 compared with untreated P2X7R2/2 recipients at day 14 after transplantation. Immune cell infiltration was reduced in rapamycin-treated P2X7R2/2 recipients compared with untreated P2X7R2/2 recipients.

Example 23: P2X7R Expression is Increased in CD4+ T Cells Obtained from Islet-Transplanted Patients The P2X7R expression profile in lymphocytes obtained from islet-transplanted patients was determined in order to establish the relevance of the P2X7R/ATP system in human T cells and, potentially, in islet rejection in humans. PBMCs from islet-transplanted patients, T1D patients, and healthy control subjects were harvested, and CD4+ T cells, a key population in islet rejection, were analyzed by flow cytometry. In healthy controls, the P2X7R+CD4+ T-cell population represented 17% of all PBMCs, and P2X7R was expressed in almost 50% of peripheral CD4+ T cells. The percentage of P2X7R+CD4+ T cells observed in recently well-functioning transplanted patients (3 years from last islet infusion) were comparable to those of healthy control subjects. Conversely, the frequency of the P2X7R+CD4+ T-cell population significantly increased in long-term islet-transplanted patients (0.3 years) and in T1D patients. Among CD4+ T cells, an expansion of P2X7R+CD45RO+ cells (T cells with a mature phenotype or memory T cells) was observed in long-term islet-transplanted patients and in T1D patients compared with healthy control subjects. Conversely, a reduction in naïve P2X7R+CD45RA+ cells was observed. These data demonstrate a similar P2X7R expression pattern on CD4+ T cells in long-term islet transplanted patients and in T1D patients, whereas a different pattern is expressed on recently islet-transplanted patients and healthy control subjects.

Example 24: The Specific Human P2X7R Antagonist CE-224535 Inhibits the Alloimmune Response In Vitro To confirm the immunomodulatory effect of P2X7R inhibition, PBMCs obtained from healthy control subjects were challenged with allogeneic irradiated PBMCs obtained from different donors in an ELISPOT assay in the presence of different concentrations of the human-specific P2X7R antagonist CE-224535, which has been investigated in clinical trials for rheumatoid arthritis. A reduction in the number cells producing IFN-γ was observed with CE-224535 treatment at 100 mmol/L (29 6 1 vs. control 51 6 3, n=5, P=0.003).

Example 25: Circulation—Overview

Heart transplantation is a lifesaving procedure for patients with end-stage heart failure. Despite much effort and advances in the field, current immunosuppressive regimens are still associated with poor long-term cardiac allograft outcomes, and with the development of complications, including infections and malignancies, as well. The development of a novel, short-term, and effective immunomodulatory protocol will thus be an important achievement. The purine ATP, released during cell damage/activation, is sensed by the ionotropic purinergic receptor P2X7 (P2X7R) on lymphocytes and regulates T-cell activation. Novel clinical-grade P2X7R inhibitors are available, rendering the targeting of P2X7R a potential therapy in cardiac transplantation. The inventors analyzed P2X7R expression in patients and mice and P2X7R targeting in murine recipients in the context of cardiac transplantation. The data demonstrates that P2X7R is specifically upregulated in graft-infiltrating lymphocytes in cardiac-transplanted humans and mice. Short-term P2X7R targeting with periodate-oxidized ATP promotes long-term cardiac transplant survival in 80% of murine recipients of a fully mismatched allograft. Long-term survival of cardiac transplants was associated with reduced T-cell activation, T-helper cell 1/T-helper cell 17 differentiation, and inhibition of STAT3 phosphorylation in T cells, thus leading to a reduced transplant infiltrate and coronaropathy. In vitro genetic upregulation of the P2X7R pathway was also shown to stimulate T-helper 1/T-helper 17 cell generation. Finally, P2X7R targeting halted the progression of coronaropathy in a murine model of chronic rejection as well. P2X7R targeting is a novel clinically relevant strategy to prolong cardiac transplant survival.

Example 26: P2X7R is Induced in Cardiac Transplants During the Alloimmune Response The expression of P2XsR was evaluated in cardiac transplants in vivo. Hearts from BALB/c (H-2d) mice were heterotopically transplanted into C57BL/6 (H-2b) mice, and cardiac transplants and splenocytes were harvested at day 7 after transplantation (the average time for cardiac transplant rejection). Expression of the P2XsR was compared with baseline values (ie, untransplanted BALB/c hearts or naïve C57BL/6 splenocytes) by real-time PCR. Upregulation of P2X1R (14-fold increase), P2X4R (4-fold increase), and P2X7R (9-fold increase) receptors was observed in the cardiac transplants. Conversely, no induction of P2XsR was observed in splenocytes of cardiac-transplanted mice. To dissect the specific effect of the alloimmune response from effects of ischemia-reperfusion injury and nonspecific inflammation, the inventors compared P2XsR expression in allografts and syngrafts (C57BL/6 hearts into C57BL/6 recipients). P2X1R, P2X4R, and P2X7R were also upregulated in syngeneic heart transplants in comparison with baseline; however, only P2X7R was significantly increased in allogeneic in comparison with syngeneic transplants. P2X2R, P2X3R, P2X5R, and P2X6R expression was unchanged in both cardiac syngrafts and allografts in comparison with baseline. The inventors then assessed which cell type was responsible for the P2X7R upregulation observed with the use of immunohistochemical analysis. P2X7R staining was negative in untransplanted BALB/c hearts, whereas clear positive staining was evident in the mononuclear immune cell infiltrate of cardiac transplants harvested at day 7; cardiomyocytes and other parenchymal cells appeared to be negative for P2X7R staining. The inventors also confirmed complete overlap between CD3+ T cells and P2X7R expression via immunofluorescence and confocal microscopy. In addition, it was evaluated whether P2X7R upregulation was a phenomenon present in patients. When the graft infiltrate in patients experiencing acute heart rejection was analyzed, clear expression of P2X7R was observed, and confocal imaging confirmed that P2X7R staining overlapped with CD3 staining No colocalization was evident between P2X7R expression and CD20+ B cells or CD68+ macrophages.

Example 27: In Vivo Short-Term P2X7R Targeting Prevents Cardiac Transplant Rejection, Abrogates the Th1/Th17 Immune Response, and Reduces Effector T Cells in Mice The effect of P2X7R targeting in preventing cardiac transplant rejection was tested by using the P2X7R inhibitor oATP. Untreated C57BL/6 mice transplanted with BALB/c hearts (fully mismatched) invariably rejected grafts within 7 days (mean survival time of 7 days). P2X7R targeting with the use of the short-term treatment of oATP (250 mg oATP intraperitoneally daily for 14 days) induced long-term cardiac transplant survival (>100 days) in 80% of recipients. To evaluate the effect of P2X7R targeting on the immune system of cardiac-transplanted mice, splenocytes were harvested at days 7 and 100 posttransplantation and were challenged with BALB/c irradiated splenocytes in an enzyme-linked immunosorbent spot (ELISPOT) assay. Reduced numbers of IFN-γ-producing cells and increased numbers of IL-4-producing cells were observed in oATP-treated in comparison with untreated mice at day 7; a stronger effect was observed at day 100 in oATP-treated mice. The percentages of peripheral CD4+ effector T cells (CD4+CD44hiCD62Llow, or CD4+ Teffs), CD8+ effector T cells (CD8+CD44hiCD62Llow, or CD8+ Teffs), regulatory T cells (CD4+CD25+FoxP3+, or Tregs), and Th17 cells (CD4+IL17+) were quantified in cardiac-transplanted mice by flow cytometric analysis. The percentages of CD4+ Teffs and CD8+ Teffs were reduced by in vivo short-term P2X7R targeting in mice at days 7 and 100 posttransplantation in comparison with untreated mice. The percentage of Th17 cells was similarly reduced. No differences in the percentage of Tregs were observed between treated and untreated mice at day 7, but an increase was observed at day 100. Thus, it is demonstrated herein that short-term P2X7R targeting reshapes the immune system and induces hyporesponsiveness toward donor antigens.

Example 28: In Vivo Short-Term P2X7R Targeting Induces Anergy Toward Donor-Derived Alloantigens but Preserves Immunocompetence in Cardiac-Transplanted Mice To assess whether long-term cardiac transplant survival was associated with active regulation toward alloantigens or with reduced immunocompetence, hearts from BALB/c mice were transplanted into immunodeficient C57BL/6 Rag−/− mice together with splenocytes obtained from cardiac transplant recipients. Graft rejection was observed within 20 days in mice adoptively transferred with naïve C57BL/6 splenocytes, and no protection was observed when splenocytes obtained from mice with long-term graft function were coadoptively transferred with naïve splenocytes. Conversely, prolonged graft survival >50 days was observed when splenocytes obtained from cardiac-transplanted mice with long-term graft function were adoptively transferred. These data suggest that in vivo short-term P2X7R targeting is more likely to induce anergy toward graft antigens than to induce active regulation. The immunocompetence of treated mice at day 100 after transplantation was tested. Naïve C57BL/6 mice or oATP-treated mice were immunized with ovalbumin, and splenocytes were rechallenged in vitro 7 days later; no differences in numbers of IFN-γ-producing cells were observed. These data demonstrate that in vivo short-term P2X7R targeting promotes anergy toward graft antigens while maintaining immunocompetence.

Example 29: In Vivo Short-Term P2X7R Targeting Reduces Infiltration and Th1/Th17 Transcripts in Cardiac Transplants To further investigate the effect of in vivo short-term P2X7R targeting on the antigraft response, cardiac transplant infiltrate in oATP-treated and untreated mice was analyzed. Histological analysis performed at day 7 post-transplantation revealed a reduced CD3+ T cell infiltrate in treated in comparison with untreated mice, and semiquantitative analysis confirmed a reduction in degree of infiltration and of coronary vasculopathy. To investigate the effect of oATP treatment on Th1 and Th17 cells infiltrating the cardiac transplant, allograft mRNA expression of T-bet (a Th1 cell marker) and of ROR-γ (a Th17 cell marker) was analyzed; both markers appeared substantially reduced in oATP-treated mice, but no difference in the Th2 transcript GATA3 was observed. At day 100, cardiac allografts were well preserved and free from infiltration in oATP-treated mice. Thus, pathological analysis confirms that P2X7R targeting preserves cardiac transplant morphology.

Example 30: In Vivo Short-Term P2X7R Targeting Inhibits the Expansion of Alloantigen-Specific T Cells To address whether the inhibition of the effector T-cell compartment is related to reduced priming and expansion of alloreactive T cells or to their increased apoptosis, alloreactive-specific T cells were tracked in a transgenic model of cardiac transplantation. Bm12 hearts were transplanted into C57BL/6 Rag−/− mice, and 3×106 ABM CD4+ TCR-Tg T cells (specific for bm12 major histocompatibility complex class II antigens) were subsequently adoptively transferred into cardiac transplant recipients. Seven days posttransplantation, reduced numbers of ABM CD4+ TCR-Tg T cells were evident in oATP-treated in comparison with untreated mice. A marked reduction in the numbers of Teffs and Th17 cells within the Tg population was also observed in oATP-treated in comparison with untreated mice. The inventors then examined whether the reduced number of alloantigen-specific CD4+ T cells was due to reduced proliferation or to increased apoptosis. A decrease in ABM CD4+ TCR-Tg T-cell proliferation, as assessed by the dilution of the intracellular dye carboxyfluorescein diacetate succinimidyl ester, was observed in oATP-treated in comparison with untreated mice, without substantial differences in TCR-Tg T-cell apoptosis 4 days following adoptive transfer. The results obtained demonstrate that the inhibition of the effector cell compartment on oATP treatment is not mediated by a significant increase in apoptosis, but rather by decreased proliferation.

Example 31: P2X7R is Required for oATP to Prolong Cardiac Transplant Survival oATP has been proposed to exert secondary immunomodulatory mechanisms, primarily related to the inhibition of the remaining P2XsR. To verify that the effect on the prevention of cardiac transplant rejection was predominantly due to P2X7R inhibition, the P2X7R−/−C57BL/6 mouse model was used. BALB/c hearts were transplanted into P2X7R−/− mice, and cardiac transplant survival was compared with that of wild-type recipients. A significant prolongation of cardiac transplant survival was observed in P2X7R−/− recipients, confirming the role of P2X7R in allograft rejection. The ability of oATP to prolong cardiac transplant survival was severely altered in P2X7R−/− mice, suggesting that, in the context of cardiac alloimmune response, oATP acts mainly, although not exclusively, through P2X7R. Moreover, these data suggest that compensatory mechanisms exist in P2X7R−/− mice; indeed, ATP has been shown to signal through other P2XsR, in particular, through P2X1R and P2X4R in the context of T-cell activation and immune function. CD4+ T cells obtained from P2X7R−/− mice were analyzed by Western blot, and an upregulation of P2X1R and P2X4R was observed in comparison with wild-type mice. Without wishing to be bound by theory, these data can indicate that the upregulation of P2X1R and P2X4R partially compensate for P2X7R function in the model. Moreover, analysis of T-cell populations in P2X7R−/− mice revealed higher percentages of Teff and Treg cells, thus demonstrating that genetic deletion of P2X7R and the compensatory upregulation of other P2XsR exert profound and complex effects on T-cell activation and homeostasis.

Example 32: In Vitro P2X7R Targeting Inhibits CD4+ T-Cell Activation and Th1/Th17 Differentiation To address the mechanisms underlying P2X7R targeting mediated inhibition of cardiac transplant rejection, the inventors analyzed the effect of P2X7R targeting on T-cell activation and Th1/Th17 differentiation in vitro. P2X7R was expressed on CD4+ and CD8+ T cells isolated from splenocytes, as assessed by Western blotting and real-time PCR, with higher expression levels observed in CD4+ T cells. The effect of in vitro P2X7R targeting with oATP during CD4+ T-cell activation was tested. First, in an ELISPOT assay, naïve CD4+ T cells were stimulated with 0.5 μg/mL anti-CD3-Ig and anti-CD28-Ig for 24 hours, and, when 100 μM oATP was added to cultures, the number of IFN-γ-producing CD4+ T cells was significantly reduced in comparison with controls. Second, in a T-cell proliferation assay, carboxyfluorescein diacetate succinimidyl ester-labeled naïve CD4+ T cells were stimulated for 96 hours with 0.5 μg/mL anti-CD3-Ig and anti-CD28-Ig, and treatment with 100 μM oATP diminished CD4+ T cell proliferation in comparison with controls. Expression levels of the P2XsR were not influenced by the presence of oATP during anti-CD3-Ig/anti-CD28-Ig stimulation. To assess whether oATP is specific for P2X7R or whether it also induces its effect through the inhibition of other purinergic receptors (eg, P2X1R or P2X4R, which have been involved in immune function), the inventors combined 100 μM oATP with 50 μM P2X1R (NF-449) and 5004 P2X4R (5-BDBD) inhibitors; a further suppression of anti-CD3-Ig/anti-CD28-Ig-mediated IFN-γ production was obtained. These data demonstrate that the concentration of oATP is not blocking P2X1R and P2X4R. The inventors next tested the effect of in vitro P2X7R targeting during a Th1/Th17 generation and differentiation assay. A small percentage of naïve Th0 CD4+ T cells (CD4+CD25−) were shown to express P2X7R; however, when Th0 CD4+ T cells were activated and differentiated in the appropriate cytokine milieu into Th1 or Th17 cells, an upregulation of P2X7R was observed. P2X7R targeting with oATP inhibited Th0 conversion into both Th1 and Th17, as assessed by the percentage of IFN-γ+ and IL-17+ cells, respectively. The inventors show, therefore, that P2X7R targeting through oATP suppresses activation, proliferation, and Th1/Th17 differentiation of CD4+ T cells. The inventors then further investigated the role of P2X7R on T-cell activation and Th1/Th17 differentiation by genetic upregulation of P2X7R. P2X7R cDNA was transduced by using a pMY-IRES-GFP retroviral vector into CD4+ T cells (pmY-P2X7R CD4+ T cells), and upregulation of P2X7R expression was confirmed by Western blot. pmY-P2X7R CD4+ T cells were then challenged with anti-CD3-Ig/anti-CD28-Ig stimulation in an ELISPOT assay. A greater number of IFN-γ-producing cells was observed in pmY-P2X7R CD4+ T cells in comparison with cells transduced with the empty vector (pmY-mock CD4+ T cells). In a Th1/Th17 generation assay, pmY-P2X7R CD4+ T cells seemed to display increased differentiation capacity in comparison with pmY-mock CD4+ T cells, as assessed by T-bet and ROR-γ expression.

Example 33: In Vitro and In Vivo P2X7R Targeting Inhibits STAT3 Phosphorylation

Which molecular pathway during T-cell activation was preferentially inhibited by the targeting of P2X7R was next determined. Several key components of T-cell receptor signaling involved in the alloimmune response were examined, and the phosphorylation kinetics following in vitro anti-CD3-Ig/anti-CD28-Ig-mediated CD4+ T-cell activation was evaluated by using the Luminex assay. Peak phosphorylation for the analyzed pathways was observed at 30 minutes for JNK/SAPK1 and at 60 minutes for p70/S6, STAT3, and STAT5; a second peak was seen for STAT5 at 24 hours. A significant inhibition of activation-induced STAT3 phosphorylation was observed when oATP was added to the culture, whereas the phosphorylation of JNK/SAPK1, p70/S6, or STAT5 in CD4+ T cells was unaffected. It was confirmed by Western blot that oATP dose-dependently inhibits STAT3 phosphorylation. To demonstrate that the effect of oATP is STAT3-phosphorylation-inhibition dependent, the inventors tested the effect of Colivelin treatment, a peptide that promotes STAT3 phosphorylation in an add-back experiment. The inventors first confirmed that Colivelin (Col) was able to restore the activation-induced phosphorylation of STAT3 in a dose-dependent manner in oATP-treated CD4+ T cells by Western blotting. Moreover, in an ELISPOT assay, in which naïve CD4+ T cells were stimulated with 0.5 μg/mL anti-CD3-Ig and anti-CD28-Ig, treatment with Colivelin was shown to significantly revert oATP-mediated suppression of IFN-γ-producing cells. The effect of oATP and Colivelin on STAT3 phosphorylation and T-cell function was also evaluated following cardiac transplantation. BALB/c hearts were transplanted into C57BL/6 mice, and STAT3 phosphorylation was assessed by Western blot in CD4+ T cells isolated from splenocytes of mice 7 days after transplantation. oATP-treated mice displayed reduced levels of phosphorylated STAT3 in comparison with untreated mice, and, paralleling the results obtained in vitro, the use of Colivelin was able to reestablish STAT3 phosphorylation in CD4+ T cells of oATP-treated mice. From a functional point of view, the use of Colivelin greatly abrogated the effect of oATP on allograft survival. These data demonstrate that P2X7R signaling is crucial for T-cell activation and Th1/Th17 generation and that this effect is STAT3 dependent.

Example 34: In Vivo Short-Term P2X7R Targeting Prevents Coronary Vasculopathy in a Model of Chronic Heart Cardiac Transplant Rejection To evaluate the importance of P2X7R signaling and targeting in a clinically relevant setting, the effect of oATP treatment in a model of cardiac transplant chronic rejection (bml2 donors to C57BL/6 recipients) was tested. In this model, C57BL/6 mice do not acutely reject bm12 cardiac allografts, but transplanted hearts develop transplant-associated coronary vasculopathy. Cardiac allograft pathology was assessed 40 days after transplantation of bml2 hearts into C57BL/6 mice. Advanced coronary vasculopathy and severe lymphocyte and macrophage interstitial and vascular infiltration were observed in untreated mice in comparison with oATPtreated mice, which displayed only mild cellular infiltration and the absence of coronaropathy, as well. oATP-treated mice also showed a reduced number of IFN-γ-producing cells and an increased number of IL-4-producing cells in an ELISPOT assay when splenocytes were challenged with donor antigens.

Example 35: Inhibition of the Purinergic Pathway Prolongs Mouse Lung Allograft Survival Described herein is the investigation of the role of blocking the purinergic receptor, P2XR7 using its inhibitor oxidized (o)ATP, in modulating allograft rejection in a mouse orthotopic lung transplant model. Mouse lung transplants were performed using mice with major MHC mismatch, BALB/c donor and C57BL6 recipient. Oxidized ATP, was given by IP injection daily and lung allografts evaluated 15 to >60 days after transplantation. In addition, lung recipients were treated with oATP after the onset of moderate-severe rejection to determine its ability to rescue lung allografts. Outcomes were determined based on lung function, histology, thoracic imaging, and allo-immune response. It is demonstrated herein that oATP treatment reduced acute rejection, but more importantly prolonged lung allograft survival for >60 days with no progression in the severity of rejection. Treatment with oATP reduced the number of inflammatory cells within lung allografts and improved lung function which was maintained over time. Both CD4 and CD8 cells were reduced within lung allografts with impaired T cell activation and prolonged impairment of CD8 response. In vitro studies demonstrated that oATP reduced allo-specific CD8 cytolytic response using OT1 T cells and OVA target cells and loss of efficient human cytolytic effector cell function upon human lung epithelial cells. Interestingly, adding current immunosuppressive agents, cyclosporine or rapamycin, did not have any additive benefits upon rejection and oATP alone resulted in better outcomes than cyclosporine alone. This study illustrates a potential new pathway to target to prolong survival of lung transplant recipients.

Introduction

Lung transplantation is an accepted therapy for end-stage lung disease, however, the success is limited by a high incidence of rejection and the development of bronchiolitis obliterans believed to be the manifestation of chronic rejection {Weight, #1}. The discovery of calcineurin inhibitors was a major impact upon the success of lung transplantation, and presently the majority of programs use triple immunosuppression consisting of a calcineurin inhibitor, antimetabolite, and corticoidsteroids {Christie, #2}. In spite of using immunosuppression that has proven successful in other organs, both acute and chronic rejection is relatively high in lung transplant recipients. More importantly, the current immunosuppressive protocols have had little impact upon long-term outcomes over the years. Therefore, one approach is to evaluate novel therapies that have a positive influence upon long-term lung transplant outcomes.

T cell recognition of allogeneic cells results in a rapid highly destructive response to the transplanted organ. Upon T cell activation, there is a rapid proliferation of lymphocytes requiring an increase in adenosine triphosphate (ATP) to meet the metabolic demands {Schenk, 2008 #3}. Excess ATP is released from activated lymphocytes {Yegutkin, 2006 #4}. In addition, ATP is generated from dying cells and activated cells and is recognized as a damage-associated molecular pattern (DAMP) contributing to the activation of the innate immune system {Junger, #10}. Under normal conditions, immune cells are exposed to negligible levels of extracellular (e)ATP, and eATP that is present degraded by ubiquitous ectonucleotidases {Yegutkin, 2002 #5}. Extracellular ATP binds to two families of purinergic receptors, P2X and P2Y stimulating both the innate and active immune systems {Junger, #10; Spooner, #15; Trautmann, 2009 #11}. On T cells, the main P2 receptor is thought to be P2XR7 and ATP activation of this receptor acts as a co-stimulator of TCR signaling {Schenk, 2008 #3} thereby acting as an autocrine response. Therefore it was evaluated whether blocking the ATP/purinergic pathway, thereby limiting the activation of T cells would reduce lung allograft injury.

Oxidized (o)ATP is an irreversible antagonist {Placido, 2006 #7} of P2XR7 and is capable of reducing T cell activation and ATP release. It was shown to improve immune mediated models including diabetes, inflammatory bowel disease, experimental autoimmune encephalitis, and heart transplantataion {Lang, #8; Schenk, 2008 #3; Vergani, #9}. Described herein is the examination of whether blocking purinergic receptors with either a non-selective inhibitor, suramin, or a more selective inhibitor of P2X7R, oATP, was protective in an orthotopic mouse lung transplant model. It is demonstrated herein that oATP reduced acute cellular rejection (ACR), improved lung function, and more importantly prolonged lung allograft function for an extended time, >60 days. In addition, T cells isolated from lung allografts showed impaired allo-immune response and in vitro studies demonstrated reduced CD8 effector function.

Methods

Reagents—

Mice were purchased from the Jackson Laboratories (Bar Harbor, Me.), chemicals and reagents from Sigma Chemical (St. Louis, Mo., USA) and tissue culture supplies from Falcon, BD Biosciences, Franklin Lakes, N.J., unless otherwise specified. Antibodies, anti-mouse CD3, CD4, CD8, CD25, CD44, CD45, CD62L, foxP3, IL-17, IFN-γ, TNF-α, and granzyme B, were obtained from BD Biosciences and eBioscience (San Diego, Calif.) and anti-mouse P2XR7 from Alomone Labs. Cyclosporine A (CSA) and rapamycin (Rap) were from LC Laboratories (Woburn, Mass.) and cytotoxic T-lymphocyte antigen 4 (CTLA-4Ig) from BioXCell, West Lebanon, N.H.

Mouse Orthotopic Lung Transplants—

BALB/c (H-2$^d$) and C57BL/6 (H-2$^b$, B6) were housed in accordance with institutional and National Institute of Health guidelines and experimental protocols were approved by the Animal Care Committee of Boston Children's Hospital. Orthotopic left lung transplants were performed as previously described {Bizargity, #22; Iken, #21}. Briefly, donor mice were anesthetized with ketamine and xylazine, intubated with a 22G Angiocath, and ventilated with isoflurane/oxygen. Lungs were flushed with ice cold phosphate buffered saline, left lung harvested and cuffs placed in the pulmonary artery, pulmonary vein and bronchus. Recipient mice were anesthetized and ventilated with isoflurane/oxygen, and left lung transplants performed via a thoracotomy and implantation of the three-cuffed hilar structures. Transplanted lungs were harvested 15 to 60-70 days following transplantation.

Experimental Groups—

The following experimental groups were included with 4 to 8 transplants/group: (1) normal untransplanted B6 mice; (2) vehicle treated BALB/c donor and B6 recipient (allografts); and (3) oATP (Medestea srl, Turin, Italy) 250 μg/day i.p. treated allografts. Allografts were evaluated 15, 30, and 60-70 days after transplant. CSA (10 mg/kg/day) and/or Rap (0.1 mg/day) i.p. were given to select lung allograft recipients from day 0 to 15 post transplant and 250 μg CTLA-4Ig given IP days 0, 1, 2, 4, and 6.

Outcome Measures—

In vivo assessment of transplanted lung function was performed by thoracic CT scan imaging and measuring peak airway pressures (PawP) as previously described {Bizargity, #22}. ATP levels were measured from transplanted lung bronchoalveolar lavage fluid (BAL) by bioluminescent detection using Enliten ATP assay system (FF2000, Promega Corporation, Madison, Wis.). Hematoxylin and eosin (HE) stained sections were used to determine ACR in a blinded fashion based on accepted guidelines {Stewart, 2007 #23}. Immunohistochemistry was performed on frozen lung tissue sections utilizing CD4 and CD8 antibodies and isotype controls and assessed based on the average of 10 high power fields/lung allograft. Flow cytometry and enzyme-linked immunosorbent spot assay (ELISPOT) for interferon (IFN)-γ and interleukin (IL)-4 were performed as previously described {Vergani, #25; Vergani, #9}. T cell activation/stimulation assays were performed utilizing OT1 cells with OVA peptide {Hogquist, 1994 #14} or stimulated with anti-CD3 antibody, 145-2C11{Azzi, #93} and evaluated for IFN-γ, TNF-α, and granzyme B. Cytotoxicity assay of human peripheral blood monocytes (PBMC) upon IFN-γ stimulated human lung epithelial-like cells (A549, American Type Culture Collection, Manassas, Va.) was assessed based on cells counts following 7 days of co-culture in the presence or absence of oATP.

Statistical Analysis—

Data are expressed as mean±SEM, and statistical analyses performed using one-way ANOVA with the Newman-Keul's test or non-parametric Kruskal-Wallis test (GraphPad, San Diego, Calif.). P values less than 0.05 were considered significant.

Results

Figure 1C:
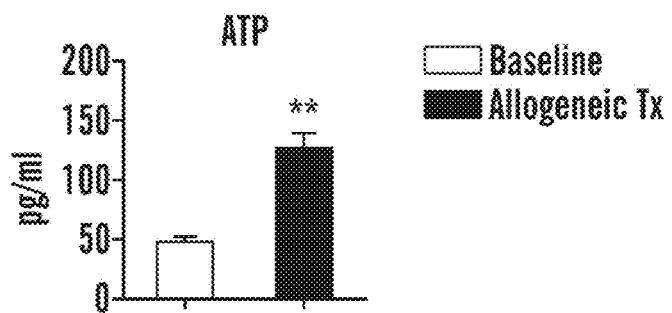
Figure 11A:
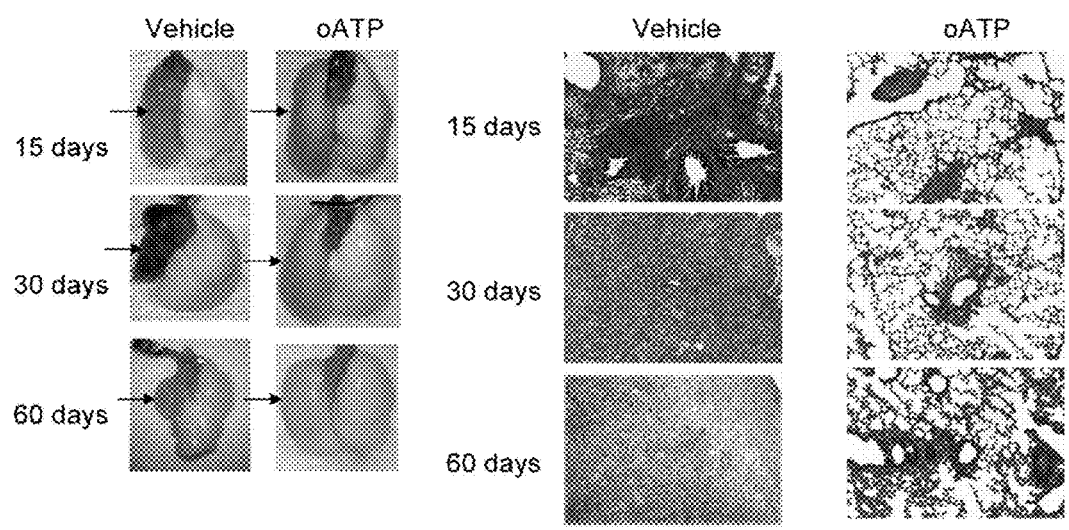
FIGS. 11A-11D demonstrate oATP treatment of lung allografts.
Figure 11B:
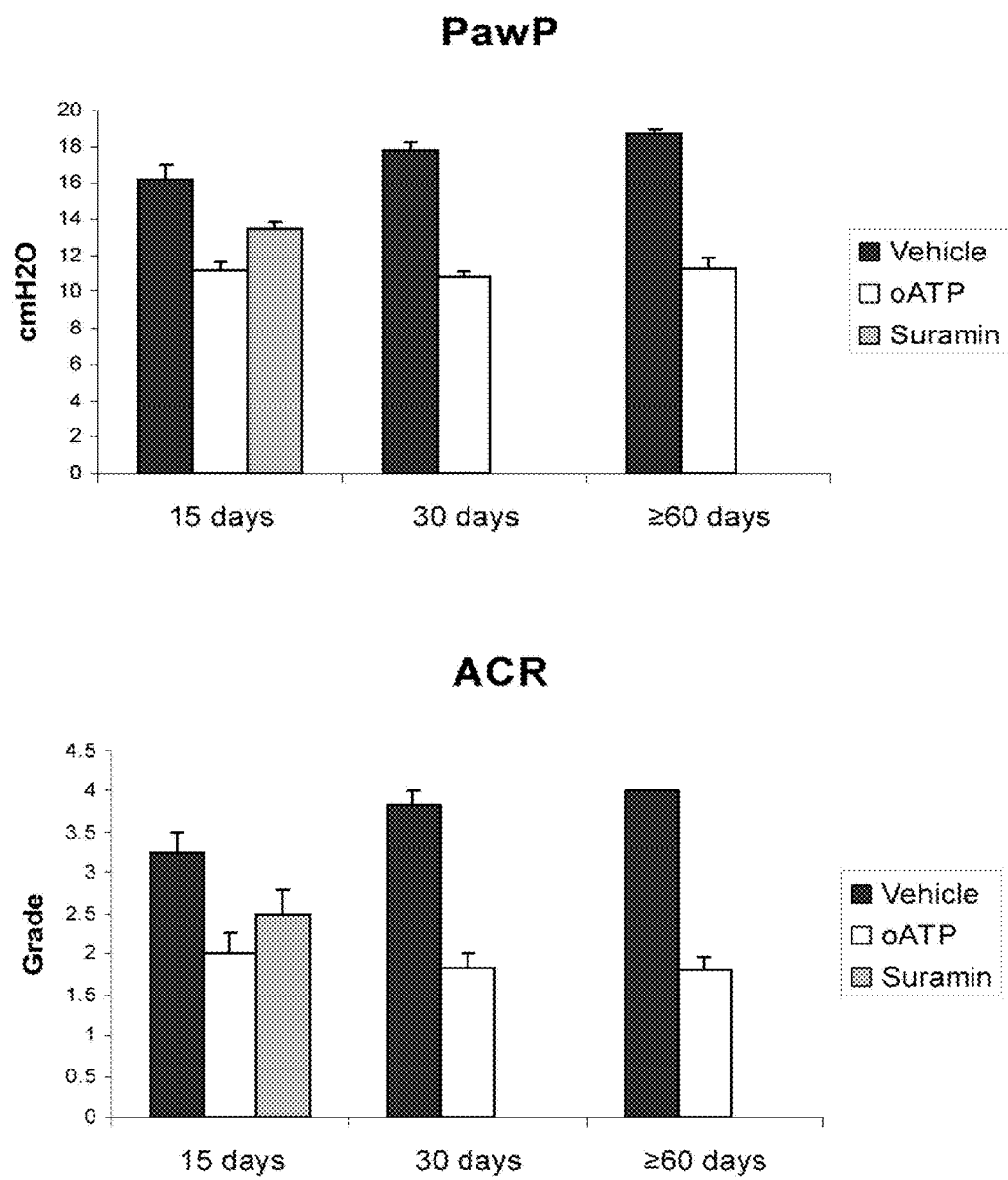
Figure 11C:
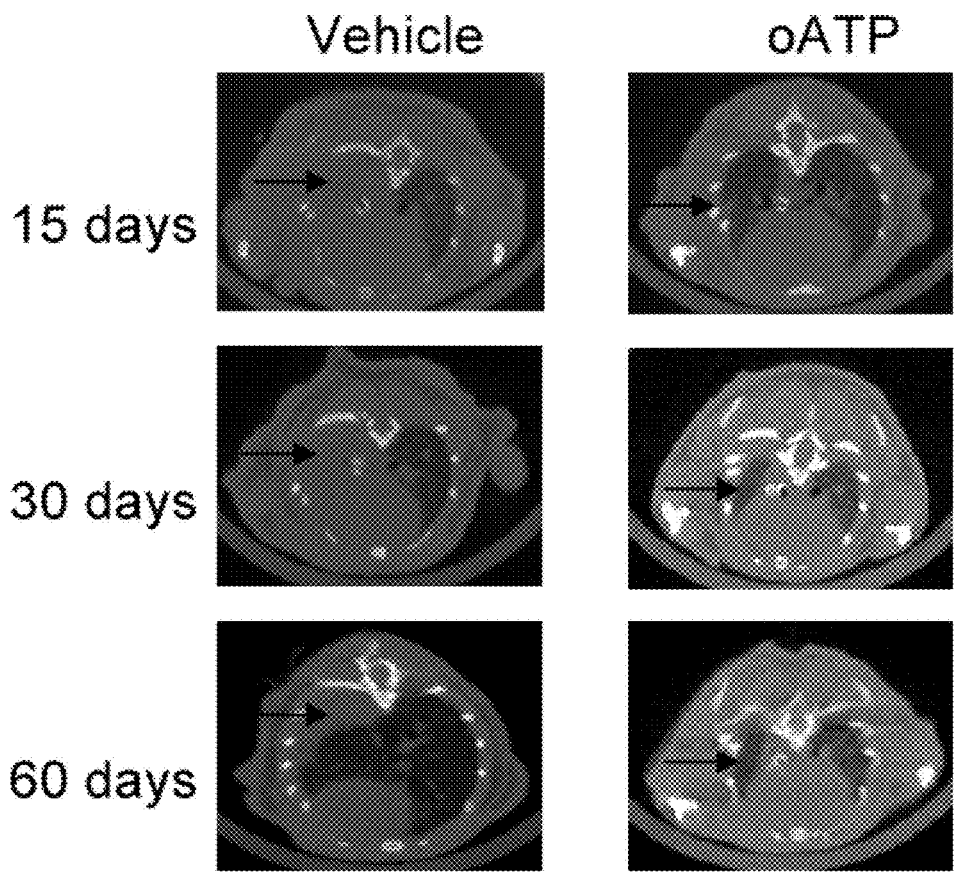
Figure 11D:
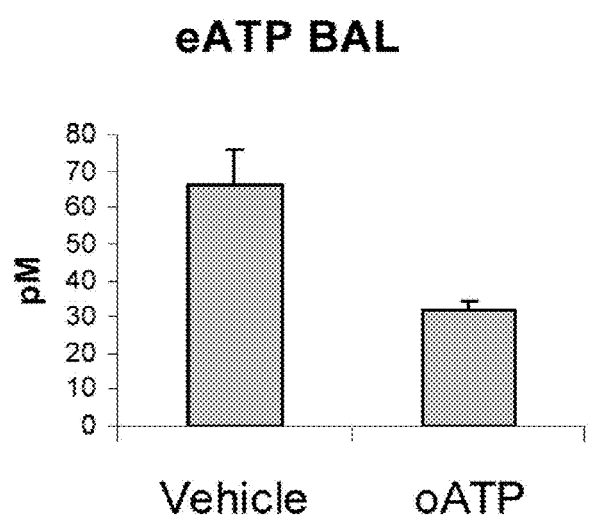

The mouse orthotopic lung transplant model was used to examine whether the immune modulating actions of oATP is capable of prolonging lung allograft survival. Lung transplants were performed using mice across a full MHC mismatch, BALB/c as donor and B6 as recipient and lung allografts evaluated 15, 30 and ≥60 days after transplantation. FIGS. 11A-11C illustrate representative samples of lung allografts at the three time points. There is progression of lung allograft injury/rejection so that by ≥60 days the lung is small, fibrotic and non-functional. Using either the non-selective antagonist, suramin, or the more selective P2X7R inhibitor, oATP, there was a reduction of acute rejection and improved lung function (reduced PawP) of lung allogratfts 15 days after transplantation. More importantly, the beneficial effects of oATP were maintained so that both lung function, based on PawP after delivery of a fixed tidal volume, and ACR grade were similar for the three time points. ACR grade using ISHLT guidelines {Stewart, 2007 #23} was ~A2 for all three time points. In order to monitor progression of lung allografts, selected mice had thoracic imaging performed at the early, mid and later time points. FIG. 1C shows examples of thoracic CT imaging for both vehicle and oATP treated allografts. At 15 and 30 days there is consolidation of the lung allograft and by ≥60 days, there is a loss of lung volume and compensation by expansion of the right lung while left lung allografts of oATP treated recipients had little infiltrate at all three time points. ATP levels from BAL were increased in lung allografts and blocking this pathway resulted in a significant reduction of BAL ATP levels (FIG. 11D).

Figure 12:
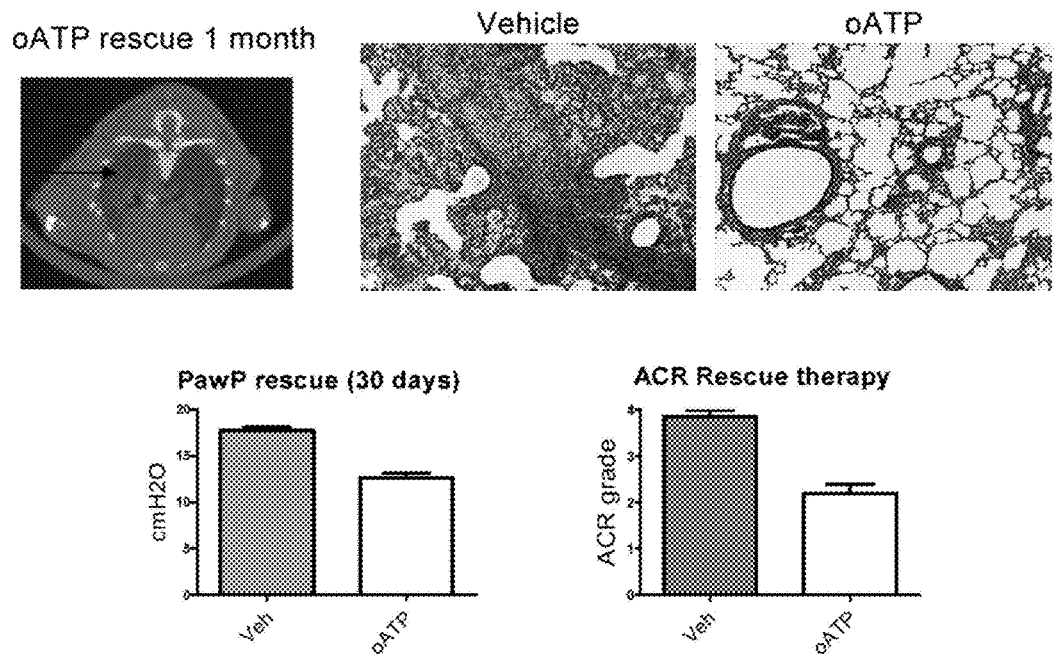
FIG. 12 demonstrates oATP rescue therapy. Recipient mice were treated with oATP starting 15 days after transplant and allografts evaluated 30 days after transplant (oATP treatment days 15-30). Shown is a representative microCT image following oATP rescue therapy showing minimal infiltrate as compared to the expected consolidation after 30 days (FIG. 11C). Also shown are representative HE stains of vehicle and oATP treated lung allografts. The graphs illustrate PawP and ACR grade with oATP treatment resulting in significant improvement (P<0.05, N=6 for each group).

To determine the effectiveness of oATP in treating rejection, rescue dosing was performed starting 15 days after transplant and given daily for an additional 15 days with lung allografts evaluated 30 days following transplantation. After 15 days, untreated lung allografts demonstrate moderate to severe rejection (~A3), and after 30 days nearly all untreated lung allografts demonstrate severe rejection (A4). Treatment started 15 days after transplant (time point for moderate to severeACR) not only prevented the progression to severe ACR and impaired lung function, but resulted in a reduction of ACR to A2 and improved lung function based on reduced PawP (FIG. 12). Thoracic imaging correlated with the improved histology and lung function showing limited infiltrate as compared to more severe infiltrate and consolidation observed in untreated allografts (see FIG. 12 as compared to FIG. 11C).

Figure 13A:
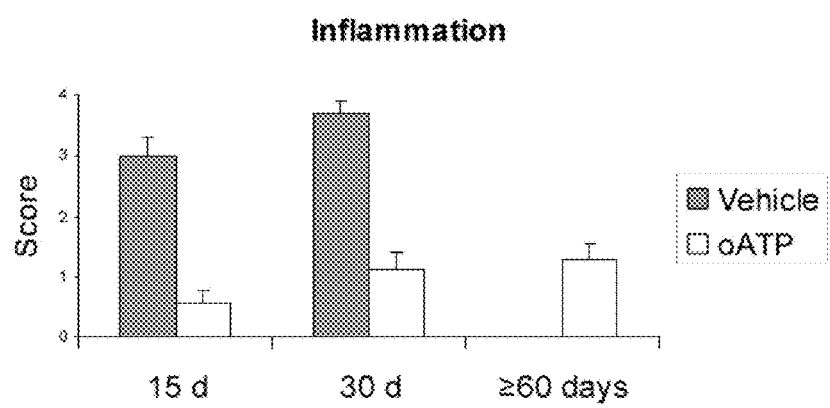
FIGS. 13A-13D demonstrate lung inflammation.
Figure 13B:
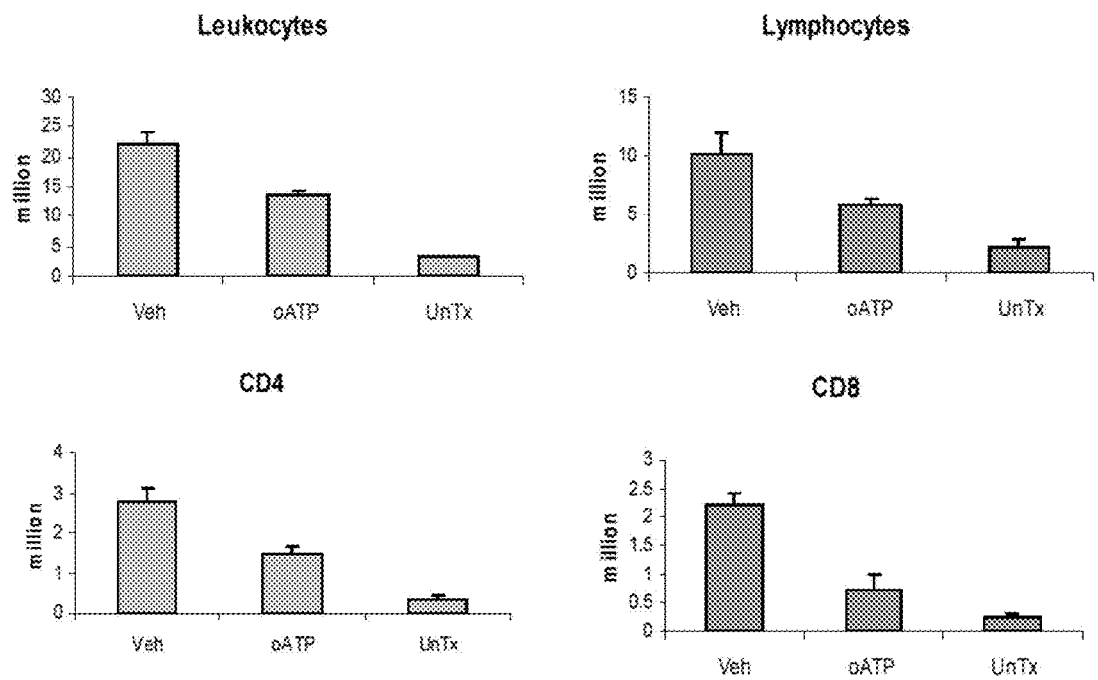

ATP plays a role in both innate and adaptive immune responses and therefore may affect both lymphocytes and non-lymphocyte inflammatory cells. Although, there was some evidence of cellular infiltrate around vessels in the oATP treated samples, there appeared to be much less inflammation within the interstitium and alveolar spaces of oATP treated lung allografts as compared to untreated allografts. Using a qualitative scoring system (0—none, 1—minimal or focal, 2—moderate or focal/diffuse, 3—diffuse, 4—extensive with nearly complete loss of lung architecture), a remarkable reduction in the amount of inflammation was observed (FIG. 13A) in the oATP treated allografts. As a correlate to the histological score for inflammation, a decrease was observed in inflammation based on the number of inflammatory cells isolated from lung allografts with oATP treated grafts having nearly half the number of leucocytes and lymphocytes (both CD4 and CD8) using flow cytometric analysis (FIG. 13B).

Figure 13C:
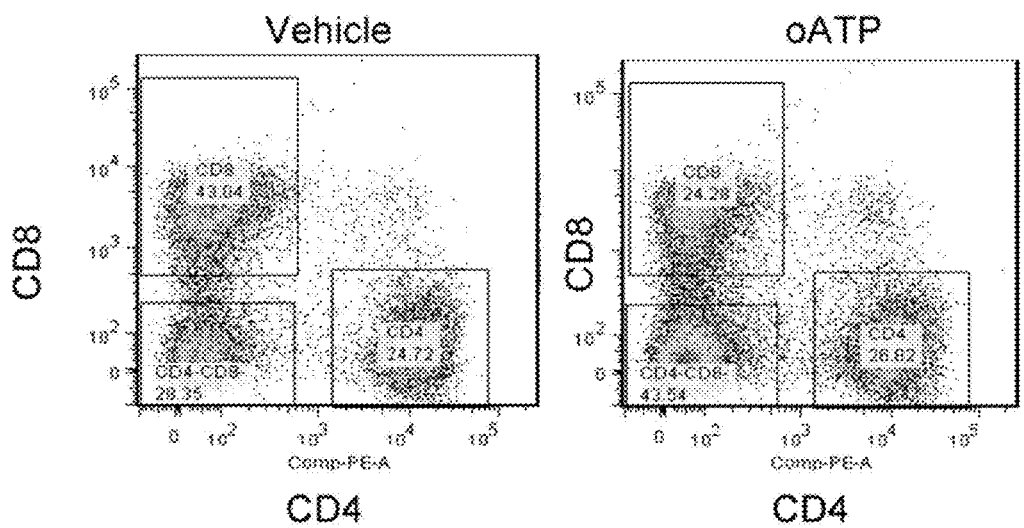
Figure 14:
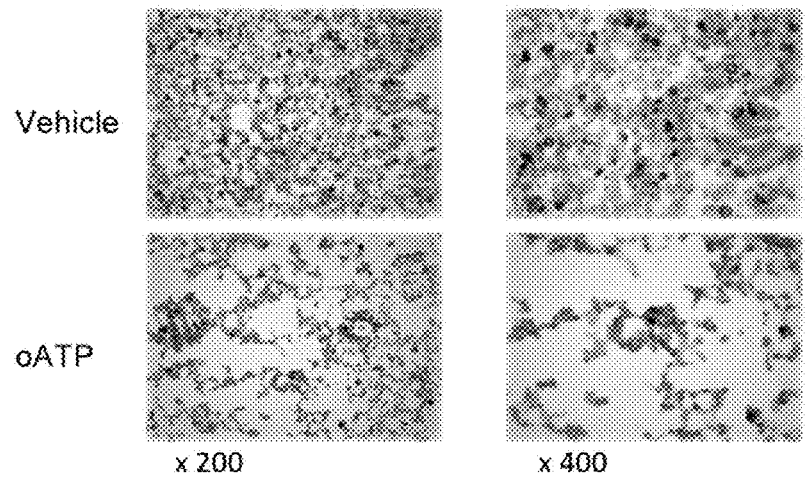
FIG. 14 demonstrates immunohistochemistry for CD4 and CD8 T cells. Shown are representative immunohistochemistry stained lung allografts (×200 and ×400) for both CD4 and CD8 cells of vehicle and oATP treated samples. The graph illustrates the number of positively stained cells per high power field (mean of N=3 per group with each individual sample the average of positive cells in 10 HPF).
Figure 14:
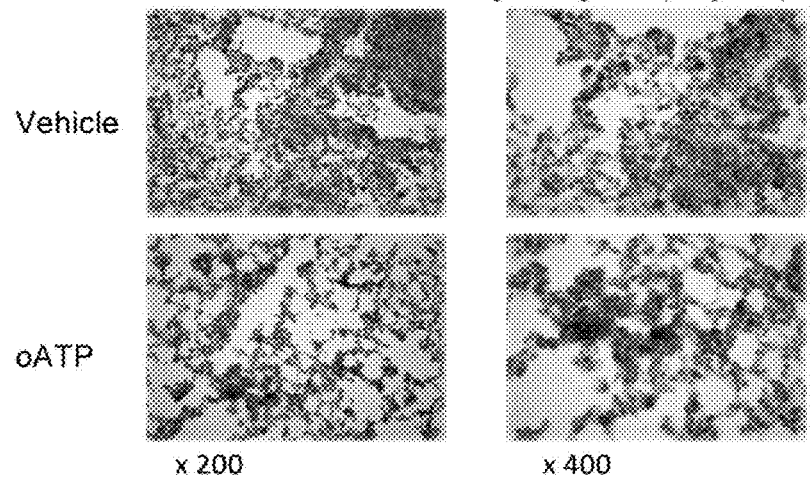
Figure 14:
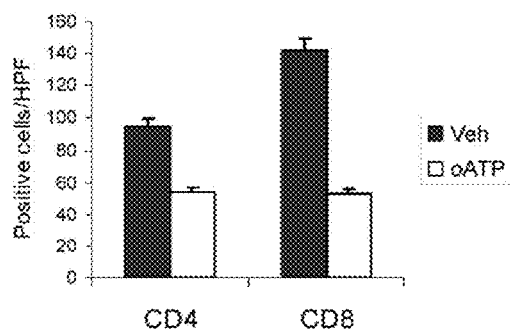

In lung allografts there is an increase in both CD4 and CD8 T cells although there is evidence that early rejection is primarily a CD8 mediated event in mouse lung allografts {Gelman, 2008 #13}. A decrease was observed in both CD4 and CD8 T cells within oATP treated lung allografts. Based on flow cytometry, there appeared to be a greater affect on CD8 T cells with a reduction in both the number and percentage of CD8 T cells isolated from oATP treated lung allografts (FIGS. 13B-13C). FIG. 14 illustrates examples of immunohistochemical staining for CD4 and CD8 positive T-cells in both untreated and oATP treated lung allografts and the number of cells/high power field.

Figure 13D:
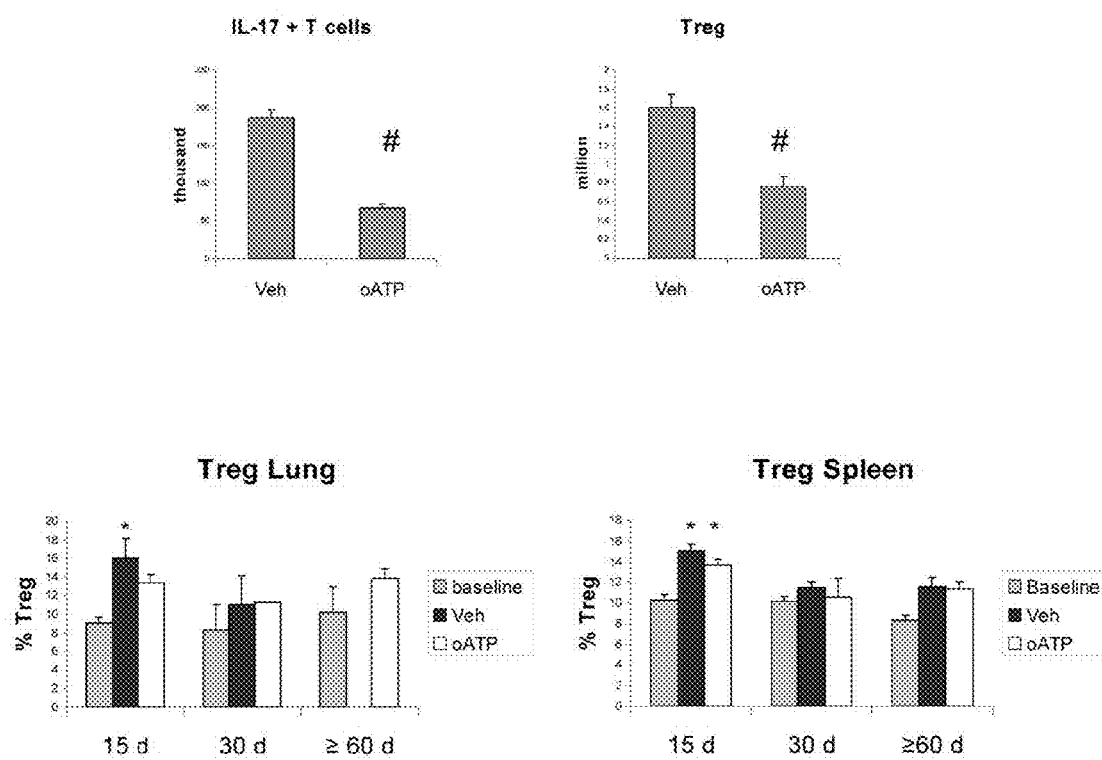

Th17 cells were evaluated after 15 days and similar to CD4+ T cells, there was not a significant difference in the percentage of Th17 cells; however, there was a reduction in the total number of Th17 cells isolated from the oATP treated lung allografts (FIG. 13D). Regulatory T cells (Treg), CD4+CD25+foxp3+, were also noted to be increased in both lung and spleen of untreated recipients after 15 days while at the later time point there was not a remarkable difference in the percentage of Treg (FIG. 13D). Again there was not a remarkable difference in the percentage of Treg in oATP treated samples as compared to untreated; however, there was reduction in total number of cells with oATP treatment (FIG. 13D).

Figure 15A:
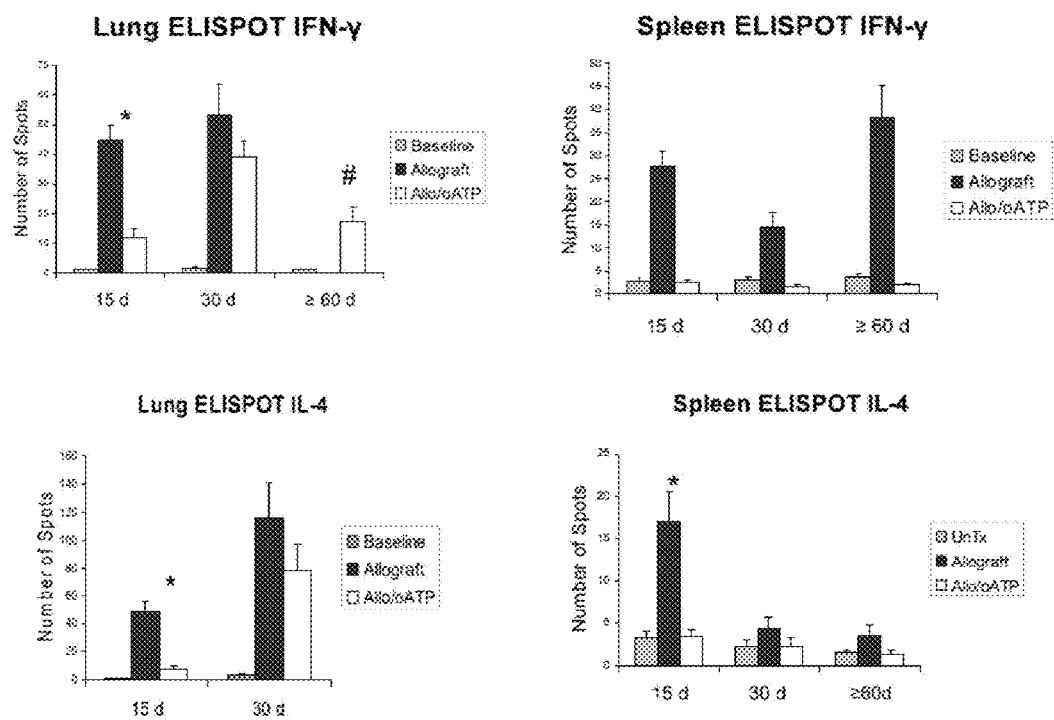
FIGS. 15A-15C demonstrate effector cells levels.

Although there was a significant reduction of T cells in oATP treated allografts there were still a significant amount over normal or isografts (data not shown) resulting in an ACR grade of A1-2. The amount of T cells and histologic changes were fairly consistent from 15 to 60 days post-transplant and more importantly lung function was maintained suggesting that there was no ongoing progression in lung injury. It was then determined if T cells that were present had impaired activation and function. T-cells were isolated from untransplanted control lungs, lung allografts, and spleens under both treated and untreated conditions, and examined based on ELISPOT for both IFN-γ and IL-4 (FIG. 15A). There were a higher number of IFN-γ and IL-4 positive T cells from lung allografts. Treatment with oATP resulted in an impaired IFN-γ and IL-4 response which was most pronounced after 15 days with less of an effect on T cells isolated from lung allografts after 30 days. There was a similar early response in T cells from spleen which was also impaired by oATP treatment. Overtime, there was less of an IL-4 response, however, the IFN-γ response was maintained and oATP maintained its suppressive effect.

Figure 15B:
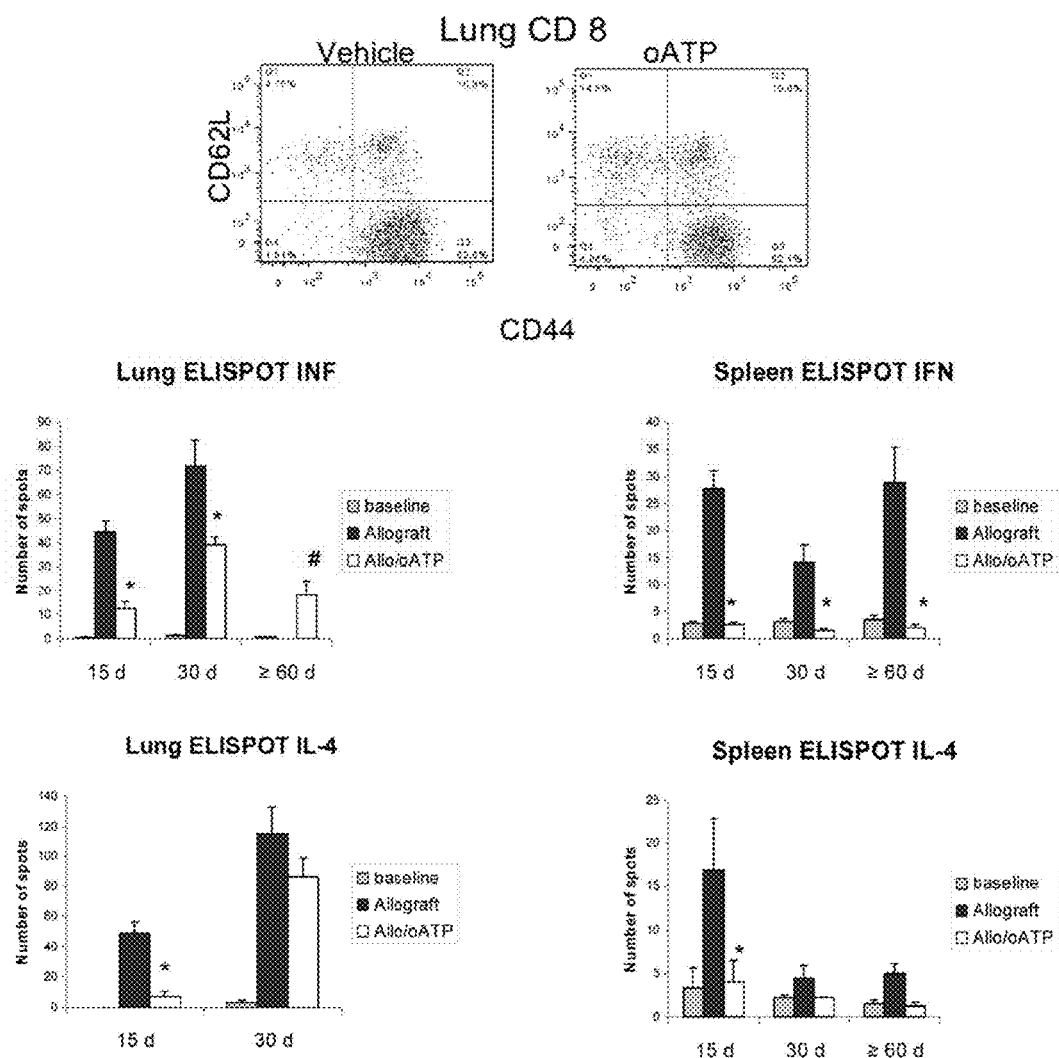
Figure 15C:
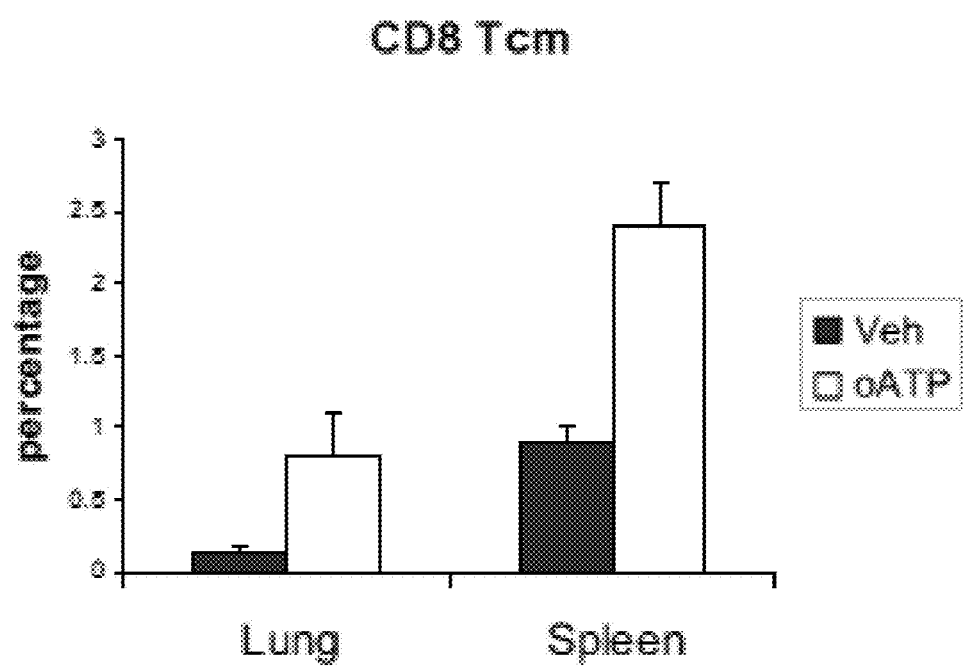

Activation of T-cells to effector memory cells was furthered assessed in response to oATP treatment from both lung and spleen (FIG. 15B). Similar to the cytokine response, T cells isolated from lung allografts showed an increase in activation and conversion of both CD4 and CD8 naïve T cells to effector memory cells (CD44highCD62Llow phenotype) and oATP had an inhibitory effect upon lung allograft T cell activation. Again there was less of an affect noted after 30 days, however, the suppressive effect was maintained upon T cells within lung allografts ≥60 days post transplant. There was less of an affect and inhibitory response upon T cells isolated from the spleen.

Figure 16A:
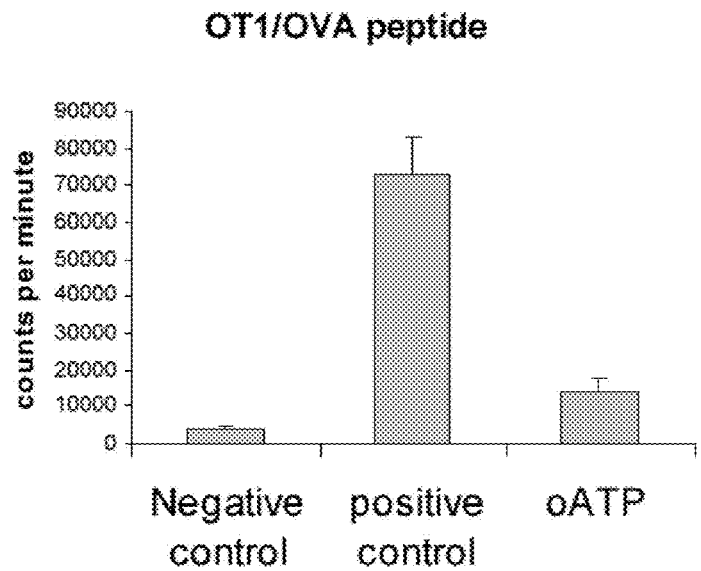
FIGS. 16A-16C demonstrate CD8 T cell response and cytotoxicity.
Figure 16B:
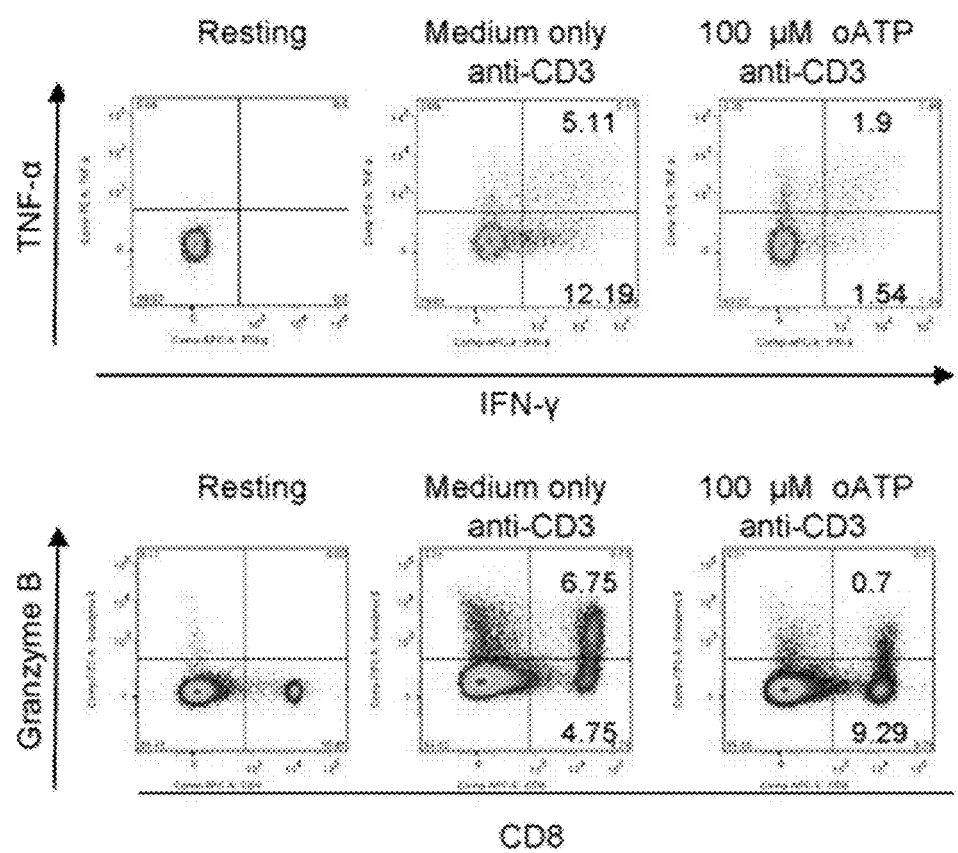

CD8 cells are believed to be the critical cell in mediating mouse lung allograft rejection (19) and although there was a reduction in CD8 effector T cells, there was no reduction in CD44+CD62L+ cells. To better determine the fate of central memory (Tcm) CD8 T cells, CD8+CD44+CD62L+ CCR7+ cells were assessed from both lung allografts and spleen in oATP treated and untreated recipients. Treatment with oATP resulted in an increase in the percentage of CD8 Tcm (FIG. 16B). The actions of oATP upon CD8 activation/function was further evaluated based on the expression of Th1 cytokines, TNF-α and IFN-γ, and the cytolytic protein granzyme B with oATP having an inhibitory effect upon the activation of CD8 effector function with a reduction in TNF-α, IFN-γ, and granzyme B (FIG. 16B).

Figure 16C:
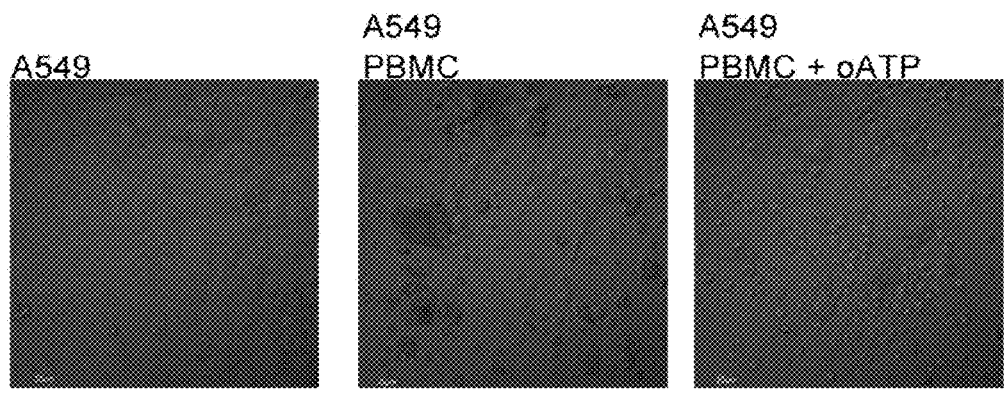
Figure 16C:
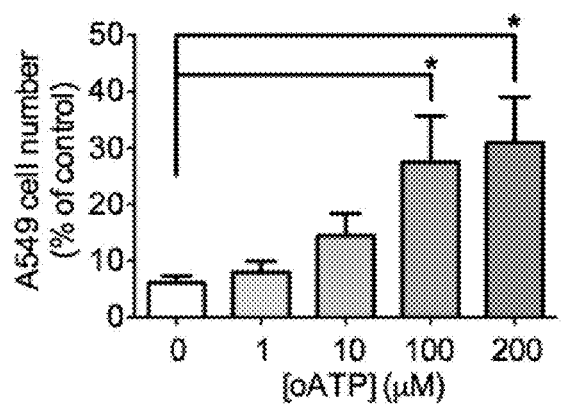

To assess the inhibitory actions of oATP upon CD8 cells, a CD8 specific response was analyzed by utilizing OT1 splenocytes stimulated with OVA peptide. OT1 mice (C57BL/6-Tg(TcraTcrb)1100Mjb/J) contain transgenic inserts for mouse Tcra-V2 and Tcrb-V5 genes that recognize chicken ovalbumin residues 257-265 in the context of H2K$^b$ with a specific response of CD8$^+$ T cells {Hogquist, 1994 #14}. OT1 cells were stimulated with the OVA peptide and proliferation evaluated under untreated and oATP treated conditions. Co-treatment with oATP resulted in a dramatic reduction of an allo-specific CD8 activation/proliferation (FIG. 16A). In addition, it was found that oATP inhibited the activation of CD8 effector function with a reduction in the cytolytic protein granzyme B (FIG. 16B). The cytolytic effector function was also examined in response to oATP using isolated human PBMC exposed to human epithelial-like lung cell line, A549, and observed a remarkable reduction in cytolytic activity with increasing doses of oATP (FIG. 16C).

To better understand its potential as a therapeutic agent as compared to current treatments, the effects of oATP were compared to the calcineurin inhibitor, CSA and in combination with either CSA or the mTOR inhibitor, Rap, CTLA-4Ig, and oATP in combination with CAS, Rap, or CTLA-4Ig (FIG. 17). Similar to what was previously reported {De Vleeschauwer, #24}, it was found that CSA or CTLA-4Ig alone had limited benefits in reducing acute rejection. In addition, treatment with the combination of CSA and oATP resulted in no added benefits to oATP alone. It was observed that adding Rap to CSA or CTLA-4Ig reduced the severity of rejection; however, the combination of Rap plus oATP was not different from oATP alone.

Discussion

ATP is released from inflammatory cells including T cells and plays a role in the development of lung injury. ATP is increased in activated T cells and its release is believed to be an autocrine response enhancing T cell activation {Lang, #8; Schenk, 2008 #3; Trautmann, 2009 #11} through its binding of P2XR7, the major purinergic receptor found on T cells. As described herein, ATP levels are increased in mouse orthotopic lung allografts and blocking the purinergic pathway reduced ATP levels and reduced lung injury with improved survival of lung allografts. It was also found that P2XR7 was increased in T cells isolated from mouse lung allografts (data not shown); therefore, it was examined whether blocking P2XR7 activation of T cells would reduce lung allograft rejection and prolong lung allograft survival. Using the well characterized inhibitor of P2XR7, oATP {Arulkumaran, #12}, it was demonstrated herein that oATP treatment of mouse recipients resulted in reducing ACR but more importantly continued use of oATP maintained its action and prolonged lung allograft survival. Allografts from later time points, ≥60 days, were similar to allografts from earlier time points based on appearance, histology, function, and imaging while untreated allografts showed severe disease/fibrosis with time. Not only was oATP graft protective properties maintained with time, but oATP was able to at least in part rescue lung allografts against severe rejection. Treating lung allografts at a time where most allografts showed moderate to severe rejection (A3) resulted in a reduction to approximately A2 while untreated allografts progressed to severe rejection (A4).

It is demonstrated herein that oATP reduced the number of both CD4 and CD8 T cells within lung allografts and inhibited the activation and release of cytokines from both CD4 and CD8 cells. However, the CD8 response appeared to be more robust with a greater number of CD8 T cells in the lung and the reactivity of CD8 T cells in the spleen maintained with time. In addition, a previous report {Gelman, 2008 #13} indicated that the CD8 response appears to be the major pathway for mouse lung rejection; therefore, the effect of oATP upon CD8 T cells was further evaluated. In order to explore CD8 specific activation, OT1 mice which have a CD8 specific response to its antigen, OVA peptide {Hogquist, 1994 #14} were used. Treatment of stimulated CD8 T cells with oATP was able to impair activation with reduced IFN-γ and TNF-α expression along with the cytotoxic machinery, granzyme B, indicating a reduction in effector cytotoxic function of CD8 T cells. It is demonstrated herein that oATP treatment resulted in a dramatic inhibition of CD8 T cell allospecific proliferation. To further evaluate CD8 effector function, it was examined whether oATP effects upon the cytotoxic machinery. There was a remarkable reduction in granzyme B expression in stimulated CD8 T cells indicating a reduction in effector cytotoxic function of CD8 T cells. It was also found that oATP impaired the CTL response of human cells with impaired cytotoxicity of human PBMC upon human lung epithelial-like cells.

Extracellular ATP is a DAMP for immune activation {Junger, #10; Spooner, #15} and plays a role in acute inflammation with higher concentrations resulting in a skewing towards Th 1 response through the P2XR7 receptor {Schnurr, 2000 #16}. The P2XR7 receptor mediates the activation and development of inflammasomes and the progression of bleomycin inflammation and fibrosis {Riteau, #17}. It was found that blocking P2XR7 with oATP reduced IFN-γ expression as noted above and similar effects were seen upon Th1 proinflammatory cytokines such as TNF-α and IL-1β expression (data not shown). Although, this study focused more upon rejection and T cell responses, it appeared that oATP resulted in a reduction in inflammation based on histology and number of leucocytes in lung allografts. Therefore, without wishing to be bound by theory, oATP may have additional benefits in lung transplantation with not only inhibiting T cell mediated rejection but having the potential of reducing early injury related to primary graft dysfunction.

L-selectin, CD62L is a cell adhesion molecule found on naïve and central memory T cells with a loss of CD62L identifying effector memory cells that are capable of performing immediate effector function {Unsoeld, 2005 #18}. P2XR7 mediates ATP response on T cells including CD62L shedding {Chused, 1996 #20; Taylor, 2009 #19}. It was found that the P2XR7 inhibitor, oATP, impaired T cell activation with reduced cytokine expression, effector function, and the development of Tem with reduced CD62L shedding in this transplant model. More importantly, this effect was maintained in lung CD8 T cells from the lung. Since the development of memory T cells are believed to be a barrier to maintaining allograft survival {Brook, 2006 #26}, the ability of oATP to reduce Tem and more importantly the activation of these T cells could partially explain some of its long term benefits. Although there was a reduction in effector function and memory, treatment with oATP did not result in a reduction but rather an increase in central memory CD8 T cells (CD44+CD62L+CCR7+).

The induction of T cell tolerance prolongs allograft survival and there are several pathways in which T cells may be modified to reduce rejection including deletion, anergy, immune deviation, and the generation of suppressive T cells (29). Although a decrease was observed in the number of Treg within lung allografts, the profile with respect to the percentage of Tregs was similar between treated and untreated recipients. This is similar to what was found in cardiac and islet allografts where oATP benefits were not thought to be through the generation of Treg suppression (11, 17). Bystander CD8 Tcm have also been shown to have suppressive properties upon T cells and suppress allograft rejection (30). As discussed above, oATP treatment reduced effector function and memory cells while there was an increase in the central memory profile suggesting a potential increase in a suppressive population.

ATP was shown to play a role in Th17 differentiation (31) and Th17 cells are thought to be important in the pathophysiology of lung transplant rejection (32). While oATP was shown to impair the differentiation of Th17 cells in vitro, there was a differential response of Th17 cells with oATP treatment between cardiac and islet cell transplants with a limited response of Th17 cells in islet cell transplantation (11, 17). In lung transplants, a limited response of Th17 cells to oATP treatment was observed, similar to islet cells with no significant reduction in the percentage of cells but an overall reduction in the number of Th17 cells from lung allografts.

It is demonstrated herein that blocking the purinergic pathway with the P2XR7 inhibitor, oATP, results in a reduction in mouse lung allograft rejection, which is maintained over time. Calcineurin inhibitors are the foundation of immunosuppression in lung transplantation and have played a major role in lung transplant becoming a clinical entity. It is demonstrated herein that the protection afforded by oATP was more robust as compared to CSA and adding CSA to oATP had no additive protection. A recent study showed that adding Rap to oATP had an additive effect upon islet cell allografts survival {Vergani, #25}. Although the same approach was utilized, no significant benefits were observed with the combination of Rap/oATP as compared to oATP alone within 1 month of transplantation based on histology or PawP. Another common approach in generating allograft tolerance in mice is blocking co-stimulation with CTLA-4Ig which is believed to be mediated through the induction of Tregs (33). Interestingly, this approach is of limited benefit in the mouse lung transplant model (19), and as demonstrated herein.

REFERENCES

1. Weigt, S. S., W. D. Wallace, A. Derhovanessian, R. Saggar, R. Saggar, J. P. Lynch, and J. A. Belperio. Chronic allograft rejection: epidemiology, diagnosis, pathogenesis, and treatment. *Semin Respir Crit Care Med* 31(2): 189-207.
2. Christie, J. D., L. B. Edwards, A. Y. Kucheryavaya, C. Benden, A. I. Dipchand, F. Dobbels, R. Kirk, A. O. Rahmel, J. Stehlik, and M. I. Hertz. The Registry of the International Society for Heart and Lung Transplantation: 29th adult lung and heart-lung transplant report-2012. *J Heart Lung Transplant* 31(10):1073-86.
3. Schenk, U., A. M. Westendorf, E. Radaelli, A. Casati, M. Ferro, M. Fumagalli, C. Verderio, J. Buer, E. Scanziani, and F. Grassi. 2008. Purinergic control of T cell activation by ATP released through pannexin-1 hemichannels. *Sci Signal* 1(39):ra6.
4. Yegutkin, G. G., A. Mikhailov, S. S. Samburski, and S. Jalkanen. 2006. The detection of micromolar pericellular ATP pool on lymphocyte surface by using lymphoid ecto-adenylate kinase as intrinsic ATP sensor. *Mol Biol Cell* 17(8):3378-85.
5. Junger, W. G. Immune cell regulation by autocrine purinergic signalling. *Nat Rev Immunol* 11(3):201-12.
6. Yegutkin, G. G., T. Henttinen, S. S. Samburski, J. Spychala, and S. Jalkanen. 2002. The evidence for two opposite, ATP-generating and ATP-consuming, extracellular pathways on endothelial and lymphoid cells. *Biochem J* 367(Pt 1):121-8.
7. Spooner, R., and O. Yilmaz. The role of reactive-oxygen-species in microbial persistence and inflammation. *Int J Mol Sci* 12(1):334-52.
8. Trautmann, A. 2009. Extracellular ATP in the immune system: more than just a "danger signal". *Sci Signal* 2(56):pe6.
9. Placido, R., G. Auricchio, S. Falzoni, L. Battistini, V. Colizzi, E. Brunetti, F. Di Virgilio, and G. Mancino. 2006. P2X(7) purinergic receptors and extracellular ATP mediate apoptosis of human monocytes/macrophages infected with Mycobacterium tuberculosis reducing the intracellular bacterial viability. *Cell Immunol* 244(1):10-8.
10. Lang, P. A., D. Merkler, P. Funkner, N. Shaabani, A. Meryk, C. Krings, C. Barthuber, M. Recher, W. Bruck, D. Haussinger, P. S. Ohashi, and K. S. Lang. Oxidized ATP inhibits T-cell-mediated autoimmunity. *Eur J Immunol* 40(9):2401-8.
11. Vergani, A., S. Tezza, F. D'Addio, C. Fotino, K. Liu, M. Niewczas, R. Bassi, R. D. Molano, S. Kleffel, A. Petrelli, A. Soleti, E. Ammirati, M. Frigerio, G. Visner, F. Grassi, M. E. Ferrero, D. Corradi, R. Abdi, C. Ricordi, M. H. Sayegh, A. Pileggi, and P. Fiorina. Long-term heart transplant survival by targeting the ionotropic purinergic receptor P2X7. *Circulation* 127(4):463-75.
12. Bizargity, P., K. Liu, L. Wang, W. W. Hancock, and G. A. Visner Inhibitory effects of pirfenidone on dendritic cells and lung allograft rejection. *Transplantation* 94(2): 114-22.
13. Iken, K., K. Liu, H. Liu, P. Bizargity, L. Wang, W. W. Hancock, and G. A. Visner. Indoleamine 2,3-dioxygenase and metabolites protect murine lung allografts and impair the calcium mobilization of T cells. *Am J Respir Cell Mol Biol* 47(4):405-16.
14. Liu, H., L. Liu, B. S. Fletcher, and G. A. Visner. 2006. Novel action of indoleamine 2,3-dioxygenase attenuating acute lung allograft injury. *Am J Respir Crit Care Med* 173(5):566-72.
15. Liu, H., L. Liu, B. S. Fletcher, and G. A. Visner. 2006. Sleeping Beauty-based gene therapy with indoleamine 2,3-dioxygenase inhibits lung allograft fibrosis. *Faseb J* 20(13):2384-6.
16. Stewart, S., M. C. Fishbein, G. I. Snell, G. J. Berry, A. Boehler, M. M. Burke, A. Glanville, F. K. Gould, C. Magro, C. C. Marboe, K. D. McNeil, E. F. Reed, N. L. Reinsmoen, J. P. Scott, S. M. Studer, H. D. Tazelaar, J. L. Wallwork, G. Westall, M. R. Zamora, A. Zeevi, and S. A. Yousem. 2007. Revision of the 1996 working formulation for the standardization of nomenclature in the diagnosis of lung rejection. *J Heart Lung Transplant* 26(12):1229-42.
17. Vergani, A., C. Fotino, F. D'Addio, S. Tezza, M. Podetta, F. Gatti, M. Chin, R. Bassi, R. D. Molano, D. Corradi, R. Gatti, M. E. Ferrero, A. Secchi, F. Grassi, C. Ricordi, M. H. Sayegh, P. Maffi, A. Pileggi, and P. Fiorina. Effect of the purinergic inhibitor oxidized ATP in a model of islet allograft rejection. *Diabetes* 62(5):1665-75.
18. Azzi, J., L. Tang, R. Moore, R. Tong, N. El Haddad, T. Akiyoshi, B. Mfarrej, S. Yang, M. Jurewicz, T. Ichimura, N. Lindeman, J. Cheng, and R. Abdi. Polylactide-cyclosporin A nanoparticles for targeted immunosuppression. *Faseb J* 24(10):3927-38.
19. Gelman, A. E., M. Okazaki, J. Lai, C. G. Kornfeld, F. H. Kreisel, S. B. Richardson, S. Sugimoto, J. R. Tietjens, G. A. Patterson, A. S. Krupnick, and D. Kreisel. 2008. CD4+ T lymphocytes are not necessary for the acute rejection of vascularized mouse lung transplants. *J Immunol* 180(7): 4754-62.

20. De Vleeschauwer, S., W. Jungraithmayr, S. Wauters, S. Willems, M. Rinaldi, A. Vaneylen, S. Verleden, A. Willems-Widyastuti, K. Bracke, G. Brusselle, E. Verbeken, D. Van Raemdonck, G. Verleden, and B. Vanaudenaerde. Chronic rejection pathology after orthotopic lung transplantation in mice: the development of a murine BOS model and its drawbacks. *PLoS One* 7(1):e29802.
21. Burnstock, G., I. Brouns, D. Adriaensen, and J. P. Timmermans. Purinergic signaling in the airways. *Pharmacol Rev* 64(4):834-68.
22. Schnurr, M., F. Then, P. Galambos, C. Scholz, B. Siegmund, S. Endres, and A. Eigler. 2000. Extracellular ATP and TNF-alpha synergize in the activation and maturation of human dendritic cells. *J Immunol* 165(8):4704-9.
23. Riteau, N., P. Gasse, L. Fauconnier, A. Gombault, M. Couegnat, L. Fick, J. Kanellopoulos, V. F. Quesniaux, S. Marchand-Adam, B. Crestani, B. Ryffel, and I. Couillin. Extracellular ATP is a danger signal activating P2X7 receptor in lung inflammation and fibrosis. *Am J Respir Crit Care Med* 182(6):774-83.
24. Arulkumaran, N., R. J. Unwin, and F. W. Tam. A potential therapeutic role for P2X7 receptor (P2X7R) antagonists in the treatment of inflammatory diseases. *Expert Opin Investig Drugs* 20(7):897-915.
25. Unsoeld, H., and H. Pircher. 2005. Complex memory T-cell phenotypes revealed by coexpression of CD62L and CCR7. *J Virol* 79(7):4510-3.
26. Chused, T. M., S. Apasov, and M. Sitkovsky. 1996. Murine T lymphocytes modulate activity of an ATP-activated P2Z-type purinoceptor during differentiation. *J Immunol* 157(4):1371-80.
27. Taylor, S. R., M. Gonzalez-Begne, D. K. Sojka, J. C. Richardson, S. A. Sheardown, S. M. Harrison, C. D. Pusey, F. W. Tam, and J. I. Elliott. 2009. Lymphocytes from P2X7-deficient mice exhibit enhanced P2X7 responses. *J Leukoc Biol* 85(6):978-86.
28. Brook, M. O., K. J. Wood, and N. D. Jones. 2006. The impact of memory T cells on rejection and the induction of tolerance. *Transplantation* 82(1):1-9.
29. Bishop, G. A., F. L. Ierino, A. F. Sharland, B. M. Hall, S. I. Alexander, M. S. Sandrin,
P. T. Coates, and G. W. McCaughan. Approaching the promise of operational tolerance in clinical transplantation. *Transplantation* 91(10):1065-74.
30. Wan, N., H. Dai, T. Wang, Y. Moore, X. X. Zheng, and Z. Dai. 2008. Bystander central memory but not effector memory CD8+ T cells suppress allograft rejection. *J Immunol* 180(1):113-21.
31. Atarashi, K., J. Nishimura, T. Shima, Y. Umesaki, M. Yamamoto, M. Onoue, H. Yagita, N. Ishii, R. Evans, K. Honda, and K. Takeda. 2008. ATP drives lamina propria T(H)17 cell differentiation. *Nature* 455(7214):808-12.
32. Shilling, R. A., and D. S. Wilkes. Role of Th17 cells and IL-17 in lung transplant rejection. *Semin Immunopathol* 33(2):129-34.
33. McGrath, M. M., and N. Najafian. The role of coinhibitory signaling pathways in transplantation and tolerance. *Front Immunol* 3:47.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Example 36: Treatment of Diabetes

Islets from 4-week-old NOD mice showed moderate infiltrate (FIG. 18A), mainly consisting of CD3+ cells (FIG. 18B), which appeared to be P2X7R+ (FIG. 18C). Consequently, NOD mice were treated with oATP. ATP/P2X7R targeting with oATP (administered daily i.p. for 30 days) was found to delay diabetes onset in 4-week-old NOD mice alone (early prevention study, FIG. 18D) and in 10-week-old NOD mice when associated with Rapamycin (late prevention study, FIG. 18E).

It was also demonstrated that ATP/P2X7R targeting can reverse experimental diabetes and hyperglycemia in NOD mice (FIGS. 19A-19E).

What is claimed is:

1. A method of treating type 1 diabetes in a subject, comprising:
administering a therapeutically effective dosage of a purinergic receptor inhibitor to the subject, wherein the inhibitor is CE-224535.

2. The method of claim 1, wherein the subject is human.

* * * * *